(12) United States Patent
Choi et al.

(10) Patent No.: US 7,683,049 B2
(45) Date of Patent: Mar. 23, 2010

(54) CARBAPENEM ANTIBACTERIALS WITH GRAM-NEGATIVE ACTIVITY AND PROCESSES FOR THEIR PREPARATION

(75) Inventors: Woo-Baeg Choi, Atlanta, GA (US); Ewa Kowalik, Atlanta, GA (US)

(73) Assignee: FOB Synthesis, Inc., Kennesaw, GA (US)

( * ) Notice: Subject to any disclaimer, the term of this patent is extended or adjusted under 35 U.S.C. 154(b) by 354 days.

(21) Appl. No.: 11/150,428

(22) Filed: Jun. 10, 2005

(65) Prior Publication Data

US 2006/0069081 A1 Mar. 30, 2006

Related U.S. Application Data

(60) Provisional application No. 60/578,632, filed on Jun. 10, 2004.

(51) Int. Cl.
  *C07D 477/14* (2006.01)
  *A61P 31/04* (2006.01)
  *A61K 31/407* (2006.01)
  *A61K 31/496* (2006.01)
  *A61K 31/426* (2006.01)
  *A61K 31/5377* (2006.01)
(52) U.S. Cl. .................................. 514/210.09; 540/302
(58) Field of Classification Search .................. 540/302; 514/210.09
  See application file for complete search history.

(56) References Cited

U.S. PATENT DOCUMENTS

| 3,950,357 | A | | 4/1976 | Kahan et al. |
| 4,866,171 | A | | 9/1989 | Kumagai et al. |
| 4,933,333 | A | | 6/1990 | Sunagawa et al. |
| 4,943,569 | A | | 7/1990 | Sunagawa |
| 4,962,103 | A | | 10/1990 | Sunagawa et al. |
| 5,011,832 | A | | 4/1991 | DiNinno et al. |
| 5,034,384 | A | | 7/1991 | Greenlee et al. |
| 5,064,954 | A | * | 11/1991 | Uyeo et al. .................. 540/302 |
| 5,102,877 | A | | 4/1992 | Murata et al. |
| 5,122,604 | A | | 6/1992 | Sunagawa et al. |
| 5,539,102 | A | | 7/1996 | Sendo et al. |
| 6,255,300 | B1 | | 7/2001 | DiNinno et al. |
| 6,310,055 | B2 | | 10/2001 | Dininno et al. |
| 6,399,597 | B1 | | 6/2002 | Cama et al. |
| 2006/0074070 | A1 | * | 4/2006 | Choi et al. ............. 514/210.09 |

FOREIGN PATENT DOCUMENTS

| EP | 0184844 A | 6/1986 |
| EP | 0 292 191 | 11/1988 |
| EP | 0481116 A1 | 10/1990 |
| JP | 4-164091 | 6/1992 |

OTHER PUBLICATIONS

Alridge, K., "Ertapenem (MK-0826), a New Carbapenem: Comparative In Vitro Activity Against Clincally Significant Anaerobes," *Diagn. Microbiol. Infect. Dis.*, 2002, pp. 181-186, 44(2).

Bouffard et al., "Thienamycin Total Synthesis. 1. Synthesis of Azetidinone Precursors of (±)-Thienamycin and Its Stereoisomers," *J. Org. Chem.*, 1980, pp. 1130-1142, 45.

Cunha, B., "Ertapenem: A Review of Its Microbiologic, Pharmocokinetic and Clinical Aspects," *Drugs of Today*, 2002, pp. 195-213, 38 (3).

Edwards et al., "In Vitro Antibacterial Activity of SM-7338, a Carbapenem Antibiotic with Stability to Dehydropeptidase I," *Antimicrob. Agents Chemother.*, 1989, pp. 215-222, 33 (2).

Hazumi et al., "Mechanism of Enhanced Antipseudomonal Activity of BO-2727, a New Injectable 1-β-Methyl Carbapenem," *Antimicrob. Agents Chemother.*, 1995, pp. 702-706, 39 (3).

(Continued)

*Primary Examiner*—Mark L Berch
(74) *Attorney, Agent, or Firm*—King & Spalding

(57) ABSTRACT

The present invention provides β-methyl carbapenem compounds and pharmaceutical compositions useful in the treatment of bacterial infections and methods for treating such infections using such compounds and/or compositions, wherein the compounds are generally of the Formulae

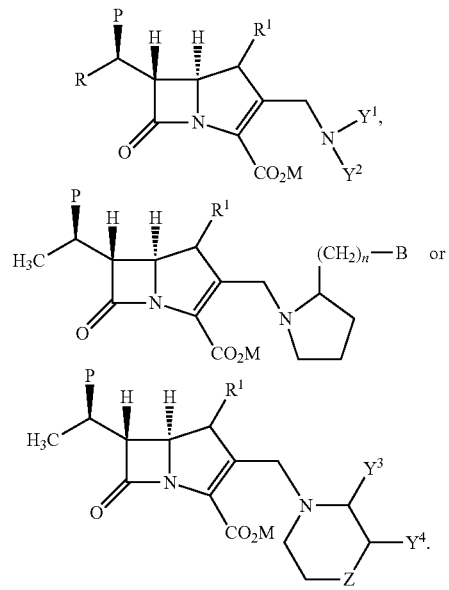

The invention includes administering an effective amount of a carbapenem compound or salt and/or prodrug thereof to a host in need of such a treatment.

42 Claims, 8 Drawing Sheets

OTHER PUBLICATIONS

Johnston et al., "Total Synthesis of (±)-Thienamycin", *J. Am. Chem. Soc.*, 1978, pp. 313-315, 100.

Kahan et al., "Thienamycin, a New β-Lactam Antibiotic I. Discovery, Taxonomy, Isolation and Physical Properties," *J. Antibiot.*, 1979, pp. 1-12, 32.

Krein et al., "A Convenient Synthesis of 2-(Alkylamino) Pyridines," *J. Org. Chem.*, 2002, pp. 4965-4967, 67.

Leanza et al., "*N*-Acetimidoyl-and *N*-Formimidoylthienamycin Derivatives: Antipseudomonal β-Lactam Antibiotics," *J. Med. Chem.*, 1979, pp. 1435-1436, 22.

Legua et al., "Safety and Local Tolerability of Intramuscularly Administered Ertapenem Diluted in Lidocaine: A Prospective, Randomized, Double-Blind Study Versus Intramuscular Ceftriaxone," *Clin. Therapeut.*, 2002, pp. 434-444, 24 (3).

Majumdar et al., "Pharmacokinetics of Ertapenem in Healthy Young Volunteers," *Antimicrob. Agents Chemother.*, 2002, pp. 3506-3511, 46(11).

Martins et al., "Design, Synthesis, and Biological Activity of a Novel Non-Cisplatin-type Platinum-Acridine Pharmacophore," *J. Med. Chem.*, 2001, pp. 4492-4496, 44.

Marvel et al., "The Structure of Urea-Formaldehyde Resins," *J. Am. Chem. Soc.*, 1946, pp. 1681-1686, 68 (9).

Nakagawa et al., "In Vitro Activity of a New Carbapenem Antibiotic, BO-2727, with Potent Antipseudomnal Activity," *Antimicrob. Agents Chemother.*, 1993, pp. 2756-2759, 37 (12).

Neu et al., "In Vitro Activity and β-Lactamase Stability of a New Carpabenem, SM-7338," *Agents Chemother.*, 1989, pp. 1009-1018, 33 (7).

Saino et al., "Purification and Properties of Inducible Penicillin β-Lactamase Isolated from *Pseudomonas maltophilia*," *Antimicrob. Agents Chemother.*, 1982, pp. 564-570, 22 (4).

Salzmann et al., "A Sterocontrolled Synthesis of (+)-Thienamycin," *J. Am. Chem. Soc.*, 1980, pp. 6161-6163, 102.

Shah et al., "Ertapenem, the First of a New Group of Carbapenems," *J. Antimicrob. Chemother.*, 2003, pp. 538-542, 52.

Shimada et al, "Overview of a New Carbapenem, Panipenem/Betamipron," *Drugs Exp Clin Res.*, 1994, pp. 241-245, 20 (6).

Tiraby et al., "A Standard Numbering Scheme for the Class A β-Lactamases," *Biochem. J.*, 1991, pp. 269-270, 276 (pt.1).

Weaver et al., "Thienamycin: New Beta-Lactam Antibiotic with Potent Broad-Spectrum Activity," *Antimicrob. Agents Chemother.*, 1979, pp. 518-521, 15 (4).

Yadav et al., "Reactions on a Solid Surface. A Simple, Economical, and Efficient Acylation of Alcohols and Amines over $Al_2O_3$", *J. Org. Chem.*, 2004, pp. 577-580, 69.

Yotsujii et al., "Properties of Novel β-*Lactamase Produced by Bacteroides fragilis*," *Antimicrob. Agents Chemother.*, 1983, pp. 925-929, 24 (6).

Wilkening et al., "Synthesis and Activity of 2(Sulfonamido)Methylcarbapenems: Discovery of a Novel, Anti-MRSA 1,8-Napthosultam Pharmacophore", Bioorganic and Medicinal Chemistry Letters 9, 1999, pp. 673-678.

Arnould et al., "New Applications of the Mitsonobu Reaction in the Synthesis of C-2 N-Methy Carbapenems", Tetrahedron Letters, 1992, vol. 33, No. 47, pp. 7133-7136.

International Search Report with Written Opinion of the Searching Authority dated Nov. 3, 2005 for PCT/US05/20518.

* cited by examiner

Thienamycin

Imipenem

Meropenem

Panipenem

Biapenem

LJC 10627

Lenapenem

BO 2727

L-786 392

Faropenem

CS 834

Sanfetrinem cilexetil

GV 118819

FIGURE 2: EXAMPLES OF GRAM-NEGATIVE ACTIVE CP'S
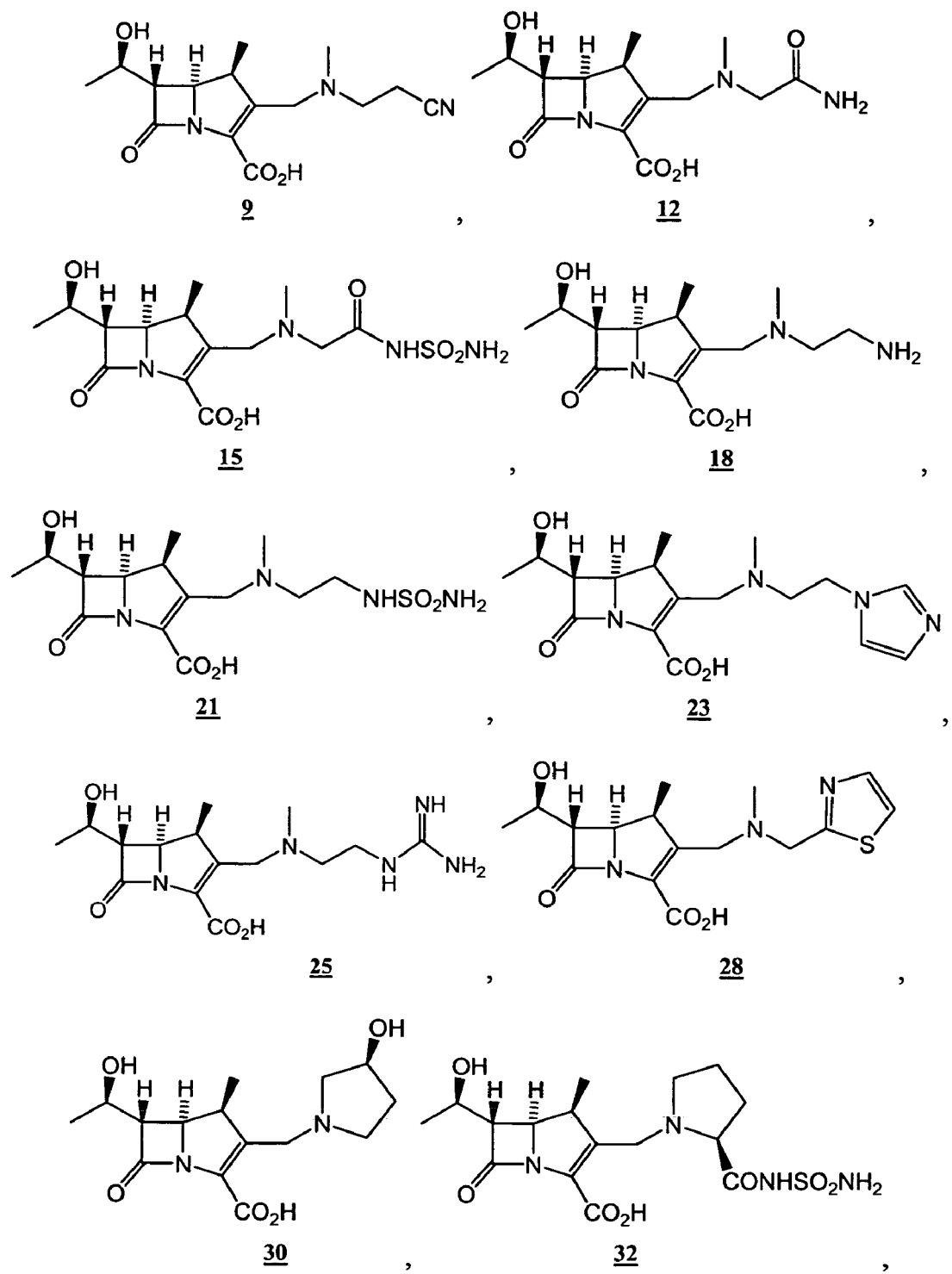

FIGURE 2, CONTINUED
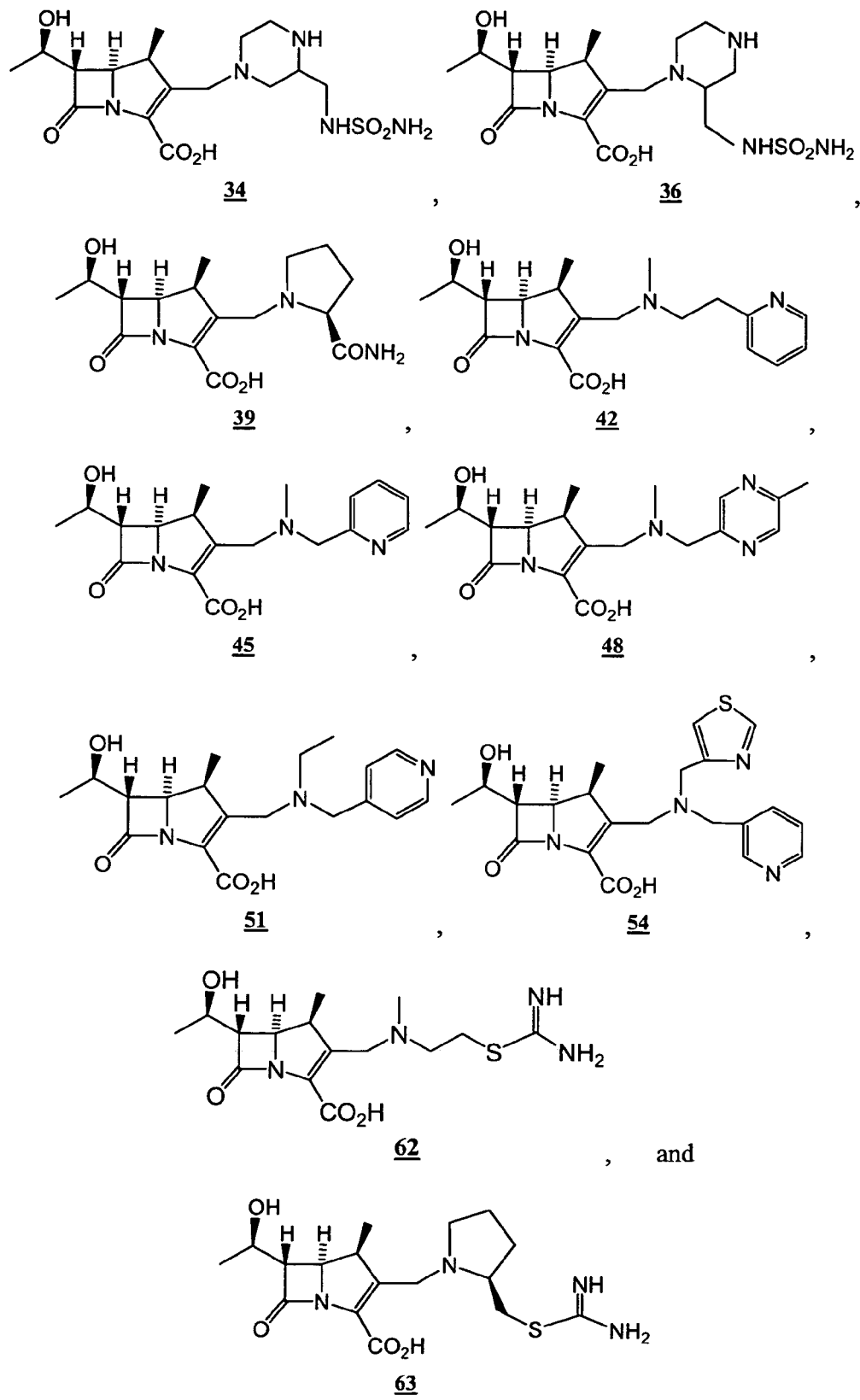

FIGURE 3: SYNTHETIC ROUTE TO CPI 5
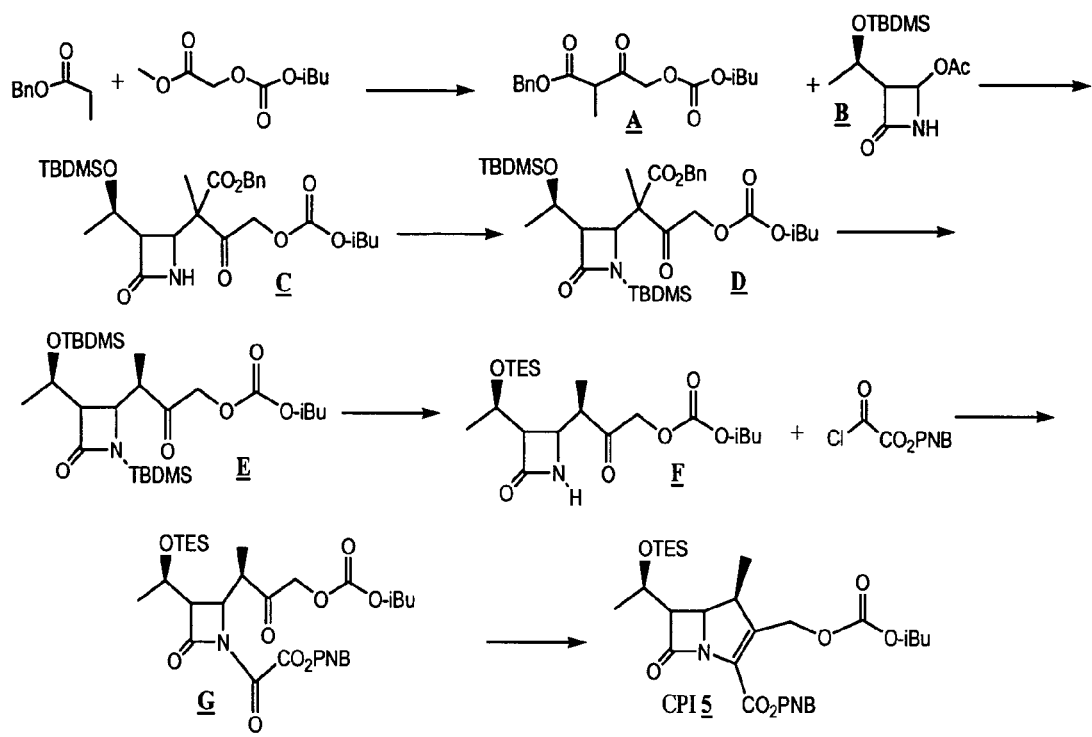

Figure 4

TABLE 1: Gram-Negative MIC (In Vitro Susceptibility) Data

| NO | Genus | Spieces | 9 | 12 | 15 | 18 | 21 | 23 | 25 | 30 | 32 | 34 | 36 | 39 | 62 | 63 | Meropenem |
|---|---|---|---|---|---|---|---|---|---|---|---|---|---|---|---|---|---|
| 18 | Acinetobacter | calcoaceticus | 4 | 0.5 | 0.5 | 0.25 | 2 | 4 | 0.25 | 1 | 0.5 | 0.5 | 0.5 | 0.5 | 0.5 | 8 | 0.5 |
| 19 | Acinetobacter | baumanii | 2 | 0.5 | 0.5 | 1 | 2 | 2 | 1 | 2 | 0.5 | 2 | 2 | 0.5 | 2 | 32 | 1 |
| 20 | Acinetobacter<sup>ImpR</sup> | baumanii | 4 | 4 | 2 | 2 | 8 | 8 | 2 | 4 | 4 | 8 | 8 | 2 | 4 | 32 | 8 |
| 21 | Citrobacter | diversus | 0.13 | 0.063 | 0.063 | 0.13 | 0.5 | 0.125 | 0.25 | 0.5 | 0.031 | 0.5 | 0.25 | 0.016 | 0.25 | 1 | 0.016 |
| 22 | Citrobacter | freundii | 0.13 | 0.063 | 0.063 | 0.25 | 0.5 | 0.125 | 0.25 | 0.5 | 0.031 | 0.5 | 0.5 | 0.031 | 0.25 | 1 | 0.016 |
| 23 | Enterobacter | aerogenes | 0.5 | 0.25 | 0.25 | 2 | 2 | 0.5 | 1 | 2 | 0.25 | 2 | 1 | 0.25 | 2 | 4 | 0.063 |
| 24 | Enterobacter<sup>B+</sup> | cloacae | 0.13 | 0.063 | 0.031 | 0.13 | 0.5 | 0.125 | 0.125 | 0.5 | 0.016 | 0.5 | 0.5 | 0.031 | 0.25 | 1 | 0.031 |
| 25 | Escherichia | coli | 0.063 | 0.063 | 0.031 | 0.13 | 0.5 | 0.125 | 0.125 | 0.5 | 0.016 | 0.5 | 0.25 | 0.016 | 0.125 | 1 | 0.016 |
| 26 | Escherichia<sup>AmpC+</sup> | coli | 0.063 | 0.063 | 0.031 | 0.063 | 0.25 | 0.125 | 0.25 | 0.25 | 0.016 | 0.5 | 0.25 | 0.016 | 0.125 | 1 | 0.016 |
| 27 | Escherichi<sup>MUT(I22)</sup> | coli | 0.063 | 0.063 | 0.063 | 0.13 | 0.5 | 0.125 | 0.25 | 0.25 | 0.016 | 0.5 | 0.25 | 0.016 | 0.125 | 1 | 0.016 |
| 28 | Klebsiella | oxytoca | 0.13 | 0.125 | 0.125 | 0.5 | 1 | 0.25 | 0.5 | 1 | 0.063 | 1 | 1 | 0.063 | 0.5 | 2 | 0.031 |
| 29 | Klebsiella | pneumoniae | 0.13 | 0.25 | 0.125 | 1 | 1 | 0.25 | 0.5 | 1 | 0.125 | 1 | 1 | 0.063 | 0.5 | 2 | 0.063 |
| 30 | Moraxella | catarrhalis | <=0.008 | <=0.008 | <=0.008 | <=0.008 | 0.031 | <=0.008 | <=0.008 | 0.031 | <=0.008 | <=0.008 | <=0.008 | <=0.008 | <=0.008 | 0.016 | <=0.008 |
| 31 | Morganella | Morganii | 1 | 1 | 0.5 | 8 | 8 | 2 | 8 | 16 | 2 | 2 | 2 | 1 | 8 | 16 | 0.125 |
| 32 | Proteus | vulgaris | 1 | 0.5 | 0.25 | 4 | 4 | 1 | 1 | 2 | 0.25 | 1 | 1 | 0.25 | 2 | 8 | 0.125 |
| 33 | Proteus | mirabilis | 0.25 | 0.125 | 0.063 | 2 | 1 | 0.25 | 0.5 | 0.5 | 0.25 | 0.5 | 0.5 | 0.25 | 0.25 | 2 | 0.031 |
| 34 | Providencia | rettgeri | 0.25 | 0.25 | 0.25 | 1 | 4 | 0.5 | 1 | 2 | 0.25 | 2 | 1 | 0.125 | 1 | 8 | 0.063 |
| 35 | Salmonella | typhimurium | 0.13 | 0.125 | 0.063 | 1 | 1 | 0.25 | 0.25 | 1 | 0.031 | 1 | 1 | 0.031 | 0.25 | 2 | 0.031 |
| 36 | Serratia | marcescens | 0.25 | 0.25 | 0.125 | 0.5 | 1 | 0.25 | 0.5 | 1 | 0.125 | 1 | 1 | 0.063 | 0.5 | 2 | 0.031 |
| 37 | Shigella | dysenteriae | 0.063 | 0.063 | 0.063 | 0.25 | 1 | 0.125 | 0.25 | 0.5 | 0.031 | 0.5 | 0.5 | 0.031 | 0.25 | 1 | 0.031 |
| 38 | Shigella | sonnei | 0.13 | 0.063 | 0.063 | 0.13 | 0.5 | 0.125 | 0.25 | 0.5 | 0.031 | 0.5 | 0.5 | 0.031 | 0.25 | 2 | 0.016 |
| 39 | Shigella | flexneri | 0.063 | 0.063 | 0.031 | 0.13 | 0.25 | 0.125 | 0.25 | 0.25 | 0.016 | 0.5 | 0.25 | 0.016 | 0.125 | 1 | 0.016 |
| 40 | Stenotrophomonas | maltophilia | 0.5 | 0.25 | 0.125 | 0.25 | 1 | 1 | 0.25 | 1 | 0.25 | 0.5 | 0.25 | 0.25 | 0.5 | 4 | 0.25 |
| 41 | Pseudomonas | aeruginosa | 16 | 4 | 4 | 2 | 8 | 16 | 2 | 8 | 8 | 4 | 8 | 8 | 4 | >32 | 0.5 |
| 42 | Pseudomonas<sup>Ceftazidime</sup> | aeruginosa | 4 | 1 | 1 | 2 | 2 | 2 | 0.5 | 2 | 2 | 2 | 2 | 2 | 2 | 16 | 0.5 |
| 43 | Pseudomonas<sup>Ciprofloxacin</sup> | aeruginosa | 16 | 4 | 2 | 4 | 8 | 8 | 4 | 16 | 8 | 4 | 8 | 8 | 8 | >32 | 0.125 |
| 44 | Pseudomonas<sup>Gentamycin</sup> | aeruginosa | 16 | 4 | 4 | 4 | 8 | 8 | 4 | 16 | 8 | 4 | 8 | 8 | 8 | >32 | 1 |
| 45 | Pseudomonas | aeruginosa | 16 | 4 | 4 | 4 | 16 | 16 | 2 | 8 | 8 | 4 | 8 | 8 | 8 | >32 | 0.5 |
| 46 | Pseudomonas<sup>ImR</sup> | aeruginosa | 64 | 8 | 8 | 8 | 16 | 32 | 4 | 16 | 8 | 8 | 8 | 8 | 16 | >32 | 4 |

Figure 4 (cont.)

TABLE 1, CONTINUED

| No. | Genus | Species | 28 | 42 | 45 | 48 | 51 | 54 | Imipenem |
|---|---|---|---|---|---|---|---|---|---|
| 19 | Escherichia | coli | 0.063 | 0.25 | 0.25 | 0.13 | 0.5 | 1 | 0.13 |
| 20 | Escherichia | coli | 0.25 | 0.25 | 0.25 | 0.5 | 0.5 | 4 | 0.13 |
| 21 | Escherichia | coli | 0.063 | 0.5 | 0.25 | 0.13 | 0.5 | 0.5 | 0.13 |
| 22 | Escherichia | coli | 0.13 | 0.5 | 0.25 | 0.25 | 0.5 | 2 | 0.13 |
| 23 | Escherichia | coli | 0.13 | 0.5 | 0.25 | 0.25 | 0.5 | 4 | 0.13 |
| 24 | Escherichia | coli | 0.25 | 0.5 | 0.25 | 0.25 | 0.5 | 1 | 0.25 |
| 25 | Salmonella | typhimurium | 0.13 | 0.5 | 0.25 | 0.25 | 0.5 | 2 | 0.13 |
| 26 | Klebsiella | pneumoniae | 0.13 | 0.5 | 0.25 | 0.25 | 0.5 | 4 | 0.13 |
| 27 | Klebsiella | aerogenes | 2 | 4 | 1 | 2 | 8 | 8 | 0.13 |
| 28 | Klebsiella | aerogenes | 0.13 | 0.5 | 0.5 | 0.25 | 0.5 | 2 | 0.13 |
| 29 | Proteus | vulgaris | 0.5 | 4 | 2 | 1 | 2 | 16 | 1 |
| 30 | Morganella | morganii | 0.5 | 4 | 1 | 0.5 | 2 | 16 | 1 |
| 31 | Citrobacter | freundii | 0.13 | 0.5 | 0.25 | 0.25 | 0.5 | 0.5 | 0.25 |
| 32 | Citrobacter | diversus | 0.063 | 0.25 | 0.25 | 0.13 | 0.5 | 1 | 0.13 |
| 33 | Enterobacter | cloacae | 0.5 | 2 | 1 | 1 | 2 | 16 | 0.5 |
| 34 | Enterobacter | cloacae | 0.063 | 0.25 | 0.25 | 0.13 | 0.25 | 1 | 0.13 |
| 35 | Serratia | marcescens | 1 | 4 | 1 | 2 | 4 | 32 | 1 |
| 36 | Acinetobacter | calcoaceticus | 8 | 4 | 4 | 4 | 8 | 32 | 0.25 |
| 37 | Moraxella | catarrhalis | ≤0.008 | ≤0.008 | ≤0.008 | ≤0.008 | 0.016 | 0.016 | <0.008 |
| 38 | Moraxella | catarrhalis | 0.063 | 0.063 | 0.063 | 0.063 | 0.13 | 0.13 | 0.031 |
| 39 | Pseudomonas | aeruginosa | 64 | 64 | 64 | 64 | 64 | >64 | 2 |
| 40 | Pseudomonas[OflR] | aeruginosa | >64 | >64 | >64 | >64 | >64 | >64 | 4 |
| 41 | Pseudomonas[CeftaR] | aeruginosa | >64 | >64 | >64 | >64 | >64 | >64 | 8 |
| 42 | Pseudomonas[CiproR] | aeruginosa | >64 | >64 | >64 | >64 | >64 | >64 | 16 |
| 43 | Pseudomonas[GentaR] | aeruginosa | >64 | >64 | >64 | >64 | >64 | >64 | 32 |
| 44 | Pseudomonas[ImR] | aeruginosa | >64 | >64 | >64 | >64 | >64 | >64 | 32 |

CARBAPENEM ANTIBACTERIALS WITH GRAM-NEGATIVE ACTIVITY AND PROCESSES FOR THEIR PREPARATION

CROSS REFERENCE TO RELATED APPLICATIONS

This application claims priority to U.S. Provisional Application No. 60/578,632, filed Jun. 10, 2004.

FIELD OF THE INVENTION

This application provides novel carbapenem compounds and their salts and prodrugs, methods of treatment of gram negative bacterial infections with an effective amount of the compounds and pharmaceutical compositions including the compounds.

DESCRIPTION OF RELATED ART

The worldwide exploitation of antibiotics to treat infectious diseases has grown dramatically over the last forty years. In 1954, two million pounds of antibiotics were produced in the United States. Today, the figure exceeds 50 million pounds. According to the Centers Disease Control (CDC), humans consume 235 million doses of antibiotics annually.

Widespread misuse or overuse of antibiotics has fostered the spread of antibiotic resistance and has contributed to the development of a serious public health problem. Antibiotic resistance occurs when bacteria that cause infection are not killed by the antibiotics taken to stop the infection. The bacteria survive and continue to multiply, causing more harm. For example, the bacterium *Staphylococous aureus* is a major cause of hospital acquired infections that, historically, responded satisfactorily to the antibiotic vancomycin. Recently, however, many strains of *S. aureus* have been found to be resistant to vancomycin. Moreover, the death rate for some communicable diseases such as tuberculosis have started to rise again, in part because of increases in bacterial resistance to antibiotics.

Antibiotics are used therapeutically to treat bacterial infections. Several types of antibiotics, classified according to their mechanism of action, are currently employed. The known types of antibiotics include, e.g. cell wall synthesis inhibitors, cell membrane inhibitors, protein synthesis inhibitors and inhibitors that bind to or affect the synthesis of DNA or RNA.

Cell wall synthesis inhibitors, such as beta lactam antibiotics, generally inhibit some step in the synthesis of bacterial peptidoglycan. Penicillin is generally effective against non-resistant *streptococcus, gonococcus* and *staphylococcus*. *Amoxycillin* and *Ampicillin* have broadened spectra against Gram-negative bacteria. Cephalosporins are generally used as penicillin substitutes, against Gram-negative bacteria and in surgical prophylaxis. Monobactams are generally useful for the treatment of allergic individuals.

Numerous antibiotic agents, suitable for use in the treatment of bacteria-related diseases and disorders, are known and disclosed, e.g. in *The Physician's Desk Reference (PDR)*, Medical Economics Company (Montyale, N.J.), (53rd Ed.), 1999; *Mayo Medical Center Formulary, Unabridged Version*, Mayo Clinic (Rochester, Minn.), January 1998; *Merck Index: An Encyclopedia of Chemicals, Drugs and Biologicals*, (11th Ed.), Merck & Co., Inc. (Rahway, N.J.), 1989; *University of Wisconsin Antimicrobial Use Guide*; *Introduction on the Use of the Antibiotics Guideline, of Specific Antibiotics Classes*, Thomas Jefferson University; and references cited therein.

The first carbapenem to be isolated was thienamycin, shown below, which was isolated from *Streptomyces cattleya* (U.S. Pat. No. 3,950,357) and was shown to have strong antibacterial activity, including potency against *Pseudomonas* spp. and β-lactamase stability (Kahan, J. S., et al., *J. Antibiot.*, 32, pp. 1-12 (1979); Bodey, G. P., et al., *Antimicrob. Agents Chemother.*, 15, pp. 518-521 (1979). The racemic synthesis of thienamycin was reported shortly thereafter by Merck (Johnston, D. B. R., et al., *J. Am. Chem. Soc.*, 100, pp. 313-315 (1978); Bouffard, F. A., et al., *J. Org. Chem.*, 45, 1130-1142 (1980)), as well as an asymmetric total synthesis (Salzmann, T. N., et al., *J. Am. Chem. Soc.* 102, pp. 6161-6163 (1980)). The nucleus and amino-containing side chain of this molecule,

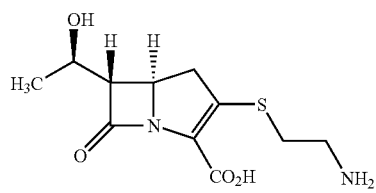

however, contributed to its chemical instability. In addition to its potential to be hydrolyzed by the zinc-activated β-lactamase that is present in *Bacillus* species, *Xanthomonas*, *Pseudomonas*, and *Bacteroides* species (Saino, Y., et al., *Antimicrob. Agents Chemother.*, 22, pp. 564-570 (1982); Yotsujii, A., et al., *Antimicrob. Agents Chemother.*, 24, pp. 925-929 (1983)), chemical stability issues associated with the intermolecular aminolysis of the azetidinone (β-lactam) ring of one molecule of thienamycin by the primary amine in the cysteamine side chain of another thienamycin molecule, resulted in the use of thienamycin as a drug candidate to be abandoned.

As a result of the problems associated with thienamycin, N-formimidoyl thienamycin, known as imipenem, was synthesized (Leanza, W. J., et al., *J. Med. Chem.*, 22, pp. 1435-1436 (1979)). This compound bears a more basic amidine functionality on the 2' side chain, which is protonated at physiological pH, preventing the compound from initiating a nucleophilic attack on another imipenem molecule.

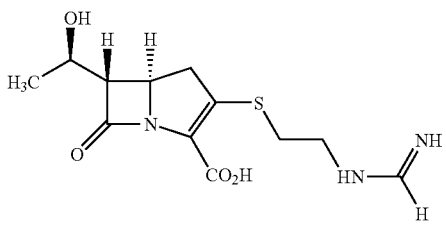

However, poor urinary tract recovery from test subjects revealed an instability of this compound to the mammalian β-lactamase renal dehydropeptidase-I (DHP-I) (Shimada, J., et al., *Drugs Exp Clin Res.*, 20, pp. 241-245 (1994)). Consequently, the compound cilastatin was developed for use in co-administration in order to prevent hydrolysis and degredation by DHP-I; this combination therapy is currently prescribed under the name Primaxin® (Merck Frosst Std).

In response to the problem of carbapenems to destruction by renal dehydropeptidase-1, the carbapenem antibiotic meropenem (SM7338) (shown below), was developed (see, Edwards, J. R., et al., *Antimicrob. Agents Chemother.*, 33, pp. 215-222 (1989); Neu, H. C., et al., *Antimicrob. Agents Chemother.*, 33, pp. 1009-1018 (1989)).

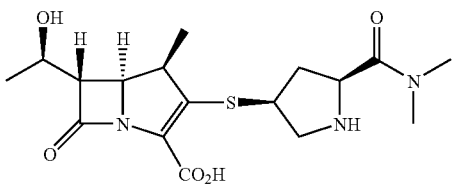

This compound was shown to be active against a large number of Gram-negative bacteria. The drug is currently prescribed for intravenous use (Merrem® IV; AstraZeneca) in the treatment of intra-abdominal infections and bacterial meningitis.

The carbapenem ertapenem (formerly MK-0826; Cunha, B. A., *Drugs of Today*, 38, pp. 195-213 (2002)) was the first of a group of carbapenems with potential against methicillin-resistant staphylococci (MRS) shown to be useful as a long-acting, parenteral carbapenem (Shah, P. M., et al., *J. Antimicrob. Chemother.*, 52, pp. 538-542 (2003); Aldridge, K. E., *Diagn. Microbiol. Infect. Dis.*, 44(2), pp. 181-6 (2002)). It is suitable for administration both as a single-agent (e.g., co-administration with a compound such as cilastatin is not required), or by the intravenous or intramuscular route (Legua, P., et al., *Clin. Therapeut.*, 24, pp. 434-444 (2002); Majumdar, A. K., et al., *Antimicrob. Agents Chemother.*, 46, pp. 3506-3511 (2002)). Eratapenem has received regulatory approval in both the United States (November, 2001) and the European Union (April, 2002).

One carbapenem having a fused pyrazole ring system (L-627; Biapenem) was developed by Lederle Ltd. (Japan), and introduced a methyl radical at the 1-β postion of the carbapenem skeleton (see, U.S. Pat. No. 4,866,171). This structural modification reportedly gave biapenem stability against hydrolysis by kidney dehydropeptidase, making co-administration of a dehydropeptidase inhibitor unnecessary.

More recently, a new, injectable 1-β-methyl carbapenem antibiotic having an (R)-1-hydroxymethyl-methylaminopropyl group exhibiting both broad spectrum, potent antibacterial activity (BO-2727) and having antipseudomonal activity has been reported (Nakagawa, S., et al., *Antimicrob. Agents Chemother.*, 37, pp. 2756-2759 (1993); Hazumi, N., et al., *Antimicrob. Agents Chemother.*, 39, pp. 702-706 (1995

Since the discovery of thienamycin having a potential antimicrobial activity against Gram-negative and Gram-positive bacteria, studies on the syntheses of carbapenem derivatives which are analogous to thienamycin have been widely developed. As a result, it was found that carbapenem derivatives having, as their 2-side chain, a substituent derived from 4-hydroxy-proline exhibit a potential antimicrobial activity and are useful as medicines or as intermediates for compounds possessing antimicrobial activity.

1-β-methyl carbapenem antibiotics, are particularly well known for treating a broad spectrum of gram-negative and gram-positive bacterial infections. See for example U.S. Pat. No. 4,962,103; U.S. Pat. No. 4,933,333; U.S. Pat. No. 4,943,569; U.S. Pat. No. 5,122,604; U.S. Pat. No. 5,034,384 and U.S. Pat. No. 5,011,832.

U.S. Pat. No. 6,255,300 to Merck & Co. describes certain carbapenem antibacterial agents in which the carbapenem nucleus is substituted with an iodo-phenyl linked through a methyl-oxygen lincage. The patent states that these compounds are useful against gram positive bacterial infections. Similarly, U.S. Pat. No. 6,310,055 provides carbapenem compounds with aromatic side chains that are halogen substituted, linked through an alkoxy unsaturated group.

European Publication No. 0 292 191 to Merck & Co. describes certain 2-(substituted methyl)-1-alkylcarbapenem compounds useful as antibiotic agents.

U.S. Pat. No. 6,399,597, also to Merck & Co. describes certain napthosultam compounds that are allegedly useful in the treatment of certain drug resistant bacterial infections.

Because of the difficulty in developing effective carbapenem compounds due to hydrolysis of the β-lactam ring and low recovery, compounds with superior anti-bacterial activity have not been developed.

Therefore, it is one object of the present invention to provide novel β-methylcompounds carbapenems that are effective antimicrobial agents.

It is another object of the present invention to provide methods for the treatment of gram-negative bacteria, that is optionally can be drug-resistant and/or multi-drug resistant.

SUMMARY OF THE INVENTION

In one embodiment of the present invention, carbapenems of the general formula (I)

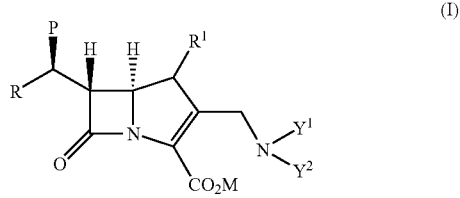

or a pharmaceutically acceptable salt and/or prodrug thereof are described, wherein R is H or alklyl, typically lower alkyl such as $CH_3$;

$R^1$ is H or alkyl, typically lower alkyl such as $CH_3$;

M is H or a group such that $CO_2M$ represents a carboxylic acid, a carboxylate anion, a pharmaceutically acceptable ester group, or a carboxylic acid protected by a protecting group;

P is selected from the group consisting of hydrogen, hydroxyl, halogen (such as F), or hydroxyl protected by a hydroxyl protecting group; and each $Y^1$ and $Y^2$ is independently selected from the group consisting of hydrogen; halo; —CN; —$NO_2$; —$NR^aR^b$; —$OR^c$; —$SR^c$; —C(O)$NR^aR^b$; —C(O)$OR^h$; S(O)$R^c$; —$SO_2R^c$; —$SO_2NR^aR^b$; —$NR^aSO_2R^b$; —C(O)$R^a$; —OC(O)$R^a$; OC(O)$NR^aR^b$; —NRaC(O)$NR^bR^c$; —$NR^aCO_2R^h$; —$OCO_2R^h$; $NR^aC(O)R^b$; $C_{1-6}$ straight- or branched-chain alkyl that are substituted or unsubstituted with one to four $R^d$ groups; $C_{1-6}$ straight- or branched-chain alkyl that are substituted or unsubstituted one to four $R^d$ groups and with or without saturation (double or triple bonds); -A-$(CH_2)_n$-Q and $C_{3-7}$ cycloalkyl, substituted or unsubstituted with one to four $R^d$ groups;

wherein A is selected from the group consisting of O, S, NH, $NCH_3$, NR, or —$CH_2$—;

n is 0, 1, 2 or 3;

each $R^a$, $R^b$ and $R^c$ is independently selected from hydrogen, —$C_{1-6}$ straight- or branched-chain alkyl, unsubstituted or substituted with one to four $R^d$ groups, or —$C_{3-7}$ cycloalkyl, unsubstituted or substituted with one to four $R^d$ groups;

or $R^a$ and $R^b$ taken together with any intervening atoms represent a 4-6 membered saturated ring optionally interrupted by one or more of O, S, $NR^c$, with $R^c$ as defined above, or —C(O)—, said ring being unsubstituted or substituted with one to four $R^i$ groups;

or $R^b$ and $R^c$ taken together with any intervening atoms represent a 4-6 membered saturated ring optionally interrupted by one to three of O, S, $NR^a$, with $R^a$ as defined above, or —C(O)—, said ring being unsubstituted or substituted with one to four $R^i$ groups;

each $R^d$ is independently selected from the group consisting of halogen; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; $NR^eCONR^fR^g$; —$NR^eCO_2R^h$; —$OCO_2R^h$; —$C(NR^e)NR^fR^g$; $NR^eC(NH)NR^fR^g$ or —$NR^eC(NR^f)R^g$;

each $R^e$, $R^f$ and $R^g$ independently represents hydrogen; —R; —$C_{1-6}$ straight- or branched-chain alkyl unsubstituted or substituted with one to four $R^i$ groups;

or $R^e$ and $R^f$ taken together with any intervening atoms represent a 4-6 membered saturated ring optionally interrupted by one to three of O, S, —C(O)— or $NR^g$ with $R^g$ as defined above, said ring being unsubstituted or substituted with one to four $R^i$ groups;

each $R^i$ independently represents halo; —CN; —$NO_2$; phenyl; —$NHSO_2R^h$; —$OR^h$, —$SR^h$; —$N(R^h)_2$; —$N^+(R^h)3$; —$C(O)N(R^h)_2$; $SO_2N(R^h)_2$; heteroaryl; heteroarylium; —$CO_2R^h$; —$C(O)R^h$; —$OCOR^h$; $NHCOR^h$; guanidinyl; carbamimidoyl or ureido;

each $R^h$ independently represents hydrogen, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4-6 membered saturated ring, optionally interrupted by one or two of O, S, $SO_2$, —C(O)—, NH and $NCH_3$;

each Q is selected from the group consisting of:

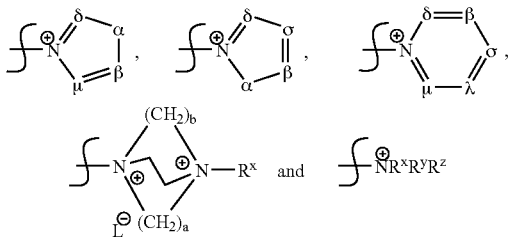

wherein.

a and b are 1, 2 or 3;

$L^-$ is a pharmaceutically acceptable counterion;

α is selected from O, S or $NR^s$;

each β, δ, λ, μ, and σ is independently selected from $CR^t$, N or $N^+R^s$, provided that no more than one of β, δ, λ, μ, and σ is $N^+R^s$;

each $R^s$ is independently selected from hydrogen; phenyl or $C_{1-6}$ straight- or branched-chain alkyl, unsubstituted or substituted with one to four $R^i$ groups;

each $R^t$ is independently selected from hydrogen; halo; phenyl; —CN; —$NO_2$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^u$-$CONR^tR^w$; —$OCO_2R^v$; —$C_{1-6}$ straight- or branched-chain alkyl, unsubstituted or substituted with one to four $R^i$ groups;

each $R^u$ and $R^v$ is independently hydrogen or —$C_{1-6}$ straight- or branched-chain alkyl, unsubstituted or substituted with one to four $R^i$ groups;

or $R^u$ and $R^v$ together with any intervening atoms represent a 4-6 membered saturated ring optionally interrupted by one or more of O, S, NRW or —C(O)—, said ring being unsubstituted or substituted with one to four $R^i$ groups;

each $R^w$ independently represents hydrogen; —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1-4 $R^i$ groups; or $R^h$ and $R^w$ taken together with any intervening atoms represent a 5-6 membered saturated ring, optionally interrupted by one or two of O, S, $SO_2$, NH or $NCH_3$;

each $R^x$ independently represents hydrogen or a $C_{1-8}$ straight- or branched chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

each $R^y$ and $R^z$ is independently selected from hydrogen; phenyl; —$C_{1-6}$ straight or branched chain alkyl, unsubstituted or substituted with one to four $R^i$ groups, and optionally interrupted by O, S, $NR^w$, $N^+R^hR^w$ or —C(O)—;

or $R^x$ and $R^y$ together with any intervening atoms represent a 4-6 membered saturated ring optionally interrupted by O, S, $SO_2$, $NR^w$, $N^+R^hR^w$ or —C(O)—, unsubstituted or substituted with 1-4 $R^i$ groups, and when $R^x$ and $R^y$ together represent a 4-6 membered ring as defined above, $R^z$ is as defined above or $R^z$ represents an additional saturated 4-6 membered ring fused to the ring represented by $R^x$ and $R^y$ taken together, optionally interrupted by O, S, $NR^w$ or —C(O)—, said rings being unsubstituted or substituted with one to four $R^i$ groups.

The present invention also provides a pharmaceutical composition including a compound of the invention, or a pharmaceutically acceptable salt and/or prodrug thereof, optionally with a pharmaceutically acceptable carrier or diluent.

In one embodiment, the invention provides a pharmaceutical composition comprising a compound of the invention, or a pharmaceutically acceptable salt and/or prodrug therein, in combination with one or more other antimicrobial agents, optionally with a pharmaceutically acceptable carrier or diluent.

In another embodiment, the invention provides a method of preventing or treating a bacterial infection in a host, typically an animal, and most typically a human, including administering to the host a therapeutic amount of a compound of the present invention, or a pharmaceutically acceptable salt and/or prodrug therein, optionally in a pharmaceutically acceptable carrier or diluent.

In a separate embodiment, the invention provides a method of preventing or treating a gram-negative bacterial infection in a host that includes administering a therapeutic amount of a compound of the present invention, or a pharmaceutically acceptable salt and/or prodrug therein, in combination or alternation with one or more other antimicrobial agents, optionally in a pharmaceutically acceptable carrier or diluent.

In one principal embodiment, the bacterial infection is due to a gram-negative bacteria. In another embodiment, the bacterial infection is from a drug resistant and/or multiple-drug resistant gram-negative bacteria.

The invention also provides a compound of the present invention for use in medical therapy, and the use in the preparation of a medicament for the treatment of bacterial infections, particularly gram negative bacterial infections, alone or in combination with another agent.

DESCRIPTION OF THE FIGURES

FIG. 2 shows a nonlimiting illustrative example of the structure of carbapenem analogs of the present invention possessing gram-negative biological activity.

FIG. 3 shows the synthetic process of preparing carbapenem Intermediate 5.

FIG. 4 is a table showing gram-negative MIC (In Vitro Susceptibility) Data for selected compounds against selected organism.

DETAILED DESCRIPTION OF THE INVENTION

Figure 1:
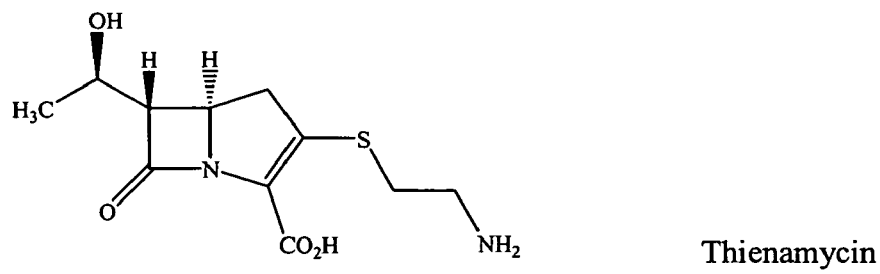
FIG. 1 shows a nonlimiting illustrative example of known carbapenems.
Figure 1:
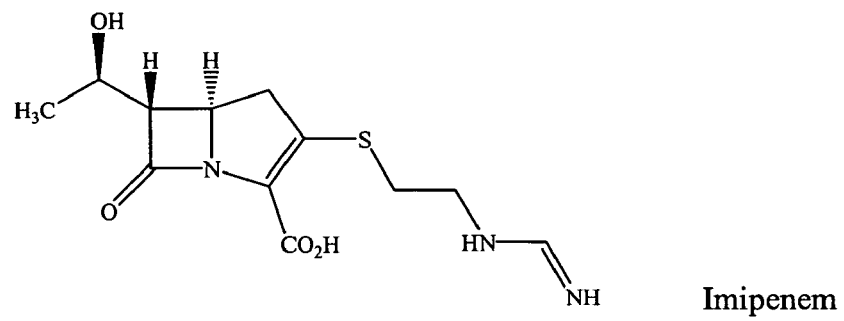
Figure 1:
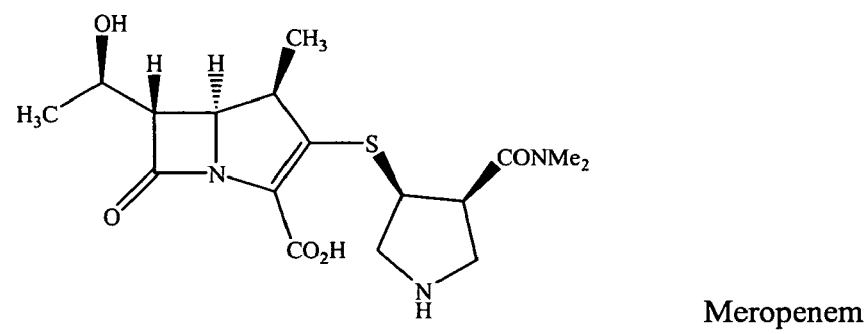
Figure 1:
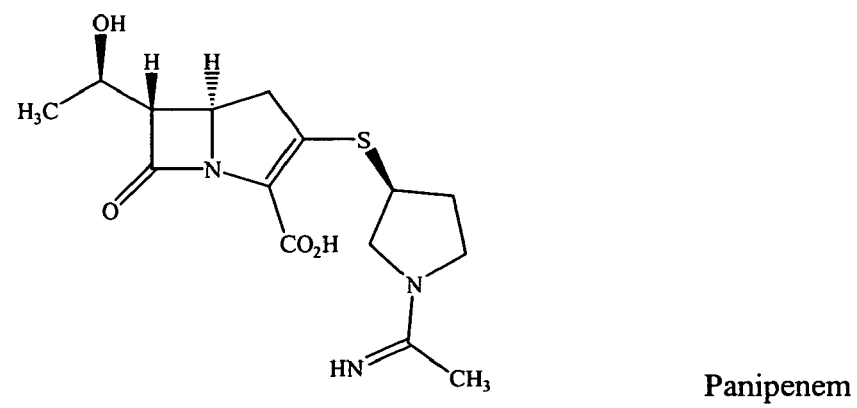
Figure 1:
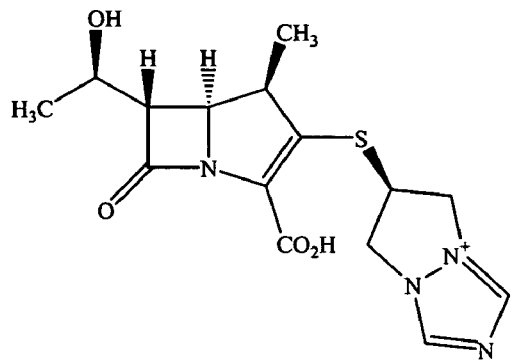
Figure 1:
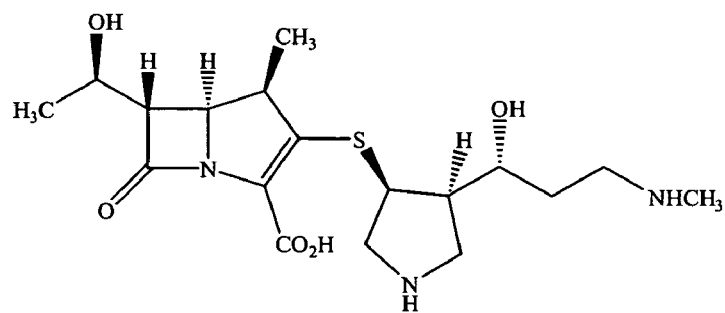
Figure 1:
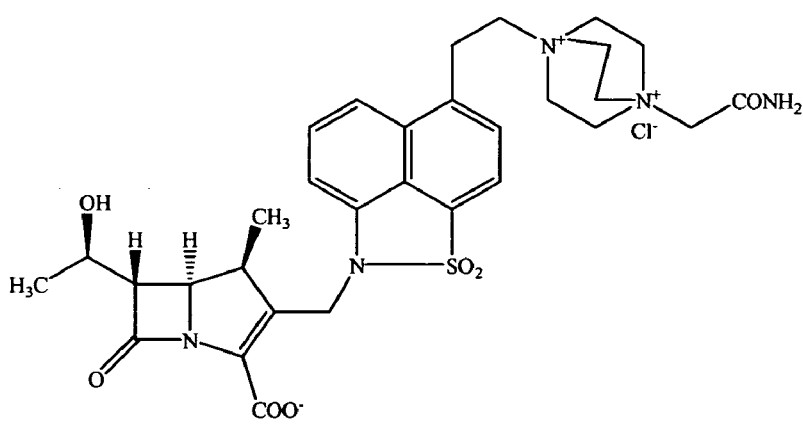
Figure 1:
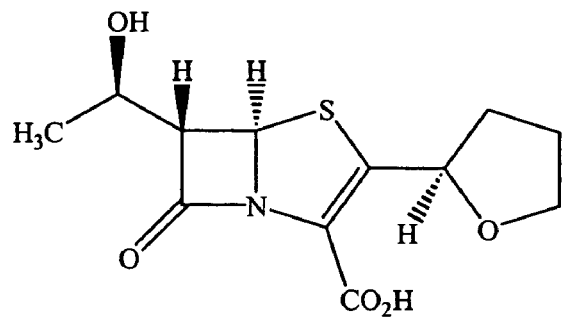
Figure 1:
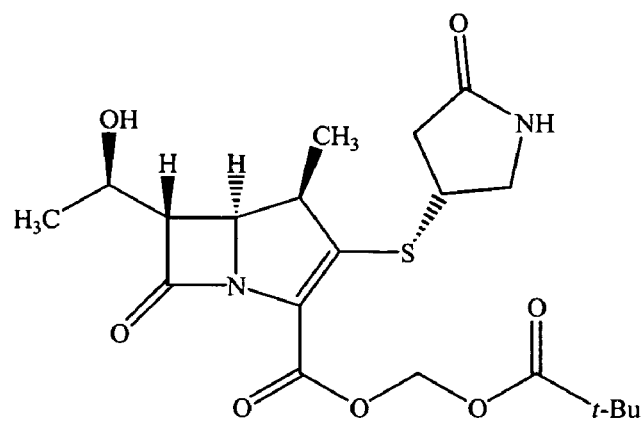
Figure 1:
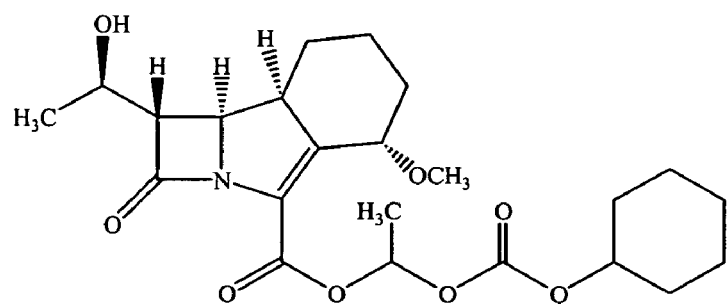

The invention provides carbapenem compounds or their pharmaceutically acceptable salts or prodrugs, pharmaceutical compositions containing these compounds and methods of their use in the treatment or prevention of gram-negative bacterial infections.

Definitions

The numbering system for the carbapenem compounds used in this specification is set out below, wherein the numbering of the carbapenem nucleus is in accordance with standards in the art (see, Tiraby, G., et al., *Biochem J*, 276 (pt. 1), pp. 269-270 (1991)).

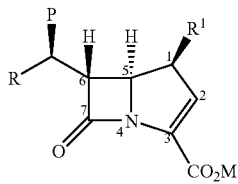

Whenever a range is presented herein it should be understood to include each element of the range. For example, the range "$C_1$ to $C_4$" alkyl independently includes $C_1$, $C_2$, $C_3$ and $C_4$ alkyl groups. When such a range is stated, each element has been contemplated and the range is used merely for convenience.

Generally, while the compounds, compositions and methods are described in terms of "comprising" various components or steps, the compounds, compositions and methods can also "consist essentially of" or "consist of" the various components and steps.

The term "alkyl", as used herein, unless otherwise specified, includes a saturated straight, branched, or cyclic, primary, secondary, or tertiary hydrocarbon of $C_1$ to $C_{10}$. The term includes both substituted and unsubstituted alkyl groups. Moieties with which the alkyl group can be substituted are selected from the group consisting of hydroxyl, halo (F, Cl, Br, I), amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference. When the alkyl group is said to be substituted with an alkyl group, this is used interchangeably with "branched alkyl group". Specific examples of alkyls and/or substituted alkyls includes, but are not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl.

The term "lower alkyl", as used herein, and unless otherwise specified, refers to a $C_1$ to $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is typical. Similarly, when alkyl or lower alkyl is a suitable moiety, unsubstituted alkyl or lower alkyl is typical.

Cycloalkyl is a species of alkyl containing from 3 to 15 carbon atoms, without alternating or resonating double bonds between carbon atoms. It may contain from 1 to 4 rings which are fused.

The term "alkenyl" includes a hydrocarbon radical straight, branched or cyclic containing from 2 to 10 carbon atoms and at least one carbon to carbon double bond. Examples of alkenyl groups include ethenyl, propenyl, butenyl and cyclohexenyl.

The term "alkynyl" refers to a hydrocarbon radical straight or branched, containing from 2 to 10 carbon atoms and at least one carbon to carbon triple bond. Examples of alkynyl groups include ethynyl, propynyl and butynyl.

"Alkoxy" includes $C_1$-$C_4$ alkyl-O—, with the alkyl group optionally substituted as described herein.

The term "alkylamino" or "arylamino" refers to an amino group that has one or two alkyl or aryl substituents, respectively.

"Aryl" refers to aromatic rings e.g., phenyl, substituted phenyl, biphenyl, and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The typical aryl groups are phenyl, naphthyl and phenanthrenyl. The term includes both substituted and unsubstituted moieties. The aryl group can be substituted with one or more moieties selected from the group consisting of bromo, chloro, fluoro, iodo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991. Typical substituted aryls include phenyl and naphthyl.

The term "alkaryl" or "alkylaryl" refers to an alkyl group with an aryl substituent. The term "aralkyl" or "arylalkyl" refers to an aryl group with an alkyl substituent.

The term "heteroaryl" or "heteroaromatic", as used herein, refers to an aromatic group that includes at least one sulfur, oxygen, nitrogen or phosphorus in the aromatic ring. Heteroaryl or heteroaromatic compounds include monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one, two or three additional carbon atoms are optionally replaced by a heteroatom selected from oxygen, sulfur or nitrogen heteroatom. Examples of this type are pyrrole, pyridine, oxazole, thiazole and oxazine. Additional nitrogen atoms may be present together with the first nitrogen and oxygen or sulfur, giving, e.g., thiadiazole. Examples include the following.

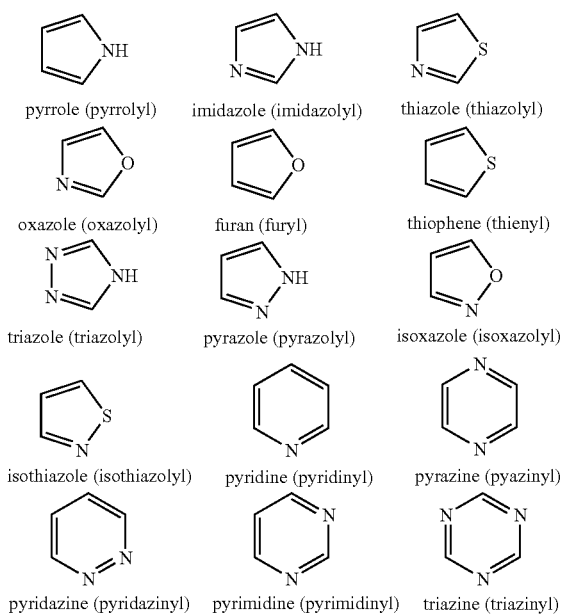

The heteroaryl or heteroaromatic group can be optionally substituted with one or more substituent selected from halogen, haloalkyl, alkyl, alkoxy, hydroxy, carboxyl derivatives, amido, amino, alkylamino, dialkylamino. Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyl-diphenylsilyl, trityl or substituted trityl, alkyl groups, acyl groups such as acetyl and propionyl, methanesulfonyl, and p-toluenylsulfonyl.

"Heteroarylium" refers to heteroaryl groups bearing a quaternary nitrogen atom and thus a positive charge. Examples include the following.

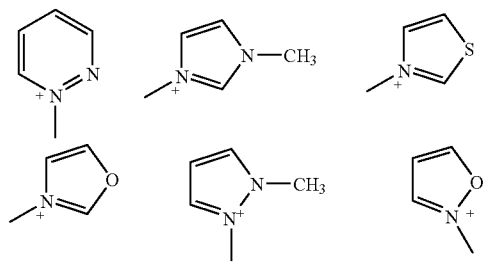

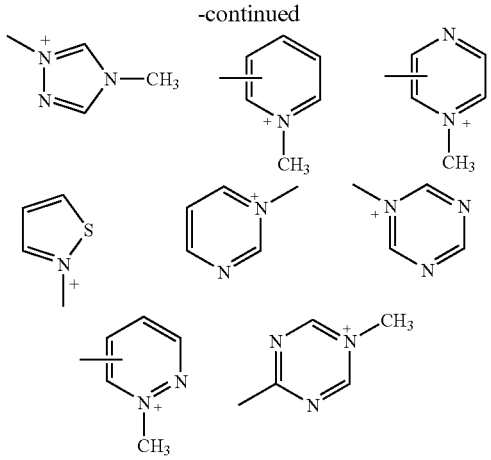

When a charge is shown on a particular nitrogen atom in a ring which contains one or more additional nitrogen atoms, it is understood that the charge may reside on a different nitrogen atom in the ring by virtue of charge resonance that occurs.

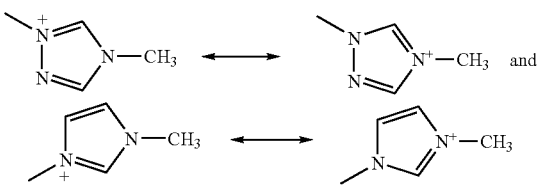

The term "heterocycloalkyl" refers to a cycloalkyl group (nonaromatic) in which one of the carbon atoms in the ring is replaced by a heteroatom selected from O, S or N, and in which up to three additional carbon atoms may be replaced by heteroatoms.

The terms "quaternary nitrogen" and "positive charge" refer to tetravalent, positively charged nitrogen atoms including, e.g., the positively charged nitrogen in a tetraalkylammonium group (e.g. tetramethylammonium), heteroarylium, (e.g., N-methyl-pyridinium), basic nitrogens which are protonated at physiological pH, and the like. Cationic groups thus encompass positively charged nitrogen-containing groups, as well as basic nitrogens which are protonated at physiologic pH.

The term "heteroatom" refers to oxygen, sulfur, nitrogen, phosphorus, and selenium, selected on an independent basis.

Halogen and "halo", as used herein, includes bromine, chlorine, fluorine and iodine.

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters typically include a phenyl group. The term "lower acyl" refers to an acyl group in which the non-carbonyl moiety is lower alkyl.

"Carboxylate anion" refers to a negatively charged group —COO.

"Guanidinyl" refers to the group: H₂NC(NH)NH—.

"Carbamimidoyl" refers to the group: H₂NC(NH)—.

"Ureido" refers to the group: H₂NC(O)NH—.

When a group is "optionally interrupted", this includes one or more of the interrupting moieties in combination, as well as said moieties located at either or both ends of the chain. Thus, it includes terminating the group as well.

When a group is termed "substituted", unless otherwise indicated, this means that the group contains from 1 to 4 substituents thereon. With respect to R, $R^a$, $R^b$ and $R^c$, the substituents available on alkyl groups are selected from the values of $R^d$. Many of the variable groups are optionally substituted with up to four $R^i$ groups. With respect to $R^e$, $R^f$ and $R^g$, when these variables represent substituted alkyl, the substituents available thereon are selected from the values of $R^i$.

When a functional group is termed "protected", this means that the group is in modified form to preclude undesired side reactions at the protected site, and unless otherwise defined refers to a group that is added to an oxygen, nitrogen, or phosphorus atom to prevent its further reaction or for other purposes. In some of the carbapenem compounds of the present invention, M is a readily removable carboxyl protecting group, and/or P represents a hydroxyl which is protected by a hydroxyl protecting group. Such protecting groups are used to protectively block the hydroxyl or carboxyl group during the synthesis procedures and are readily removable by procedures that will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

A wide variety of oxygen and nitrogen protecting groups are known to those skilled in the art of organic synthesis. Suitable protecting groups for the compounds of the present invention will be recognized from the present application taking into account the level of skill in the art, and with reference to standard textbooks, such as Greene, T. W. and Wuts, P. M., *Protective Groups in Organic Synthesis*, 3$^{rd}$ Ed., Wiley, New York (1991). Examples of carboxyl protecting groups include allyl, benzhydryl, 2-naphthylmethyl, benzyl (Bn), silyl such as t-butyldimethylsilyl (TBDMS), phenacyl, p-methoxybenzyl, o-nitrobenzyl, p-methoxyphenyl, p-nitrobenzyl, 4-pyridylmethyl and t-butyl. Examples of suitable C-6 hydroxyethyl protecting groups include triethylsilyl (TES), t-butyldimethylsilyl (TBDMS), o-nitrobenzyloxycarbonyl (ONB), p-nitrobenzyloxycarbonyl (PNB), benzyloxycarbonyl (CBz), allyloxycarbonyl (Alloc), t-butyloxycarbonyl (Boc), 2,2,2-trichloroethyloxycarbonyl (Troc), and the like.

The phrase "pharmaceutically acceptable ester, salt or hydrate," refers to those salts, esters and hydrated forms of the compounds of the present invention which would be apparent to the pharmaceutical chemist. i.e., those which are substantially non-toxic and which may favorably affect the pharmacokinetic properties of said compounds, such as palatability, absorption, distribution, metabolism and excretion. Other factors that are also important in the selection are cost of the raw materials, ease of crystallization, yield, stability, solubility, hygroscopicity and flowability of the resulting bulk drug.

"Pharmaceutically acceptable salts" include salts that retain the desired biological activity of the parent compound and do not impart undesired toxicological effects. These salts can take the form —COOM, where M is a negative charge, which is balanced by a counterion. These include salts formed with cations such as sodium, potassium, NH₄⁺, magnesium, zinc, ammonium, or alkylammonium cations such as tetramethylammonium, tetrabutylammonium, choline, triethylhydroammonium, meglumine, triethanolhydroammonium, calcium, and calcium polyamines such as spermine and spermidine. These can also include salts formed from elemental anions such as chloride, bromide, and iodide. They can also include acid addition salts, for example, salts derived from inorganic or organic acids. Included among such salts are the following: acetate, adipate, alginate, ascorbic acid, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, gluconic acid, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitric acid, oxalate, palmitic acid, pamoate, pectinate, persulfate, 3-phenylpropionate, phosphoric acid, picrate, pivalate, polygalacturonic acid; polyglutamic acid, propionate, p-toluenesulfonic acid, succinate, sulfuric acid, tannic acid, tartrate, thiocyanate, tosylate and undecanoate.

The term "prodrug" includes a compound that, when administered to an animal, is converted under physiological conditions to a compound of the invention, for example a pharmaceutically acceptable ester.

The pharmaceutically acceptable esters are such as would be readily apparent to a medicinal chemist, and include, for example, those described in detail in U.S. Pat. No. 4,309,438. Included within such pharmaceutically acceptable esters are those which are hydrolyzed under physiological conditions, such as pivaloyloxymethyl, acetoxymethyl, phthalidyl, indanyl and methoxymethyl. These are also referred to as "biolabile esters", which are biologically hydrolysable. Examples of biolabile esters include compounds in which M represents an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. These groups can be substituted in the alkyl or aryl portions thereof with acyl or halo groups. The following M species are examples of biolabile ester forming moieties: acetoxymethyl, 1-acetoxyethyl, 1-acetoxypropyl, pivaloyloxymethyl, 1isopropyloxycarbonyloxyethyl, 1-cyclohexyloxycarbonyloxyethyl, phthalidyl and (2-oxo methyl-1,3-dioxolenyl)methyl.

The term "host", as used herein, refers to a unicellular or multicellular organism in which the bacteria can replicate, including cell lines and animals. Alternatively, the host can be carrying a part of the bacterial particles, whose replication and/or function can be altered by the compounds of the present invention. The term host refers to infected cells, cells transfected with all or part of the bacteria and animals, such as, primates (including chimpanzees) and, in one embodiment, the host is a human. Veterinary applications are also encompassed by the present invention.

The term "treatment" as used herein, includes an approach for obtaining beneficial or desired results including clinical results, including alleviation of symptoms, diminishment of extent of disease, stabilization (i.e., not worsening) state of disease, preventing spread of disease, preventing or reducing occurrence or recurrence of disease, delay or slowing of disease progression, and reduction of incidence of disease or symptoms. As used herein, the phrase "anti-bacterially effective amount" means an amount effective for treating the bacterial infection.

Compounds of the Invention

In one embodiment of the present invention, the carbapenem of the formula I,

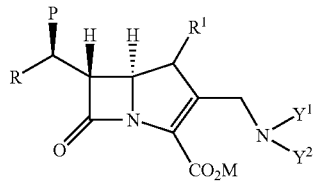

(I)

or pharmaceutically acceptable salts and/or prodrugs thereof is provided, wherein
R is H or alklyl, such as lower alkyl such as $CH_3$;
$R^1$ is H or alkyl, such as lower alkyl such as $CH_3$;
M is H or a group such that $CO_2M$ represents a carboxylic acid, a carboxylate anion, a pharmaceutically acceptable ester group, or a carboxylic acid protected by a protecting group;
P is hydrogen, hydroxyl, halogen such as F, or hydroxyl protected by a hydroxyl protecting group; and
$Y^1$ and $Y^2$ are each independently selected from the following: hydrogen; halo; —CN; —$NO_2$; —$NR^aR^b$; —$OR^c$; —$SR^c$; —$C(O)NR^aR^b$; —$C(O)OR^h$; $S(O)R^c$; —$SO_2R^c$; —$SO_2NR^aR^b$; —$NR^aSO_2R^b$; —$C(O)R^a$; —$OC(O)R^a$; $OC(O)NR^aR^b$; —$NR^aC(O)NR^bR^c$; —$NR^aCO_2R^h$; —$OCO_2R^h$; $NR^aC(O)R^b$; $C_{1-6}$ straight- or branched-chain alkyl that are substituted or unsubstituted with one to four $R^d$ groups and with or without saturation (double or triple bonds); alkylaryl, -A-$(CH_2)_n$-Q and $C_{3-7}$ cycloalkyl, substituted or unsubstituted with one to four $R^d$ groups.
wherein A represents O, S, NH, $NCH_3$, NR, or —$CH_2$—;
n represents an integer 0, 1, 2 or 3;
each $R^a$, $R^b$ and $R^c$ independently represents hydrogen, —$C_{1-6}$ straight- or branched-chain alkyl, unsubstituted or substituted with one to four $R^d$ groups, or —$C_{3-7}$ cycloalkyl, unsubstituted or substituted with one to four $R^d$ groups;
or $R^a$ and $R^b$ taken together with any intervening atoms represent a 4-6 membered saturated ring optionally interrupted by one or more of O, S, $NR^c$, with $R^c$ as defined above, or —C(O)—, said ring being unsubstituted or substituted with one to four $R^i$ groups;
or $R^b$ and $R^c$ taken together with any intervening atoms represent a 4-6 membered saturated ring optionally interrupted by one to three of O, S, $NR^a$, with $R^a$ as defined above, or —C(O)—, said ring being unsubstituted or substituted with one to four $R^i$ groups;
each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; $NR^e$-$CONR^fR^g$; —$NR^eCO_2R^h$; —$OCO_2R^h$; —$C(NR^e)NR^fR^g$; $NR^eC(NH)NR^fR^g$ or —$NR^eC(NR^f)R^g$;
each $R^e$, $R^f$ and $R^g$ independently represents hydrogen; —$R^h$; —$C_{1-6}$ straight- or branched-chain alkyl unsubstituted or substituted with one to four $R^i$ groups;

or $R^e$ and $R^f$ taken together with any intervening atoms represent a 4-6 membered saturated ring optionally interrupted by one to three of O, S, —C(O)— or $NR^g$ with $R^g$ as defined above, said ring being unsubstituted or substituted with one to four $R^i$ groups;
each $R^i$ independently represents halo; —CN; —$NO_2$; phenyl; —$NHSO_2R^h$; —$OR^h$, —$SR^h$; —$N(R^h)_2$; —$N^+(R^h)3$; —$C(O)N(R^h)_2$; $SO_2N(R^h)_2$; heteroaryl; heteroarylium; —$CO_2R^h$; —$C(O)R^h$; —$OCOR^h$; $NHCOR^h$; guanidinyl; carbamimidoyl or ureido;
each $R^h$ independently represents hydrogen, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4-6 membered saturated ring, optionally interrupted by one or two of O, S, $SO_2$, —C(O)—, NH and $NCH_3$;
Q is selected from the group consisting of:

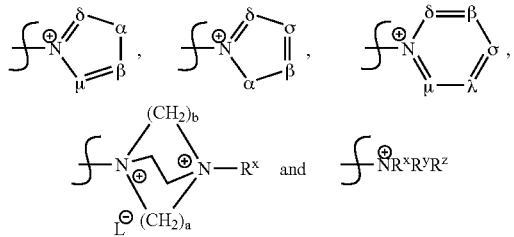

wherein.
a and b are 1, 2 or 3;
$L^-$ is a pharmaceutically acceptable counterion;
α represents O, S or $NR^s$;
β, δ, λ, μ, and σ represent $CR^t$, N or $N^+R^s$, provided that no more than one of β, δ, λ, μ, and σ is $N^+R^s$;
each $R^s$ independently represents hydrogen; phenyl or $C_{1-6}$ straight- or branched-chain alkyl, unsubstituted or substituted with one to four $R^i$ groups;
each $R^t$ independently represents hydrogen; halo; phenyl; —CN; —$NO_2$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; —$C_{1-6}$ straight- or branched-chain alkyl, unsubstituted or substituted with one to four $R^i$ groups;
$R^u$ and $R^v$ represent hydrogen or —$C_{1-6}$ straight- or branched-chain alkyl, unsubstituted or substituted with one to four $R^i$ groups;
or $R^u$ and $R^v$ together with any intervening atoms represent a 4-6 membered saturated ring optionally interrupted by one or more of O, S, NRW or —C(O)—, said ring being unsubstituted or substituted with one to four $R^i$ groups;
each $R^w$ independently represents hydrogen; —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1-4 $R^i$ groups; or $R^h$ and $R^w$ taken together with any intervening atoms represent a 5-6 membered saturated ring, optionally interrupted by one or two of O, S, $SO_2$, NH or $NCH_3$;
$R^x$ represents hydrogen or a $C_{1-8}$ straight- or branched chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

$R^y$ and $R^z$ represent hydrogen; phenyl; —$C_{1-6}$ straight or branched chain alkyl, unsubstituted or substituted with one to four $R^i$ groups, and optionally interrupted by O, S, $NR^w$, $N^+R^hR^w$ or —C(O)—;

or $R^x$ and $R^y$ together with any intervening atoms represent a 4-6 membered saturated ring optionally interrupted by O, S, $SO_2$, $NR^w$, $N^+R^hR^w$ or —C(O)—, unsubstituted or substituted with 1-4 $R^i$ groups, and when $R^x$ and $R^y$ together represent a 4-6 membered ring as defined above, $R^z$ is as defined above or $R^z$ represents an additional saturated 4-6 membered ring fused to the ring represented by $R^x$ and $R^y$ taken together, optionally interrupted by O, S, $NR^w$ or —C(O)—, said rings being unsubstituted or substituted with one to four $R^i$ groups.

In one sub-embodiment, of Formula I,

R is lower alkyl;

$R^1$ is lower alkyl;

M is H or a group such that $CO_2M$ represents a carboxylic acid protected by a protecting group;

P is hydroxyl or hydroxyl protected by a hydroxyl protecting group;

$Y^1$ is $C_{1-6}$ straight- or branched-chain alkyl that are substituted or unsubstituted with one to four $R^d$ groups and with or without saturation (double or triple bonds); and $Y^2$ is independently selected from —CN; —$NR^aR^b$; —C(O)$NR^aR^b$; —C(O)$OR^h$; —$NR^aSO_2R^b$; —C(O)$R^a$ and -A-$(CH_2)_n$-Q;

wherein A represents —$CH_2$—;

n represents an integer 0, 1, 2 or 3;

each $R^a$ and $R^b$ independently represent hydrogen, —$C_{1-6}$ straight- or branched-chain alkyl, unsubstituted or substituted with one to four $R^d$ groups, or —$C_{3-7}$ cycloalkyl, unsubstituted or substituted with one to four $R^d$ groups; or $R^a$ and $R^b$ taken together with any intervening atoms represent a 4-6 membered saturated ring optionally interrupted by one or more of O, S, $NR^c$, with $R^c$ as defined above, or —C(O)—, said ring being unsubstituted or substituted with one to four $R^i$ groups;

each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$1 $NR^e$-$CON^fR^g$; —$NR^eCO_2R^h$; —$OCO_2R^h$; —$C(NR^e)R^fR^g$; $NR^eC(NH)NR^fR^g$ or —$NR^eC(NR^f)R^g$;

each $R^e$, $R^f$ and $R^g$ independently represents hydrogen; —$R^h$; —$C_{1-6}$ straight- or branched-chain alkyl unsubstituted or substituted with one to four $R^i$ groups;

each $R^i$ independently represents halo; —CN; —$NO_2$; phenyl; —$NHSO_2R^h$; —$OR^h$, —$SR^h$; —$N(R^h)_2$; —$N^+(R^h)3$; —$C(O)N(R^h)_2$; $SO_2N(R^h)_2$; heteroaryl; heteroarylium; —$CO_2R^h$; —$C(O)R^h$; —$OCOR^h$; $NHCOR^h$; guanidinyl; carbamimidoyl or ureido;

each $R^h$ independently represents hydrogen, a —$C_{1-6}$ straight or branched alkyl group, a —$C_3$-$C_6$ cycloalkyl group or phenyl, or when two $R^h$ groups are present, said $R^h$ groups may be taken in combination and represent a 4-6 membered saturated ring, optionally interrupted by one or two of O, S, $SO_2$, —C(O)—, NH and $NCH_3$;

Q is selected from the group consisting of:

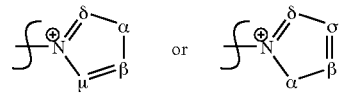

wherein.

a and b are 1, 2 or 3;

$L^-$ is a pharmaceutically acceptable counterion;

α represents O, S or $NR^s$;

β, δ, λ, μ, and σ represent $CR^t$, N or $N^+R^s$, provided that no more than one of β, δ, λ, μ, and σ is $N^+R^s$;

each $R^s$ independently represents hydrogen; phenyl or $C_{1-6}$ straight- or branched-chain alkyl, unsubstituted or substituted with one to four $R^i$ groups;

each $R^t$ independently represents hydrogen; halo; phenyl; —CN; —$NO_2$; —$NR^uR^v$; —$OR^u$; —$SR^u$; —$CONR^uR^v$; $COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; —$C_{1-6}$ straight- or branched-chain alkyl, unsubstituted or substituted with one to four $R^i$ groups;

$R^u$ and $R^v$ represent hydrogen or —$C_{1-6}$ straight- or branched-chain alkyl, unsubstituted or substituted with one to four $R^i$ groups;

each $R^w$ independently represents hydrogen; —$C_{1-6}$ straight- or branched-chain alkyl, unsubstituted or substituted with one to four $R^i$ groups.

In another embodiment, Q is selected from

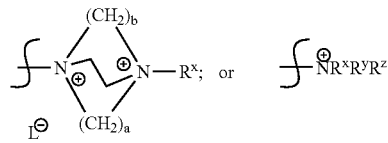

wherein a, b, $L^-$, $R^x$, $R^y$ and $R^z$ are as originally defind.

In one particular embodiment of the present invention, the carbapenem of the formula II,

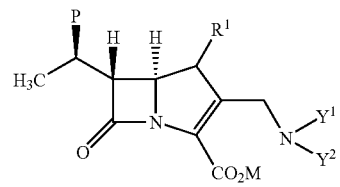

(II)

or pharmaceutically acceptable salts and/or prodrugs thereof is provided, wherein $R^1$ is hydrogen or methyl, P is hydrogen or hydroxyl, and $Y^1$ is H or $R^2$, wherein $R^2$ is H or $C_1$-$C_4$ alkyl and $Y^2$ is —$(CH_2)_n$-A, wherein n=0-4 and A is —CN, —$OR^2$, —$SR^2$, —$N(R^2)_2$, $CO_2R^2$, CO)—$N(R^2)$, —CO)—$NR^2SO_2N(R^2)_2$, $NR^2SO_2N(R^2)_2$, NH—C(=$NR^2$)—N$(R^2)_2$, —S—C(=$NR^2$)—$N(R^2)_2$, wherein each $R^2$ is H or $C_1$-$C_4$ alkyl.

In another particular embodiment of the present invention, the carbapenem of the formula III,

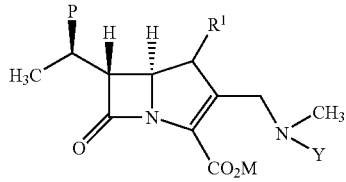
(III)

or pharmaceutically acceptable salts and/or prodrugs thereof is provided, wherein
$R^1$ is hydrogen or methyl,
P is hydrogen or hydroxyl, and
Y is $-(CH_2)_n$-A, wherein n=0-4 and A is $-CN$, $-OR^2$, $-SR^2$, $-N(R^2)_2$, $CO_2R^2$, $C(=O)-N(R^2)$, $-C(=O)-NR^2SO_2N(R^2)_2$, $NR^2SO_2N(R^2)_2$, $NH-C(=NR^2)-N(R^2)_2$, $-S-C(=NR^2)-N(R^2)_2$, wherein each $R^2$ is H or $C_1$-$C_4$ alkyl.

In another particular embodiment of the present invention, the carbapenem of the formula IV,

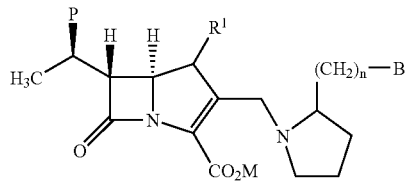
(IV)

or pharmaceutically acceptable salts and/or prodrugs thereof is provided, wherein
$R^1$ is H or methyl,
P is hydrogen or hydroxyl,
n=0-4, and
B is $-OR^2$, $-SR^2$, $-N(R^2)_2$, $CO_2R^2$, $CO-N(R^2)$, $-CO-NR^2SO_2N(R^2)_2$, $NR^2SO_2N(R^2)_2$, $NH-C(=NR^2)-N(R^2)_2$, $-S-C(=NR^2)-N(R^2)_2$, wherein each $R^2$ is H or $C_1$-$C_4$ alkyl, independently.

In one subembodiment of Formula (IV), P' is hydroxyl, $R^1$ is methyl, n=0, 1, and B is $CONH_2$, $-CONHSO_2NH_2$, $NHSO_2NH_2$, $NH-C(=NH)-NH_2$, $-S-C(=NH)-NH_2$.

In another particular embodiment of the present invention, the carbapenem of the formula V,

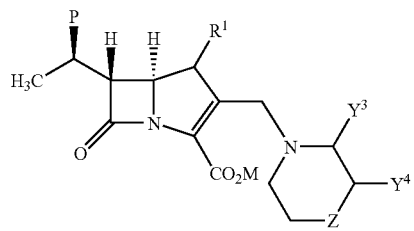
(V)

or pharmaceutically acceptable salts and/or prodrugs thereof is provided, wherein $R^1$ is hydrogen or methyl,
P is hydrogen or hydroxyl,
Z is $-O$, $-S$, $-N(R^2)$, and,
each $Y^3$ and $Y^4$ independently represents hydrogen or $-(CH_2)_n$-A, wherein n=0-4 and A=$-N(R^2)_2$, $-CO_2R^2$, $-CO-N(R^2)_2$, $-CO-NR^2SO_2N(R^2)_2$, $NR^2SO_2N(R^2)_2$, $NH-C(=NR^2)-N(R^2)_2$, $-S-C(=NR^2)-N(R^2)_2$, wherein each $R^2$ is H or $C_1$-$C_4$ alkyl, independently.

In one subembodiment of Formula (V), P' is hydroxyl, $R^1$ is methyl, Z is NH, and, each $Y^3$ and $Y^4$ independently represents hydrogen or $-(CH_2)_n$-A, wherein n=0-2 and A=$-N(R^2)_2$, $-CON(R^2)_2$, $-CO-NHSO_2NH_2$, $NHSO_2NH_2$, wherein $R^2$=hydrogen or methyl.

In certain subembodiments, the compounds of the invention are those compounds shown in FIG. 2.

In certain subembodiments, the compound is compound 9:

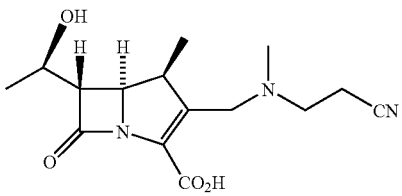
9 or a pharmaceutically acceptable salt or prodrug thereof.

In certain subembodiments, the compound is compound 12:

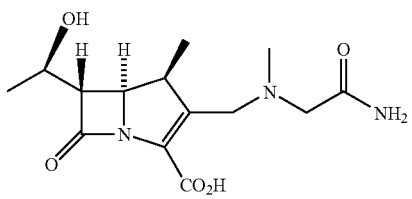
12 or a pharmaceutically acceptable salt or prodrug thereof.

In certain subembodiments, the compound is compound 15:

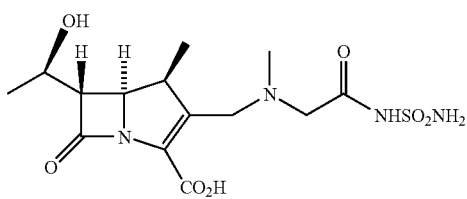
15 or a pharmaceutically acceptable salt or prodrug thereof.

In certain subembodiments, the compound is compound 18:

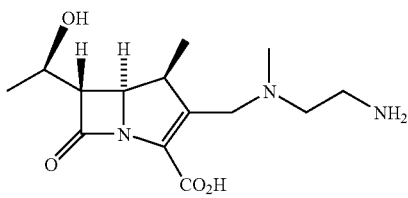

or a pharmaceutically acceptable salt or prodrug thereof.

In certain subembodiments, the compound is compound 21:

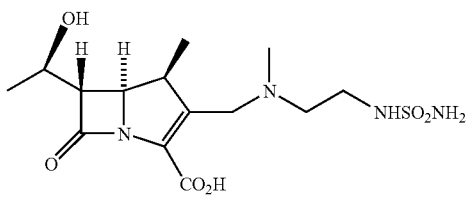

or a pharmaceutically acceptable salt or prodrug thereof.

In certain subembodiments, the compound is compound 25:

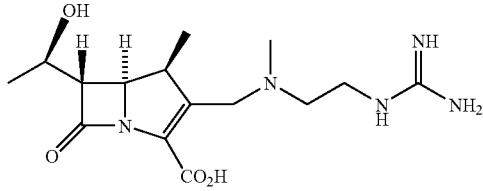

or a pharmaceutically acceptable salt or prodrug thereof.

In certain subembodiments, the compound is compound 28:

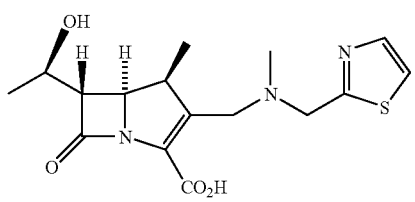

or a pharmaceutically acceptable salt or prodrug thereof.

In certain subembodiments, the compound is compound 32:

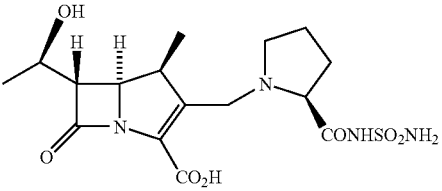

or a pharmaceutically acceptable salt or prodrug thereof.

In certain subembodiments, the compound is compound 34:

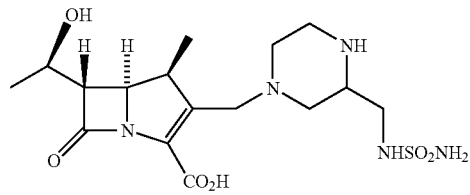

or a pharmaceutically acceptable salt or prodrug thereof.

In certain subembodiments, the compound is compound 36:

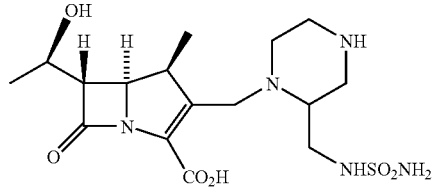

or a pharmaceutically acceptable salt or prodrug thereof.

In certain subembodiments, the compound is compound 39:

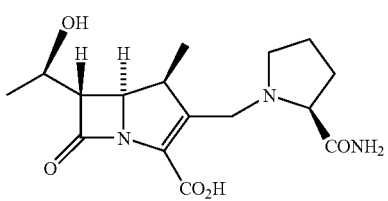

or a pharmaceutically acceptable salt or prodrug thereof.

Process of Making Compounds

The compounds of the present invention can be prepared using the general process outlined in Scheme 1, below, such as from carbapenem intermediate 5 illustrated in FIG. 3. Reagents and substrates used herein can be either purchased, or synthesized according to known procedures.

The present invention also is directed to an efficient synthetic route to β-methyl carbapenems from available precursors with the option of introducing functionality as needed. The process of synthesis is applicable to a wide range of oxygen and nitrogen linkers, as well as other heteroatom linkers, such as sulfur and phosphorus. The carbapenems made according to the present invention can also be used as synthetic intermediates in the preparation of a variety of other β-methyl carbapenem analogs, as well as additional derivatives obtained by subsequent functional group manipulations.

The invention also provides intermediates disclosed herein that are useful in the preparation of compounds of the present invention as well as synthetic methods for preparing the compounds of the invention.

In one embodiment of the invention, the carbapenem intermediate is synthesized using Scheme 1, which is shown in greater detail in FIG. 3.

a) preparing or obtaining a carbapenem intermediate of the structure (A), for example using the process of Scheme 1

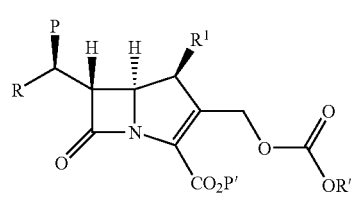

(A)

wherein
P, R and $R^1$ are as defined above;
P' is a suitable carboxyl protecting group; and
R' is an alkyl or substituted alkyl; and then Scheme 1

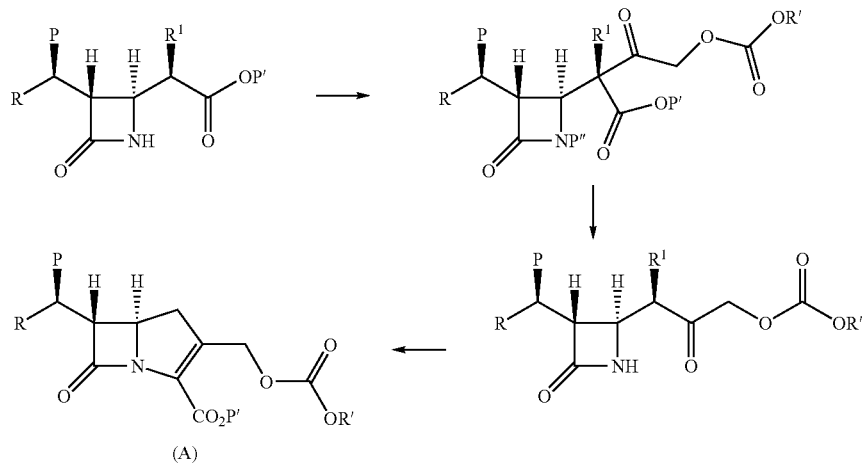

(A)

This carbapenem intermediate, containing an activated —O(CO)$_2$R', wherein R' is an alkyl, such as —O(CO)$_2$(i-Bu), to achieve coupling of the carbapenem to the heteroaromatic side chain, including a oxygen or nitrogen moiety, to produce a β-methyl carbapenem.

In one embodiment, a process for synthesizing a compound represented by formula I.

(I)

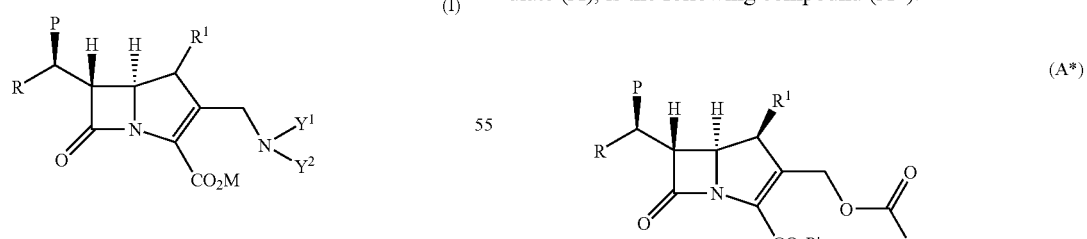

or a pharmaceutically acceptable salt thereof is provided.

The present invention also is directed to methods of efficient synthesis of β-methyl carbapenems from available precursors with the option of introducing functionality as needed. Therefore, in one embodiment, the carbapenems are synthesized using the process of the present invention.

In one embodiment, the method for preparing β-methyl carbapenems includes:

b) coupling the compound of structure (A) with a moiety with a free hydroxyl, such as an aromatic alcohol or a heteroaromatic alcohol, or a mono- or di-substituted amine, such as a aromatic amine or heteroaromatic amine, to obtain an β-methyl carbapenem; and then c) optionally deprotecting the β-methyl carbapenem, if necessary.

In one illustrative embodiment, the carbapenem intermediate (A), is the following compound (A*).

(A*)

The selection of reaction conditions should take into account the ease of substitution of the —O(CO$_2$)R in the carbapenem intermediate to form the desired carbapenem.

The process of synthesis is applicable to a wide range of oxygen and nitrogen linkers, as well as other heteroatom linkers, such as sulfur and phosphorus. The carbapenems made according to the present invention can also be used as synthetic intermediates in the preparation of a variety of other β-methyl carbapenem analogs, as well as additional derivatives obtained by subsequent functional group manipulations.

The invention also provides intermediates disclosed herein that are useful in the preparation of compounds of the present invention as well as synthetic methods for preparing the compounds of the invention.

Suitable solvents for carrying out the processes of the present disclosure are inert organic solvents, including but are not limited to, alcohols, aldehydes, amides, ethers, esters, halogenated solvents, hydrocarbons, glycols and glycol ethers, ketones, nitriles, and numerous other solvents common in chemical processes, as well as mixtures of such solvents. These inert solvents can be used alone or in combination, and can be miscible or immiscible with each other, with the proviso only that the compounds of interest are at least partially soluble in the solvent or solvents used. In the instance of using an immiscible, or 2-phase, solvent system, the process can also include the addition of a phase-transfer agent. Suitable phase-transfer agents are known in the art, such as those described in Sasson, et al., *Handbook of Phase Transfer Catalysis*, Kluwer Academic Publishers, 1997.

In one embodiment, the solvent is DMF, the reaction is carried out at about room temperature, using 5 mol eq. of $Pd_2dba_3$*$CHCl_3$ (tris(dibenylideneaceton)-dipalladium(0)-chloroform adduct), 30 mol eq. of either $P(OEt)_3$, no acid or base. In certain cases, 0.5 eq. 2,6-lutidine can be added to increase the rate of reaction. In certain embodiments, 0.5 eq. PTSA are added.

In one embodiment, the reaction is run with dppb (1,4-bis(diphenylphosphine)butane) or triethyl phosphate.

In one embodiment, the reaction is run in the absence of a base. In another embodiment, the reaction is carried out (run) in the absence of an acid. In a separate embodiment the reaction is carried out in 2,6-lutidine or p-toluenesulfonic acid monohydrate.

For the purpose of the present invention, the inert organic solvents suitable for use in preparing the compounds described and claimed herein include but are not limited to aromatic solvents, such as benzene, toluene, chloro benzene, styrene, tetraline, biphenyl, and xylenes; ether solvents, such as diethyl ether, n-butyl ether, methyl tert-butyl ether, tetrahydrofuran (THF), and 1,4-dioxane; halogenated solvents, such as chloroform, bromoform, carbon tetrachloride, dichloromethane, dichloroethane, trichloroethane, dichlorobenzne, and chlorobenzene; alcohols, including $C_1$-$C_{10}$ alkanols, which can be linear, branched, or cyclic, and may be saturated or unsaturated, including methanol, ethanol, 2-propanol, butanol and hexanol; $C_1$-$C_{10}$ hydrocarbon solvents, which can be linear, branched, or cyclic, and may be saturated or unsatured, including hexane, heptane, cyclohexane, cyclohexene, and pentane; ester and ketone solvents, such as acetone, ethyl acetate, isopropyl acetate, methylbutyl ketone (2-hexanone), methyl ethyl ketone (MEK), methylisobutyl ketone (MIBK), methyl n-butyl ketone (MBK), methyl isopropyl ketone, and cyclohexanone; and nitrogen-containing solvents, including acetonitrile, nitromethane, N,N-dimethylformamide (DMF), dimethylacetamide (DMA), hexamethylphosphoramide (HMPA), N-methylpyrrolidinone (NMP), N,N'-dimethylpropylene urea (DMPU), 1,3-dimethyl-2-oxohexahydropyrimidine, and N-ethylpyrrolidinone.

Bases suitable for use in conducting certain of the synthetic transformations described and claimed herein include but are not limited to carbonates, including alkali metal carbonates and bicarbonates, such as sodium carbonate, sodium bicarbonate, potassium carbonate, rubidium carbonate, and cesium carbonate; alkaline earth metal carbonates, such as magnesium carbonate, calcium carbonate, and strontium carbonate; hydroxides, such as sodium hydroxide and potassium hydroxide; and transition metal bases, such as zinc hydroxide. Also suitable for use as bases in the transformations described herein are organic bases, including but not limited to triethylamine (TEA); diethylamine; diisopropylamine; N,N-diisopropylethylamine (DIPEA or DIEA, also known as Hunig's base); dimethylamine; benzylamine; 4-dimethylaminopyridine (DMAP); ureas, such as tetramethylurea (TMU); pyridine; 2,6-lutidine; imidazole; pyrrole; diphenylamine; tri-n-propylamine; cyclohexylamine; triphenylamine; pyrrolidine; ureas, such as tetramethylurea (TMU); and piperidine.

As defined above, when a functional group is termed to be "protected" with a "protecting group" (herein represented by the letter designation, P), this means that the group is chemically modified to preclude undesired side reactions at the protected site. Suitable compounds for use with the compounds of the present invention will be recognized from the present application, and include those included in such standard reference texts known to those of skill in the art as Greene, T. W. and Wuts, P. G. M., "Protective Groups in Organic Synthesis, Third Edition", Wiley Interscience, New York (1999). Examples of suitable protecting groups include but are not limited to silyl protecting groups, including tri-$C_{1-6}$ alkyl silyl groups (e.g., trimethylsilyl and triethylsilyl), diphenyl siloxy groups (e.g., t-butyldiphenylsilyl (TBDPS)), $C_{1-6}$ alkyl silyloxy groups (e.g., tert-butyldimethylsilyl (TBDMS)), substituted and unsubstituted benzyl groups (e.g., benzyl, benzyloxycarbonyl, o-nitrobenzyloxycarbonyl, p-nitrobenzyloxycarbonyl), carbonyls, such as 2,2,2-trichloroethyloxycarbonyl (Troc), allyloxycarbonyl (Alloc), and fluorenylmethyloxycarbonyl (Fmoc).

The processes of preparing the compounds of the present invention are suitably conducted at a temperature in a range of from about −78° C. to the boiling point of the reaction medium or solvent (e.g., from about −78° C. to about 200° C.), and are typically conducted at a temperature in a range of from about −50° C. to the boiling point of the reaction medium or solvent. In one embodiment, the temperature is in a range of from about −20° C. to the boiling point of the reaction medium or solvent. In another embodiment, the temperature is in the range of from about −10° C. to the boiling point of the reaction medium or solvent.

The reactants used in the presently disclosed process can be added to the reaction vessel (also referred to herein as the reaction "pot", or "round bottom") concurrently, either together or separately, or they can be added sequentially in either order.

Method of Treatment

The present invention also provides a method of preventing or treating a bacterial infection, in a host, for example an animal, and typically a human, including administering a therapeutic amount of a compound of the present invention, or a pharmaceutically acceptable salt and/or prodrug therein, optionally in a pharmaceutically acceptable carrier or diluent where the bacterial infection is due to a gram-negative bacteria. In one embodiment, the bacterial infection is a drug resistant and/or multiple-drug resistant bacterial infection.

The invention also provides a compound of the present invention for use in medical therapy.

The present invention also provides a use of a therapeutic amount of a compound of the present invention, or a pharmaceutically acceptable salt and/or prodrug therein, optionally in a pharmaceutically acceptable carrier or diluent, for preventing or treating a gram-negative bacterial infection, in a host, such as an animal, and typically a human.

The distinctive feature of gram-negative bacteria is the presence of a double membrane surrounding each bacterial cell. Although all bacteria have an inner cell membrane, gram-negative bacteria have a unique outer membrane. This outer membrane excludes certain drugs and antibiotics from penetrating the cell, partially accounting for why gram-negative bacteria are generally more resistant to antibiotics than are gram-positive bacteria. The pathogenic capability of gram-negative bacteria is usually associated with certain components of their cell walls, particularly the lipopolysaccharide (endotoxin) layer. The outer membrane of gram-negative bacteria is rich in lipopolysaccharide. If gram-negative bacteria enter the bloodstream, lipopolysaccharide can trigger a cascade of events, including high fever and a drop in blood pressure. Unlike Gram-positive bacteria, which asuume a violet color in Gram staining, Gram negative bacteria incorporate the counterstain rather than the primary stain. Because the cell wall of Gram(−) bacteria is high in lipid content and low in peptidoglycan content, the primary crystal-violet escapes from the cell when the decolorizer is added. Most enteric (bowel related) illnesses can also be attributed to this group of bacteria.

Examples of gram-negative bacteria include *Aeromonas* sp., *Acinetobacter* sp. such as *Acinetobacter baumannii* (or *A. calcoaceticus*), *Actinobacillus actinomycetemcomitans*, *Bacteroides* sp. such as *Bacteroides fragilis*, *Bartonella*, *Bdellovibrio* spp., *Bordetella pertussis*, *Brucella* sp., *Burkholderia cepacia*, *Burkholderia*, *pseudomallei*, *Campylobacter* sp., *Capnocytophaga* sp., *Cardiobacterium hominis*, *Chlamydia trachomatis*, *Citrobacter* sp., *Eikenella corrodens*, *Enterobacter* sp., *Escherichia coli*, *Francisella tularensis*, *Flavobacterium* sp., *Fusobacterium* sp., *Helicobacter pylori*, *Haemophilus influenzae*, *Haemophilus ducreyi*, *Klebsiella* spp. such as *Klebsiella pneumoniae*, *Kingella kingae*, *Legionella* spp. such as *Legionella pneumophila*, *Moraxella catarrhalis*, *Morganella*, *Neisseria gonorrhoeae*, *Neisseria meningitidis*, *Pasteurella pestis*, *Pasteurella multocida*, *Plesiomonas shigelloides*, *Prevotella* sp., *Proteus* spp., *Providencia*, *Pseudomonas* spp. such as *Pseudomonas aeruginosa*, *Salmonella* spp. such as *Salmonella enteriditis* and *Salmonella typhi*, *Serratia marcescens*, *Shigella* spp., *Vibrio cholerae*, *Vibrio parahaemolyticus*, *Vibrio vulnificus*, *Veillonella* sp., *Xanthomonas maltophilia* or *Stenotrophomonas maltophila*, *Yersinia pestis*, *Yersinia enterocolitica*. Additionally, Some organisms simply tend not to be well differentiated by gram staining, despite any known phylogenetic affiliation with the gram-negatives or gram-positives. *Rickettsia prowazekii*, *Rickettsia rickettsii* and *Treponema pallidum*. Chlamydias are small, gram-negative, peptidoglycan-less cocci that are obligate intracellular parasites of animals. Spirochetes are chemoheterotrophic bacteria whose cells are tightly coiled or resemble a stretched spring with gram-negative-like cell envelopes. Spirochetes include *Spirillum minus*, *Borrelia burgdorferi* (Lyme disease), *Leptospira* spp. (leptospirosis) and *Treponema pallidum* (syphilis). Rickettsias and actinomycetes are also gram-negative pleomorphic bacilli and coccobacilli that are obligate intracellular parasites of eucaryotes transmitted generally by insects and ticks.

The present invention also provides a use of a therapeutic amount of a compound of the present invention, or a pharmaceutically acceptable salt and/or prodrug therein, optionally in a pharmaceutically acceptable carrier or diluent, in the manufacture of a medicament for preventing or treating a gram-negative bacterial infection, in a host, such as an animal, and typically a human.

The invention also includes methods of inhibiting bacterial infection in a host. Inhibition of bacterial replication or treatment of an infection in a cell can be measured by showing a reduction in bacterial replication in a cell to a level lower than the level in an otherwise identical cell, which was not administered the compound of the invention. The reduction can be by about 80%, 85%, 90%, 95%, about 99.9% or more. The level of bacterial replication in a cell can be assessed by any known methods. For example, the level of bacterial replication in a cell can be assessed by evaluating the number of bacterial particles or amount of a bacterial component, such as a bacterial protein, a bacterial enzyme, or bacterial nucleic acid, in the cell or in fluid or debris associated with the cell. The number of infectious bacteria in a cell can be evaluated, for example, in a plaque assay. The level of a bacterial component such as a bacterial protein or enzyme in a cell can be evaluated using standard analytical techniques of protein biochemistry, such as, for example, using an activity assay for a bacterial enzyme, or using Western blotting or quantitative gel electrophoresis for a bacterial protein. Bacterial nucleic acid levels in a cell can be evaluated using standard analytical techniques such as Northern blotting and Southern Blotting or quantitation by polymerase chain reaction (PCR).

Combination and Alternation Therapies

In one embodiment of the invention, one or more therapeutic agents, including particularly antimicrobial agents such as antibiotic agents that are effective against gram negative bacteria, can be used in combination and/or alternation with the compound/composition of the present invention to achieve a additive and/or synergistic therapeutic effect.

The active compounds can be administered in combination, alternation or sequential steps with another anti-bacterial agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. In some embodiments, an anti-bacterial agent that exhibits an $EC_{50}$ of 10-15 µM or less, or typically less than 1-5 µM.

In one particular embodiment, the combination includes a β-lactamase inhibitor, such as clavulanic acid, which has been used as in the delivery of prophylactic amounts of antibiotics in patients. Although Clavulanic acid does have some degree of bacterial activity, its principal role is as a beta-lactamase inhibitor. Clavulanic acid has a similar structure to the beta-lactam antibiotics but binds irreversibly to the beta-lactamase enzymes. Used in combination with the beta-lactam antibiotics, it has become one of the most prescribed antibiotics in the western world prolonging the effective life of antibiotics such as Ampicillin (as in GSK's Augmentin®).

It is possible that drug-resistant variants of bacteria can emerge after prolonged treatment with an anti-bacterial agent. The efficacy of a drug against the bacterial infection can be prolonged, augmented, or restored by administering the compound in combination or alternation with a second, and perhaps third, anti-bacterial agent, for example with a different site of activity than the principle drug. Alternatively, the pharmacokinetics, biodistribution or other parameter of the drug can be altered by such combination or alternation therapy.

Suitable antibiotic agents are disclosed, e.g. in Physician's Desk 30 Reference (PDR), Medical Economics Company (Montvale, N.J.), (53rd Ed.), 1999; Mayo Medical Center Formulary, Unabridged Version, Mayo Clinic (Rochester, Minn.), January 1998; Merck Index An Encyclopedia of Chemicals, Drugs and Biologicals, (11th Ed.), Merck & Co., Inc. (Rahway, N.J.), 1989; University of Wisconsin Antimicrobial Use Guide, http://www.medsch.wisc.edu/clinsci/5amcg/amcg.html; Introduction on the Use of the Antibiotics Guideline, of Specific Antibiotic Classes, Thomas Jefferson University, http://jeffiine.tju.edu/CWIS/OAC/antibiotics_guide/intro.html; and references cited therein.

Nonlimiting examples of agents that can be used in combination or alternation with the compounds of the invention include: aminoglycosides, β-lactam antibiotics, cephalosporius, macrolides, miscellaneous antibiotics, penicillins, tetracyclines, antifungals, antimalarial agents, antituberculosis agents, antibacterials, leprostatics, miscellaneous anti-infectives, quinolones, sulfonamides, urinary anti-infectives, nasal antibiotics, opthalmic antibiotics, opthalmic antibacterials, opthalmicquinalones, opthalmic sulfonamides, skin and mucous membrane antibiotics, skin and mucous membrane antifungals, skin and mucous membrane antibacterials, skin and mucous membrane miscellaneous anti-infectives, skin and mucous membranescabicides and pedulicides, skin and mucous membrane antineoplasts, nitrofurans and oxazolidinones.

Specific compounds include, for example, Amikacin (amikacin sulfate); Craramyein (gentamicin sulfate); Nebcin (tobramycin sulfate); Netromycin (netilmicin sulfate); Streptomycin Sulfate; and TOBI (tobramycin), Azactam (aztreonam); Cefotan (cefotetan); Lorabid (loracarbef); Mefoxin (cefoxitin); Merrem (meropenem); and Primaxin (imipenem and cilastatin for injectable suspension); Ancef (cefazolin); Ceclor (cefaclor); Cedax (ceffibuten); Cefizox (ceffizoxime sodium); Cefobid (cefoperazone sodium); Ceftin (cefuroxime axetil); Cefzil (cefprozil); Ceptaz (ceftazidime); Claforan (cefotaxime); Duricef (cefadroxil monohydrate); Fortaz (ceftazidime); Keflex (cephalexin); Keftab (cephalexin HCl); Kefurox (cefuroxime); Kefzol (cefazolin); Mandol (cefamandole nafate); Maxipime (cefepime HCl); Monocid (cefonicidsodium); Omnicef (cefdinir); Rocephin (ceftriaxone); Suprax (cefixime); Tazicef (ceftazidime); Tazidime (ceftazidime); Vantin (cefpodoxime proxetil); and Zinacef5 (cefuroxime); Biaxin (clarithromycin); Dynabac (dirithromycin); E.E.S. 200 (Erythromycin Ethylsuccinate); E.E.S. 400 (Erythromycin Ethylsuccinate); Ery-Ped 200 (Erythromycin Ethylsuccinate); EryPed 400 (Erythromycin Ethylsuccinate); Ery-Tab (Erythromycin delayed-release tablets); Erythrocin Stearate (Erythromycin stearate); Ilosone (erythromycinestolate); PCE Dispertab (erythromycin particles in tablets); Pediazole (erythromycin ethylsuccinate and sulfisoxazole acetyl for oral suspension); Tao (troleandomycin); Zithromax (azithromycin); and Erythromycin; Cleocin HCl (clindamycin hydrochloride); Cleotin Phosphate (elindamycin phosphate); Coly-Mycin M (colistimethate sodium); and Vancocin HCl (vancomycin hydrochloride); Amoxil (amoxicillin); Augmentin (amoxicillin/clavulanate potassium); Bicillin C-R 900/300 (Penicillin G benzathine and Penicillin G procaine suspension); Bicillin C-R (Penicillin G benzathine and Penicillin G procaine suspension); Bicillin L-A (Penicillin G benzathine suspension); Geoeillin (carbencillin indanyl sodium); Mezlin (sterile mezlocillinsodium); Omnipen (ampicillin); Pen-Vee K (penicillin V potassium); Pfizerpen (penicillin G potassium); Pipracil (piperacillin sodium); Speetrobid (bacampicillin-HCl); Ticar (ticarcillin disodium); Timentin (ticarcillin disodium and clavulanate potassium); Unasyn (ampicillin sodium/sulbactam sodium); Zosyn (piperacillin sodium and tazobactam sodium); and Dicloxacillin Sodium; Achromycin V (tetracycline HCl); Declomycin (demeclo-cycline HCl); Dynacin (minocylcine HCl); Minocin (minocycline hydrochloride); Monodox (Doxycycline monohydrate capsules); Terramycin (oxytetracyline); Vectrin (minocycline hydrochloride); Vibramycin Calcium (doxycycline sodium); Vibramycin Hyclate (doxycycline hyclate); Vibramycin Monohydrate (doxycycline monohydrate); Vibra-Tabs (doxycycline-hydrate); Declomycin (demeclocycline HCl); Vibramycin (doxycycline); Dynacin (Minocyline HCl); Terramycin (oxytetracycline HCl); Achromycin V capsules5 (tetracycline HCl); Linco-mycins; and Cleotin HCl (clindamycin HCl); Abelcet (amphotericin B lipid complex); AmBisome (amphotericin B); Amphotec (amphotericin B cholesterol sulfate-complex); Ancobon (flucytosine); Diflucan (fluconazole); Fulvicin P/Gamma (ultramicrosize griseofulvin); Fulvicin P/G 165 and 330 (ultramicrosize griseofulvin); Grifulvin V (griseofulvin); Gals-PEG (gxiseofulvin ultramicrosize); Lamisil (terbinafine hydrochloride); Nizoral (ketoconazole); Amphotericin B; Lotrimin (clotrimazole); Dapsone tablets (dapsone); Diflucan (fluconazole); Monistat-Derm cream (miconazole); Mycostalin Crc am (nystatin); and Sporanox (itraconazole); Aralen hydrochloride (chloroquine HCl); Aralen phosphate (chloroquine phosphate); Dataprim (pyrimethamine); Ladam (mefloquine HCl); and Plaquenil (hydroxychloroqnine sulfate); Capastat sulfate (capreomycinsulfate); Myambutol (ethambutol hydrochloride); Mycobutin (rifabutin capsules); Nydrazid (isoniazid injection); Paser (aminosalicylic acid); Prifiin (rifapentine); Pyrazinamide tablets (pyrazinamide); Rifadin (rifampin capsules); Rifadin IV (rifampin for injection); Rifamate (rifampin and isoniazid); Rifater (rifampin, isoniazid and pyrazinamide); Seromycin (cycloserine capsules); Streptomycin-Sulfate; Tice BCG (BCG vaccine); Cycloserine (seromycin capsules); Urised (Methenamine); and Trecator-SC (ethionamide tablets); Alferon N (interferon alfa-n3); Crixivan (indinavir sulfate); Cytovene (ganciclovir); Cytovene-IV (ganciclovir sodium); Epivir (lamivudine); Famvir (famciclovir); Flumadine (rimantadine HCl); Foscavir (foscamet sodium); Hivid (zalcitabine); Intron A (interferon alfa-2b); Invirase (saquinavir mesylate); Norvir (ritonavir); Rebetron combination therapy, which contains Rebetrol (ribavirin) and Intron A (inteferon alfa-2b); Rescriptor (delavirdine mesylate); Retrovir (ziduvudine); Retrovir IV (ziduvudine); Symmetrel (amantadine HCl); Synagis (palivizumab); Valtrex (valacyclovir HCl); Videx (didanosine); Viracept (nelfinavir mesylate); Viramune (nevirapine); Virazole (ribavirin); Vistide (cidofovir); Zerit (stavudine (d4T)); Symmetrel Syrup (amantadine HCl); Combivir Tablets (lamiduvine); and Zovirax (acyclovir); Dapsone Tablets (dapsone); Daraprim (pyrimethamine); Flagyl 375 (metronidazole); Flagyl ER Tablets (metronidazole); Flagyl I.V. (metronidazole); Furoxone (furazolidone); Mepron (atovaquone); and Neutrexin (tfimetrexate glucuronate); Cipro (ciprofloxacin HCl); Floxin (ofloxacin); Levaquin (levofloxacin); Mazaquin (lomefloxacin HCl); Noroxin (norfloxacin); Penetrex (enoxacin); Raxar (grepafloxacin HCl); Trovan (trovafloxacin mesylate); and Zagam (sparfloxacin); Bactrim (trimethoprim and sulfamethoxazole); Bactrim DS (Irimethoprim and sulfamethoxazole double strength); Pediazole (erythromycin ethylsuccinate and sulfisoxazole acetyl); Septra (trimethoprim and sulfamethoxazole); Septra DS (trimethoprim and sulfamethoxazole); Co-Trimoxazole, Sulfadiazine, Battrim I.V. Infusion (sulfamethoxazole); Sulfapyridine and Pediazole (erythromycin ethylsuccinate and sulfisoxazole acetyl); Furadantin (nitrofurantoin); Macrobid (nitrofurantoin monohydrate macrocrystals); Macrodantin (nitrofurantoin macrocrystals); Monurol Sachet (fosfomycin tromethamine); NegGram Caplets (nalidixic acid); Septra (trimethoprim and sulfamethoxazole); Septra DS (trimethoprim and sulfamethoxazole); Urised (a combination of the antisepticsmethenamine, methylene blue, phenyl salicylate, benzoic acid and parasympatholytics (atropine sulfate) hyoscyamine); (oxytetracycline HCl, sulfamethizole and phenazopyridine HCl); (methenamine mandelate); Bactroban (mupirocin); Chloromycetin opthahnic (chloramphenical); Cortisporin (neomycin and polymyxin [3 ]sulfates and hydrocortisone acetate cream); Ilotycin (erythromycin opthalmic ointment); NeoDecadron (neomycin sulfate-dexamethasone sodium phosphate); Polytrim (tfimethoprim and polythyxin [3 ]sulfate opthalmic solution); Terra-Cortril (oxytetracycline HCl and hydrocortisone acetate); Terramycin (oxytetracycline); and TobraDex (tobramycin and dexamethasone opthalmic suspension and ointment); Vita-A opthalmic ointment, (vidatabine); (norfloxacinopthalmic solution; Ciloxan opthalmic solution and ointment (Ciprofloxacin HCl); and Ocuflox opthalmic solution (ofioxacin), Blephamide opthalmicointment (sulfacetamide sodium and prednisolone acetate); and Blephamideopthalmic suspension (sulfacetamide sodium and predrdsolone acetate); A/T/S (erythromycin); Bactroban (mupirocin); Benzamycin (erythromycin-benzoyl peroxide topical gel); Betadine (povidone-odine); Cleotin T (clindamy cinphosphate topical solution); Clindets (clindamycin phosphate pledgets); Cortispofin (neomycin, polymyxin B sulfates and hydrocortisone acetate cream); Emgel (erythromycin); Erycette (erythromycin topical solution); Garamycin (gentamicin sulfate); Klaron (sodium sulfacetamide lotion); Mycostatin (nystatin cream); Theramycin Z (erythromycin topical solution); T-Stat (erythromycin); Chloromycetin (chloramphenicol opthalmic ointment); Cortisporin (neomycin and polymyxin B sulfates, bacitracin zinc and hydrocortisone opthalmic ointment); Ilotycin (erythromycin); NeoDeeadron (neomycin sulfate-dexamethasone sodium phosphate); Polytrim (trimethoprim and polymyxin B sulfate); Terra-Cortril (oxytetracycline HCl and hydrocortisone acetate); Terramycin (oxytetracycline); Exelderm (sulconazole nitrate); Fungizone (amphotericin B oral suspension); Lamisil (terbinafine hydrochloride cream); Loprox (ciclopiroxolamine); Lotrimin (clotrimazole); Lotrisone (clotrimazole and betamethasone diproprionate); Mentax (butenafine HCl); Monistat-Denn (miconazole nitrate); Mycelex (clotrimazole); Mycostatin (nystatin); Naffin (nattifine HCl); Nizoral Ocetoconazole); Nystop (nystatin); Oxistat (oxiconazole nitrate); Selsun Rx (2.5% selenium sulfide lotion); and Spectazole (econazole nitrate); Denavir (penciclovir cream); and Zovirax (acyclovir); Benzashave Coenzoyl peroxide); Betadine (povidone-iodine); Betasept (chlorhexidine gluconate); Cetaphil (soap substitute); Clorpactin WCS-90 (sodium oxychlorosene); Dapsone Tablets (dapsone); Desquam-E Coenzoyl peroxide); Desquam-X (benzoyl peroxide); Hibiclens (chlorhexidine gluconate); Hibistat (ehlorhexidine gluconate); Impregon (tetrachlorosalicylanilide 2%); Metro-Cream (metronidazole); MetroGel (metronidazole); Noritate (metronidazole); pHisoHex (hexachlorophene detergent cleanser); Sulfacet-R (sodium sulfacetamide 10% and sulfur 5%); Sulfamylon (materfide acetate); Tfiaz Coenzoyl peroxide); and Vanoxide-HC Coenzoyl peroxide hydrocortisone); Acticin (permethrin); Elimite (permethrin); Eurax (crotamiton); Efudex (fluoro-uracil); Fluoroplex.

Pharmaceutical Compositions

Hosts, including humans can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

An optional dose of the compound for treatment of a bacterial (such as a gram negative bacteria) infection is about 1 to 50 mg/kg, or 1 to 20 mg/kg, of body weight per day, more generally 0.1 to about 100 mg per kilogram body weight of the recipient per day. The effective dosage range of the pharmaceutically acceptable salts and prodrugs can be calculated based on the weight of the parent nucleoside to be delivered. If the salt or prodrug exhibits activity in itself, the effective dosage can be estimated as above using the weight of the salt or prodrug, or by other means known to those skilled in the art.

Optionally, the active ingredient should be administered to achieve peak plasma concentrations of the active compound of from about 0.2 to 70 M, e.g., about 1.0 to 10 uM. This may be achieved, for example, by the intravenous injection of a 0.1 to 5% solution of the active ingredient, optionally in saline, or administered as a bolus of the active ingredient. The concentration of active compound in the drug composition will depend on absorption, inactivation and excretion rates of the drug as well as other factors known to those of skill in the art. It is to be further understood that for any particular subject, specific dosage regimens should be adjusted according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

The compound is conveniently administered in unit any suitable dosage form, including but not limited to one containing 7 to 3000 mg, or 70 to 1400 mg of active ingredient per unit dosage form. A dosage of 50-1000 mg is optional.

The active compound can be administered in a pharmaceutically acceptable carrier available in the art, and can be administered by a chosen route of administration. Pharmaceutical compositions can be prepared, packaged, or sold in a variety of formulations which can be suitable for one or more routes of administration such as, for example, oral, intravenous, intramuscular, topical, subcutaneous, rectal, vaginal, parenteral, pulmonary, intranasal, buccal, ophthalmic, or another route of administration. The active materials can be administered in liquid or solid form. Other contemplated formulations include projected nanoparticles, liposomal preparations, resealed erythrocytes containing the active ingredient, and immunologically-based formulations.

The active compound may be administered intravenously or intraperitoneally by infusion or injection. Solutions of the active compound or its salts may be prepared in water or saline, optionally mixed with a non-toxic surfactant. Dispersions may be prepared in glycerol, liquid polyethylene glycols, triacetin, mixtures thereof, and in oils. Under ordinary conditions of storage and use, these preparations contain a preservative to prevent growth of microorganisms.

Pharmaceutical dosage forms suitable for injection or infusion may include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form is optionally sterile, fluid, and stable under conditions of manufacture and storage. The liquid carrier or vehicle may be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof.

For oral therapeutic administration, the active compound can be combined with one or more excipients and used in the form of ingestible tablets, buccal tablets, troches, capsules, elixirs, suspensions, syrups, wafers, and the like. Such compositions and preparations can contain at least 0.1% (w/w) of active compound. The percentage of the compositions and preparations can, of course, be varied, for example from about 0.1% to nearly 100% of the weight of a given unit dosage form. The amount of active compound in such therapeutically useful compositions is such that an effective dosage level will be obtained upon administration.

The tablets, troches, pills, capsules, and the like may also contain one or more of the following: binders, such as microcrystalline cellulose, gum tragacanth, acacia, corn starch, or gelatin; excipients, such as dicalcium phosphate, starch or lactose; a disintegrating agent, such as corn starch, potato starch, alginic acid, primogel, and the like; a lubricant, such as magnesium stearate or Sterotes; a glidant, such as colloidal silicon dixoide; a sweetening agent, such as sucrose, fructose, lactose, saccharin, or aspartame; a flavoring agent such as peppermint, methylsalicylate, oil of wintergreen, or cherry flavoring; and a peptide antibacterial agent, such as envuvirtide (Fuzeon™). When the unit dosage form is a capsule, it can contain, in addition to materials of the above type, a liquid carrier, such as a vegetable oil or a polyethylene glycol. Various other materials may be present as coatings or to otherwise modify the physical form of the solid unit dosage form.

In one embodiment, the active compounds are prepared with carriers that will protect the compound against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylacetic acid. Methods for preparation of such formulations will be apparent to those skilled in the art. The materials may also be obtained commercially from Alza Corporation.

Other formulations can also be developed. For example, the compounds can be administered in liposomal suspensions (including liposomes targeted to infected cells with monoclonal antibodies to bacterial antigens). These may be prepared according to methods known to those skilled in the art, for example, as described in U.S. Pat. No. 4,522,811. For example, liposome formulations may be prepared in a variety of lipid(s) (such as stearoyl phosphatidyl ethanolamine, stearoyl phosphatidyl choline, arachadoyl phosphatidyl choline, and cholesterol).

A pharmaceutical composition of the invention may be prepared, packaged, or sold in a formulation suitable for rectal administration. Such a composition may be in the form of, for example, a suppository, a retention enema preparation, and a solution for rectal or colonic irrigation. A pharmaceutical composition of the invention may also be prepared, packaged, or sold in a formulation suitable for vaginal administration. Such a composition may be in the form of, for example, a suppository, an impregnated or coated vaginally-insertable material such as a tampon, a douche preparation, or a solution for vaginal irrigation.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration, which can include particles wherein at least 98% of the particles by weight have a diameter greater than 0.5 nanometers and at least 95% of the particles by number have a diameter less than 7 nanometers. Typically least 95% of the particles by weight have a diameter greater than 1 nanometer and at least 90% of the particles by number have a diameter less than 6 nanometers. The active ingredient can also be in the form of droplets of a solution or suspension, for example those that have an average diameter in the range from about 0.1 to about 200 nanometers.

The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers.

A pharmaceutical composition of the invention may be prepared, packaged, or sold in a formulation suitable for ophthalmic administration. For topical administration, the present compounds can be applied in pure form, i.e., as a liquid. However, typically, the compounds are administered to the skin as compositions or formulations, in combination with a dermatologically acceptable carrier. Useful solid carriers include finely divided solids such as talc, clay, microcrystalline cellulose, silica, alumina, and the like. Useful liquid carriers include water, alcohols, glycols, and blends of two or more of these, in which the present compounds can be dissolved or dispersed at effective levels, optionally with the aid of non-toxic surfactants. Adjuvants such as fragrances and additional antimicrobial agents can be added to optimize properties for a given use. The resulting liquid compositions can be applied using absorbent pads, used to impregnate bandages or other dressings, or sprayed onto the affected area using pump-type or aerosol sprayers.

The compounds/compositions of the present invention are optionally administered in a controlled release formulation, which can be a degradable or nondegradable polymer, hydrogel or ganogel or other physical construct that modifies the bioabsorption, half life or biodegradation of the active agent(s). The controlled release formulation can be a material that is painted or otherwise applied onto the afflicted site, either internally or externally. In one embodiment, the invention provides a biodegradable bolus or implant. The controlled release formulation with appropriated selected imaging agent can be used to coat a transplanted organ or tissue to prevent rejection. It can alternatively be implanted or otherwise applied near the site of potential infection.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

The compound or a pharmaceutically acceptable prodrug or salts thereof can also be mixed with other active materials that do not impair the desired action, or with materials that supplement the desired action, such as antibiotics, antifungals, anti-inflammatories, or other antibacterials, including other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antiacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposale syringes or multiple dose vials made of glass or plastic. If administered intravenously, useful carriers are physiological saline or phosphate buffered saline (PS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation.

The concentration of the compound(s) in a liquid composition, such as a lotion, will, for example, range from about 0.1% to about 95% by weight, or from about 0.5% to about 25% by weight. The concentration in a semi-solid or solid composition such as a gel or a powder will, for example, range from about 0.1% to 100% by weight, or about 0.5% to about 5% by weight. Single doses for intravenous injection, subcutaneous, intramuscular or topical administration, infusion, ingestion or suppository will generally be from about 0.001 to about 5000 mg, and be administered from about 1 to about 3 times daily, to yield levels of about 0.01 to about 500 mg/kg, for adults.

The invention also includes one or more compounds disclosed herein, or any combination thereof, or salt thereof, in an amount effective to inhibit bacterial (such as a gram negative bacteria) replication in a host. The compound can be useful for inhibiting bacterial replication in a cell or neutralization (i.e. inactivation) of extracellular bacteria.

As used herein, to inhibit bacterial replication in a host means to reduce the bacterial load in a host to a level which is lower than the level of the bacterial load in an otherwise identical host which was not administered the compound. Bacterial load in a mammal can be reduced by about 1 to 12 $\log_{10}$ or more relative to an otherwise identical mammal which was not administered the compound. Bacterial load in a mammal can be assessed by a number of methods known in the art such as, for example, obtaining a tissue or fluid sample from the mammal and assessing the amount of bacterial components in the mammal contained therein using technology which is either immunological, biochemical or molecular biological in nature and which is well known to the skilled artisan and which are described elsewhere herein. Inhibition of bacterial replication in a cell is assessed using similar or identical assays as those used to assess bacterial load in a mammal.

The invention also includes a kit for administering a compound of the invention, a pharmaceutically acceptable salt thereof, or a pharmaceutical composition, to a host for treatment of a bacterial (such as a gram negative bacteria) infection. Typically, the host is a human. The kit comprises one or more compounds of the invention, or a combination thereof, and optionally an instructional material, which describes adventitially administering the composition to the mammal by any of the routes of administration described herein. In another embodiment, this kit comprises a (typically sterile) solvent suitable for dissolving or suspending the composition of the invention prior to administering the compound to the mammal.

EXAMPLES

Melting points were determined on a Mel-temp II laboratory device and are uncorrected. Nuclear magnetic resonance spectra were obtained on a GE 300 Plus (300 MHz), a Varian INOVA 400 (400 MHz), and a Varian INOVA 600 (600 MHz) spectrometer; chemical shifts (δ) are reported in parts per million (ppm), and the signals are described as s (singlet), d (doublet), t (triplet), q (quartet), bs or brs (broad singlet), dd (doublet of doublet), and m (multiplet). UV spectra were obtained on a Beckman DU 650 spectrophotometer. Mass spectra were measured on a Micromass Inc. Autospec High Resolution double focussing sector (EBE) MS spectrometers. Infrared spectra were obtained on a Nicolet 510 FT-IR spectrometer. All reactions were monitored using thin layer chromatography on Analtech, 200 mm silica gel GF plates. Dry 1,2-dichloroethane, dichloromethane, acetonitrile, N,N-dimethylformamide, and THF were obtained by drying over 4 A molecular sieves.

Abbreviations:

ACN: acetonitrile
DCE: 1,2-dichloroethane
DCM: dichloromethane
DDQ: dichlorodicyano quinone
DIEA: diisopropylethyl amine
DI H$_2$O: deionized water
DMAP: 4-dimethylamino pyridine
DMF: N,N-dimethyl formamide
DPPB: 1,4-bis(diphenylphosphine)butane
LAH: lithiumaluminum hydride
LHMDS: lithium hexamethyldisilazide
Pd/C: palladium on carbon
PNB: p-nitrobenzyl
PTSA: p-toluenesulfonic acid monohydrate
TBAF: tetrabutylammonium fluoride
TBDMS: t-butyldimethylsilyl
TEA: triethylamine
TES: triethylsilyl
TFA: trifluoroacetic acid
THF: tetrahydrofuran
TLC: thin layer chromatography
TBDPS: t-buthyldiphenylsilyl Preparation of the Carbapenem Intermediate (CPI) 5

Carbapenem Intermediate (CPI) 5 was prepared according to the synthetic scheme shown in FIG. 3. In the first step of the process, benzyl propionate is reacted with isobutoxycarbonyloxy acetic acid methyl ester in a solvent at low temperature in the presence of LDA to form ketoester A. The ketoester A is then contacted with the acetoxyazetidinone B (prepared by any number of known, synthetic routes) in a solvent, and sodium carbonate is added. The reaction ages for a period of time at a temperature such that the reaction goes substantially to completion, generating the target lactam C.

The lactam C is dissolved in a solvent, such as DMF, to which a suitable base (such as DIEA) and TBSOTf are added, and the mixture allowed to age for a period of time at a temperature. Following workup, the bis-TBS-ketoester D is isolated.

The crude ketoester D is dissolved in ethyl acetate in an appropriate reaction vessel. Formic acid and a catalyst, such as Pd/C, are added to the reaction vessel, and the entire mixture is hydrogenated at an appropriate hydrogen pressure (40-50 psi) for a period of time such that the decarboxylation reaction proceeds to completion. The reaction mixture is filtered over a pad of Celiteg, and the solvent is removed under vacuum. Product E is isolated following purification by column chromatography.

The bis-TBDMS ketolactam E is then de-silylated using 2 N HCl in ACN and the product is isolated after a standard aqueous workup. The crude product is dissolved in a solvent, such as DCM, and allowed to react with triethylsilyl chloride and imidazole for several hours (monitored by TLC) at rt. Following aqueous workup, O-TES ketolactam F was isolated and purified on silica gel.

N-PNB, O-TES ketolactam G is produced by reacting ketolactam F with p-nitrobenzyl oxalylchloride in a suitable solvent (DCM, for example) in the presence of a base (DIEA, for example). The mixture is allowed to age for a period of time (and at an appropriate temperature) to effect a substantially complete reaction as monitored by an appropriate means (e.g., TLC or HPLC). Following workup in a usual manner, intermediate G was isolated.

To a solution of compound G is a suitable solvent was added triethylphosphite, and the mixture heated to reflux until complete by TLC. Following workup and purification in the appropriate manner, CPI 5 was isolated.

The Amine Series: Preparation of Gram-Negative Active Carbapenems

The amine series of 1-β-methylcarbapenem analogs possessing Gram-negative activity were synthesized using synthetic methods described above and as illustrated in Scheme 2 below, unless otherwise noted. In general, a series of secondary amines (2) were coupled to CPI 5 (FIG. 3) in DMF using a combination of Pd$_2$(dba)$_3$CHCl$_3$ with DPPB (Method A) or triethylphosphite (Method B) at rt to produce the coupled intermediate 3. In some cases, 2,6-lutidine (Method C) or PTSA (Method D) were added to drive the reaction to completion. The secondary amines were either purchased from commercial sources or prepared by alkylation of N-Boc-protected primary amines with various alkyl halides followed by cleavage of the Boc protecting group with TFA/water in DCM.

Removal of the TES protecting group in the series of intermediate 3 was accomplished with aqueous triflic acid solution in IPA/water (pH 2.4, Method E) or with 0.06N HCl in IPA/THF (Method F) at 0° C. to rt.

Lastly, the PNB group(s) in intermediate 4 were removed by hydrogenation of the corresponding PNB esters using standard conditions (atmospheric H$_2$ pressure, 5% Pt/C, THF/i-PrOH/0.5 M potassium phosphate buffer solution (pH 7.0) at 0° C.) and the final products 6 were isolated after purification on SP-207 resin.

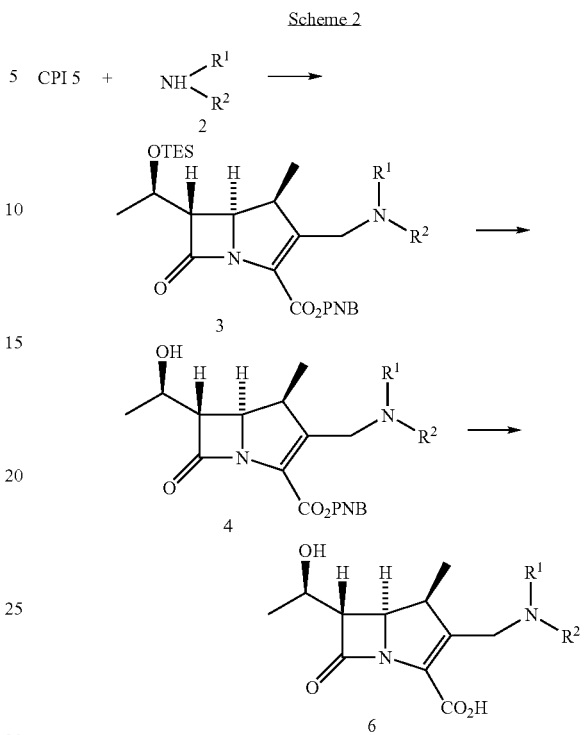

Step 1: General Procedure for the Palladium Coupling Reaction

Method A:

To a dry, round-bottom flask, anhydrous DMF (40 mL) was added and the solvent was stirred and degassed at room temperature with two cycles of nitrogen/vacuum. Pd$_2$(dba)$_3$CHCl$_3$ (51.8 mg, 0.05 mmol) and DPPB (64.0 mg, 0.15 mmol) were then added. The solution was degassed with two nitrogen/vacuum cycles and aged for 20 minutes. The appropriate secondary amine (2) (1.1 mmol) was added and the mixture was again degassed under reduced pressure for 5 min. CPI 5 (590.7 mg, 1.0 mmol) was then added, the resulting mixture was again degassed with two nitrogen/vacuum cycles, and the resulting mixture was aged for 12-36 h (monitored by TLC) at rt. The solvent was then removed under reduced pressure and the resulting residue was purified by flash chromatography on silica gel to produce coupled intermediate 3 in 50-98% yield.

Method B:

To a dry, round-bottom flask, anhydrous DMF (40 mL) was added and the solvent was stirred and degassed at room temperature with two cycles of nitrogen/vacuum. Pd$_2$(dba)$_3$CHCl$_3$ (51.8 mg, 0.05 mmol) and P(OEt)$_3$ (24.9 mg, 0.15 mmol). were then added. The solution was degassed with two nitrogen/vacuum cycles and aged for 20 minutes. The appropriate secondary amine (2) (1.1 mmol) was added and the mixture was again degassed under reduced pressure for 5 min. CPI 5 (590.7 mg, 1.0 mmol) was then added, the resulting mixture was again degassed with two nitrogen/vacuum cycles, and the resulting mixture was aged for 12-36 h (monitored by TLC) at rt. The solvent was then removed under reduced pressure and the resulting residue was purified by flash chromatography on silica gel to produce coupled intermediate 3 in 50-98% yield.

Method C:

Used a similar procedure as was described in Method B except that 2,6-lutidine (0.5 eq) was added in conjunction with reagent 2.

Method D:

Used a similar procedure as was described in Method B except that PTSA (0.5 eq) and 4 A molecular sieves were added in conjunction with the palladium catalyst.

Step 2: General Procedure for the Removal of the TES Protecting Group

Method E:

Preparation of the pH 2.4 aqueous/IPA triflic acid stock solution; 620 uL of triflic acid was added to a stirred solution of DI $H_2O$ (100 mL) and IPA (500 mL). Additional triflic acid was added dropwise to adjust the pH to 2.4. TES-Intermediate 3 (100 mg) was then added to 3 mL of the aqueous triflic acid:IPA stock solution and the resulting mixture was stirred at rt. The reaction pH was then adjusted to 2.4 by the incremental addition of triflic acid stock solution, if necessary. The reaction mixture was stirred at rt until complete by TLC (~2 h), neutralized with 0.5M potassium phosphate buffer solution (pH 7.0, 5-10 mL), and the resulting mixture was stirred for 10 min and then extracted with ethyl acetate. The organic layer was washed with brine, dried over anhydrous sodium sulfate, and concentrated under reduced pressure. The crude product was purified by flash chromatography on silica gel using as eluent hexane/ethyl acetate with gradient or ethyl acetate/methanol with gradient to produce alcohol 4 in 67-92% yield.

Method F:

Alcohol 4 (100 mg) was dissolved in THF/IPA (2 mL/2 mL) and cooled to 0° C. 0.06N HCl solution was then added (1-3 mL, pH adjusted to 2.4) and the resulting mixture was aged at 0° C. for 2-18 h (monitored by TLC). The reaction was neutralized with 0.5M potassium phosphate buffer solution (pH 7.0, 5-10 mL), and the resulting mixture was carried on to Step 3 without further isolation or purification.

Step 3: General Procedure for the Removal of the PNB Protecting Group

To a round-bottom flask equipped with a side arm were added alcohol intermediate 4 (200 mg) and THF/IPA (3 mL/3 mL), and the resulting mixture was stirred at rt. Aqueous 0.5 M potassium phosphate buffer solution (pH 7.0, 6 mL), was then added and the resulting mixture was cooled to 0° C. 5% Pt/C (40 mg) was added and the reaction flask was fitted with a hydrogen balloon, degassed under reduced pressure, and charged with hydrogen. The resulting mixture was aged for 4-14 hrs. (monitored by TLC) at 0° C., diluted with chilled ethyl acetate (20 mL) and DI $H_2O$ (10 mL), and filtered over a pad of Celite. The celite was washed with chilled DI $H_2O$ (30 mL) and ethyl acetate (30 mL), the layers separated, and the aqueous layer was extracted with cold ethyl acetate (30 mL). The aqueous fraction was then concentrated under reduced pressure to remove any organics and lyophilized. The crude material was purified on SP-207 resin with IPA/DI $H_2O$ and the column fractions concentrated under reduced pressure at 110° C. to remove i-PrOH and then lyophilized to give the desired, final product 6 as fluffy solids.

Example 1

TES-Protected Cyanoethylamine CP Intermediate 7

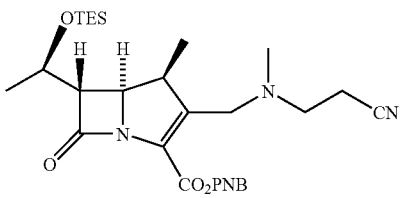

Method A; Percent yield: 98%; $^1$H NMR (CDCl$_3$, 300 MHz): δ 8.20 (d, J=9.0 Hz, 2H), 7.66 (d, J=8.4 Hz, 2H), 5.44 (d, J=14.1 Hz, 2H), 5.21 (d, J=14.1 Hz, 2H), 4.29-4.20 (m, 2H), 3.93 (d, J=15.0 Hz, 1H), 3.47-3.36 (m, 1H), 3.25 (dd, J=4.8; 2.7 Hz, 1H), 3.14 (d, J=14.7 Hz, 1H), 2.78-2.69 (m, 1H), 2.64-2.56 (m, 1H), 2.51-2.47 (m, 2H), 2.25 (s, 3H), 1.24 (d, J=7.2 Hz, 3H), 1.18 (d, J=7.5 Hz, 3H), 0.93 (t, J=7.8 Hz, 9H), 0.59 (q, J=7.5 Hz, 6H).

PNB-Protected Cyanoethylamine CP Intermediate 8

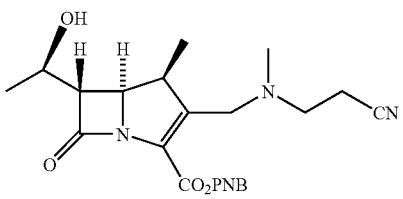

Method E; Percent yield: 75%; $^1$H NMR (CDCl$_3$, 300 MHz): δ 8.16 (d, J=9.3 Hz, 2H), 7.60 (d, J=8.4 Hz, 2H), 5.43 (d, 14.4 Hz, 2H), 5.15 (d, J=14.4 Hz, 2H), 4.24-4.18 (m, 2H), 3.90 (d, J=14.7 Hz, 1H), 3.50-3.40 (m, H), 3.26 (dd, J=6.6; 3.0 Hz, 1H), 3.11 (d, J=14.7 Hz, 1H), 2.86 (br s, 1H), 2.75-2.66 (m, 1H), 2.60-2.52 (m, 1H), 2.50-2.45 (m, 2H), 2.23 (s, 3H), 1.28 (d, J=6.9 Hz, 3H), 1.15 (d, J=7.5 Hz, 3H).

Cyanoethylamine CP Analog 9

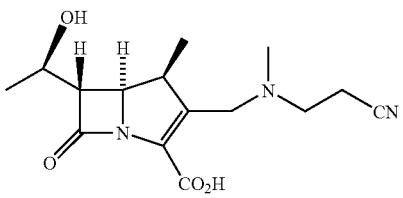

Percent yield: 50%; $^1$H NMR (D$_2$O, 400 MHz): δ 4.22-4.15 (m, 2H), 3.75 (d, J=14.4 Hz, 1H), 3.42-3.39 (m, 2H), 3.24-3.16 (m, 1H), 3.05-2.98 (m, 1H), 2.83-2.72 (m, 3H), 2.38 (s, 3H), 1.23 (d, J=6.4 Hz, 3H), 1.08 (d, J=7.6 Hz, 3H).

Example 2

TES-Protected N-Methyl Acetamide CP
Intermediate 10

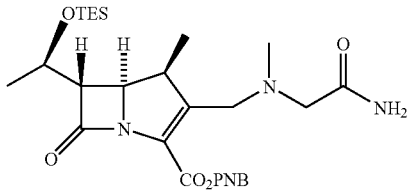

Method A; Percent yield; 98%; ¹H NMR (CDCl₃, 300 MHz): δ 8.20 (d, J=8.1 Hz, 2H), 7.65 (d, J=8.4 Hz, 2H), 6.87 (br s, 1H), 6.32 (br s, 1H), 5.43 (d, J=14.1 Hz, 1H), 5.21 (d, J=14.1 Hz, 1H), 4.29-4.19 (m, 2H), 4.03 (d, J=14.7 Hz, 1H), 3.33-3.23 (m, 2H), 3.14 (14.1 Hz, 1H), 3.07 (d, J=17.1 Hz, 1H), 2.93 (d, J=15.6 Hz, 1H), 2.29 (s, 3H), 1.24 (d, J=5.4 Hz, 3H), 1.18 (d, J=7.2 Hz, 3H), 0.92 (t, J=8.4 Hz, 9H), 0.58 (q, J=8.4 Hz, 6H).

PNB-Protected N-Methyl Acetamide CP
Intermediate 11

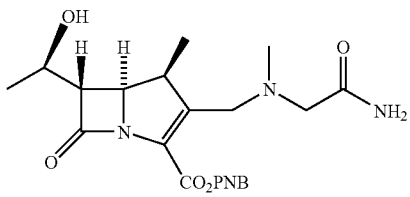

Method E; Percent yield: 75%; ¹H NMR (CDCl₃, 300 MHz): δ 8.16 (d, J=8.4 Hz, 2H), 7.60 (d, J=8.7 Hz, 2H), 6.88 (br s, 1H), 6.50 (br s, 1H), 5.43 (d, J=14.1 Hz, 2H), 5.17 (d, J=14.1 Hz, 2H), 4.23-4.15 (m, 2H), 3.97 (d, J=13.5 Hz, 1H), 3.36-3.24 (m, 2H), 3.11 (d, J=14.1 Hz, 1H), 3.03 (d, J=15.6 Hz, 1H), 2.88 (d, J=16.8 Hz, 1H), 2.25 (s, 3H), 1.28 (d, J=5.7 Hz, 3H), 1.15 (d, J=7.2 Hz, 3H).

N-Methyl Acetamide CP Analog 12

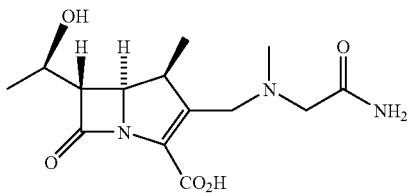

Percent yield: 87%; ¹H NMR (D₂O, 400 MHz): δ 4.26-4.18 (m, 2H), 3.92 (d, J=14.4 Hz, 1H), 3.66 (d, J=14.4 Hz, 1H), 3.61 (d, J=16.0 Hz, 1H), 3.52 (d, J=16.0 Hz, 1H), 3.46-

3.44 (m, 1H), 3.29-3.21 (m, 1H), 2.59 (s, 3H), 1.27 (d, J=6.4 Hz, 3H), 1.13 (d, J=7.2 Hz, 3H).

Example 3

TES-Protected N-Methyl Acetamide CP
Intermediate 13

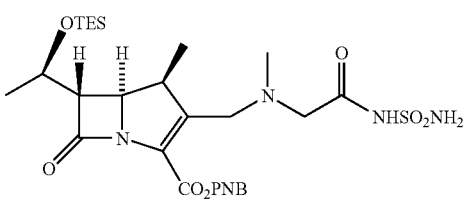

Method C; Percent yield: 62%; ¹H NMR (CDCl₃, 300 MHz): δ 8.21 (d, J=8.4 Hz, 2H), 7.66 (d, J=9.3 Hz, 2H), 6.90 (br s 1H), 6.22 (br s, 1H), 5.44 (d, J=13.5 Hz, 1H), 5.38 (br s, 1H), 5.22 (d, J=13.5 Hz, 1H), 4.28-4.20 (m, 2H), 4.04 (d, J=14.1 Hz, 1H), 3.30-3.24 (m, 1H), 3.15 (d, J=14.1 Hz, 1H), 3.08 (d, J=16.2 Hz, 1H), 2.94 (d, J=16.2 Hz, 1H), 2.30 (s, 3H), 1.25 (d, J=6.6 Hz, 3H), 1.18 (d, J=6.6 Hz, 3H), 0.93 (t, J=8.4 Hz, 9H), 0.59 (q, J=7.8 Hz, 6H).

PNB-Protected N-Methyl Acetamide CP
Intermediate 14

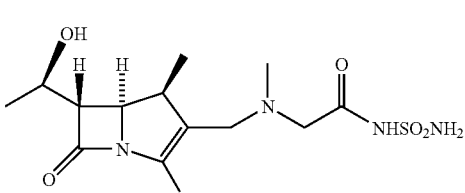

Method E; Percent yield: 60%; ¹H NMR (acetone-d₆, 300 MHz): δ 8.22 (d, J=9.0 Hz, 2H), 7.79 (d, J=8.4 Hz, 2H), 7.15 (br s, 1H), 6.76 (br s, 1H), 5.51 (d, J=14.1 Hz, 2H), 5.30 (d, J=14.1 Hz, 2H), 4.26 (dd, J=10.2; 3.0 Hz, 1H), 4.18-4.07 (m, 1H), 4.06-3.94 (m, 2H), 3.56-3.45 (m, 1H), 3.33-3.30 (m, 1H), 3.07 (d, J=15.6 Hz, 1H), 2.94 (d, J=15.6 Hz, 1H), 2.28 (s, 3H), 1.24 (d, J=6.0 Hz, 3H), 1.20 (d, J=7.5 Hz, 3H).

N-Methyl Acetamide CP Analog 15

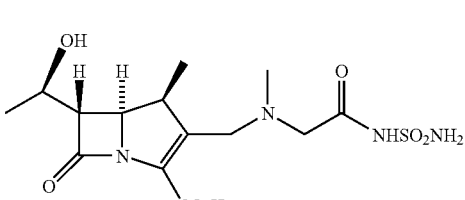

Percent yield: 46%; ¹H NMR (D₂O, 300 MHz): δ 4.22-4.13 (m, 2H), 3.86 (d, J=13.5 Hz, 1H), 3.62-3.41 (m, 3H), 3.40 (dd, J=6.0; 2.7 Hz, 1H), 3.26-3.16 (m, 1H), 2.52 (s, 3H), 1.22 (d, J=6.0 Hz, 1H), 1.09 (d, J=7.5 Hz, 3H).

Example 4

TES-Protected N-Methyl Ethylamine CP Intermediate 16

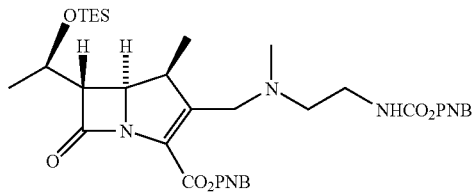

Method A; Percent yield: 48%; $^1$H NMR (CDCl$_3$, 300 MHz): δ 8.18 (d, J=8.4 Hz, 2H), 8.17 (d, J=8.7 Hz, 2H), 7.64 (d, J=8.4 Hz, 2H), 7.48 (d, J=8.4 Hz, 2H), 5.43 (d, J=13.8 Hz, 1H), 5.29 (br s, 1H), 5.19 (d, J=13.8 Hz, 1H), 5.16 (s, 2H), 4.25-4.16 (m, 2H), 3.85 (d, J=14.4 Hz, 1H), 3.32-3.26 (m, 3H), 3.22 (dd, J=5.7; 2.7 Hz, 1H), 3.10 (d, J=14.4 Hz, 1H), 2.56-2.42 (m, 2H), 2.18 (s, 3H), 1.22 (d, J=6.6 Hz, 3H), 1.13 (d, J=7.2 Hz, 3H), 0.90 (t, J=8.4 Hz, 9H), 0.57 (q, J=7.8 Hz, 6H).

PNB-Protected N-Methyl Ethylamine CP Intermediate 17

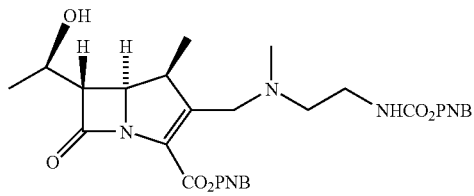

Method E; Percent yield: 93%; $^1$H NMR (CDCl$_3$, 300 MHz): δ 8.19 (d, J=8.4 Hz, 2H), 8.18 (d, J=7.5 Hz, 2H), 7.62 (d, J=8.4 Hz, 2H), 7.49 (d, J=8.4 Hz, 2H), 5.46 (d, J=13.8 Hz, 1H), 5.40 (br s, 1H), 5.18 (d, J=13.8 Hz, 1H), 5.17 (s, 2H), 4.23 (m, 2H), 3.90 (d, J=15.0 Hz, 1H), 3.38-3.25 (m, 4H), 3.16 (d, J=14.4 Hz, 1H), 2.64-2.44 (m, 2H), 2.23 (s, 3H), 1.30 (d, J=5.4 Hz, 3H), 1.14 (d, J=7.5 Hz, 3H).

N-Methyl Ethylamine CP Analog 18

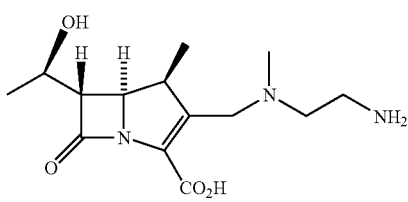

Percent yield: 27%; $^1$H NMR (D$_2$O, 300 MHz): δ 4.20-4.13 (m, 2H), 3.76 (d, J=14.7 Hz, 1H), 3.40-3.32 (m, 2H), 3.19-3.10 (m, 3H), 2.91-2.68 (m, 2H), 2.36 (s, 3H), 1.22 (d, J=6.0 Hz, 3H), 1.02 (d, J=7.2 Hz, 3H).

Example 5

TES-Protected N-Methyl Sulfonamide CP Intermediate 19

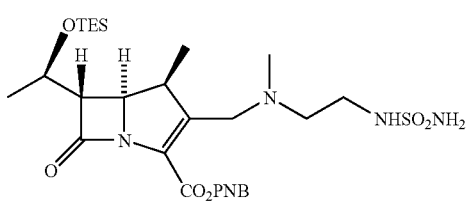

Method C; Percent yield: 43%; $^1$H NMR (CDCl$_3$, 300 MHz): δ 8.22 (d, J=8.4 Hz, 2H), 7.68 (d, J=9.0 Hz, 2H), 5.46 (d, J=14.1 Hz, 1H), 5.36 (br s, 1H), 5.24 (d, J=14.1 Hz, 1H), 5.10 (br s, 1H), 4.29-4.22 (m, 2H), 3.96 (d, J=13.8 Hz, 1H), 3.31-3.21 (m, 3H), 3.08 (d, J=13.8 Hz, 1H), 2.70-2.50 (m, 2H), 2.24 (s, 3H), 1.25 (d, J=6.3 Hz, 3H), 1.16 (d, J=7.5 Hz, 3H), 0.95 (t, J=8.7 Hz, 9H), 0.60 (q, J=7.5 Hz, 6H).

PNB-Protected N-Methyl Sulfonamide CP Intermediate 20

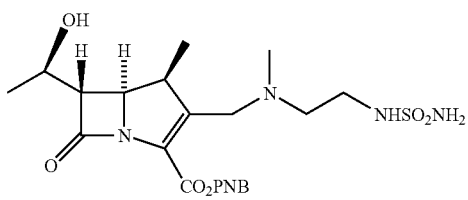

Mehtod E; Percent yield: 61%; $^1$H NMR (acetone-d$_6$, 300 MHz): δ 8.23 (d, J=9.0 Hz, 2H), 7.79 (d, J=9.0 Hz, 2H), 5.98 (br s, 1H), 5.74 (d, J=14.1 Hz, 1H), 5.45 (br s, 1H), 5.29 (d, J=14.1 Hz, 1H), 4.24 (dd, J=10.2; 3.6 Hz, 1H), 4.20-4.09 (m, 1H), 3.84 (d, J=14.7 Hz, 1H), 3.48-3.40 (m, 1H), 3.30 (dd, J=7.2; 3.0 Hz, 1H), 3.25-3.15 (m, 1H), 2.67-2.58 (m, 1H), 2.51-2.45 (m, 1H), 2.21 (s, 3H), 1.24 (d, J=6.3 Hz, 3H), 1.18 (d, J=6.6 Hz, 3H).

N-Methyl Sulfonamide CP Analog 21

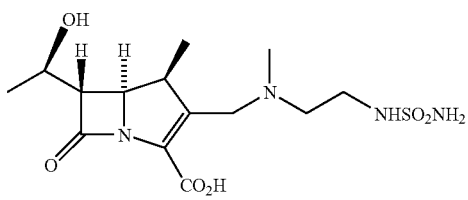

Percent yield: 68%; $^1$H NMR (D$_2$O, 400 MHz): δ 4.25-4.22 (m, 2H), 4.06 (d, J=14.4 Hz, 1H), 3.95 (d, J=14.4 Hz, 1H), 3.49 (dd, J=6.0; 2.8 Hz, 1H), 3.48-3.45 (m, 2H), 3.34-3.19 (m, 3H), 2.85 (s, 3H), 1.27 (d, J=6.4 Hz, 3H), 1.17 (d, J=7.6 Hz, 3H).

Example 6

TES-Protected N-Methyl Imidazole CP Intermediate 22

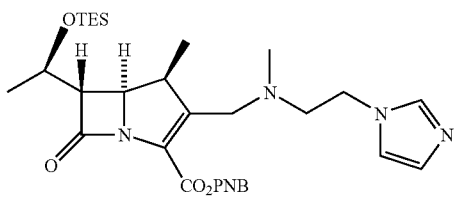

Method C; Percent yield: 40%; ¹H NMR (CDCl₃, 300 MHz): δ 8.15 (d, J=9.0 Hz, 2H), 7.62 (d, J=8.4 Hz, 2H), 7.44 (s, 1H), 6.97 (s, 1H), 6.88 (s, 1H), 5.40 (d, J=13.8 Hz, 1H), 5.16 (d, J=13.8 Hz, 1H), 4.23-4.16 (m, 1H), 4.05 (dd, J=10.5; 3.3 Hz, 1H), 3.98-3.95 (m, 2H), 3.89 (d, J=15.0 Hz, 1H), 3.14 (dd, J=4.8; 3.0 Hz, 1H), 3.02 (d, J=15.0 Hz, 1H), 2.88-2.77 (m, 1H), 2.71-2.62 (m, 1H), 2.59-2.50 (m, 1H), 2.23 (s, 3H), 1.18 (d, J=6.6 Hz, 3H), 0.96-0.88 (m, 12H), 0.55 (q, J=8.1 Hz, 6H).

N-Methyl Imidazole CP Analog 23

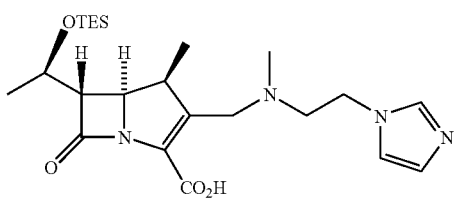

Method F; Percent yield: 38% (from 22); ¹H NMR (D₂O, 300 MHz): δ 7.79 (s, 1H), 7.16 (s, 1H), 7.03 (s, 1H), 4.32-4.25 (m, 2H), 4.20-4.11 (m, 1H), 4.08-4.05 (m, 1H), 3.73 (d, J=15.0 Hz, 1H), 3.42 (d, J=15.0 Hz, 1H), 3.36-3.40 (m, 1H), 3.19-3.10 (m, 1H), 2.99-2.86 (m, 2H), 2.46 (s, 3H), 1.20 (d, J=6.3 Hz, 3H), 1.00 (d, J=7.2 Hz, 3H).

Example 7

TES-Protected N-Methyl Guanidine CP Intermediate 24

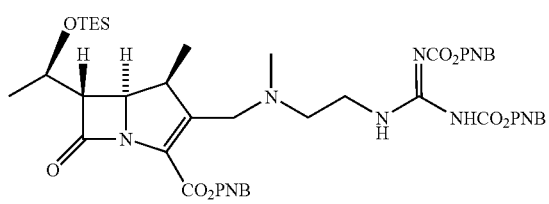

Method B; Percent yield: 32%; ¹H NMR (CDCl₃, 300 MHz): δ 11.77 (s, 1H), 8.68 (s, 1H), 8.26-8.19 (m, 6H), 7.67 (d, J=8.1 Hz, 2H), 7.54-7.50 (m, 4H), 5.46 (d, J=13.5 Hz, 1H), 5.25 (s, 2H), 5.22 (s, 2H), 5.22 (d, J=13.5 Hz, 1H), 4.28-4.20 (m, 2H), 3.93 (d, J=14.7 Hz, 1H), 3.57-3.55 (m, 2H), 3.46-3.38 (m, 1H), 3.24 (dd, J=5.4; 3.0 Hz, 1H), 3.16 (d, J=14.7 Hz, 1H), 2.68-2.48 (m, 2H), 2.21 (s, 3H), 1.25 (d, J=6.0 Hz, 3H), 1.13 (d, J=7.2 Hz, 3H), 0.93 (t, J=8.1 Hz, 9H), 0.60 (q, J=8.1 Hz, 6H).

N-Methyl Guanidine CP Analog 25

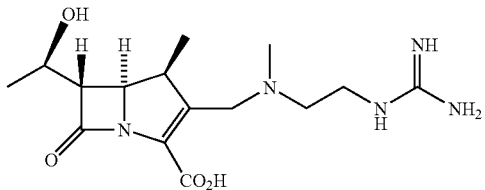

Method F; Percent yield: 25% (from 24); ¹H NMR (D₂O, 400 MHz): δ 4.23 (quintet, J=6.0 Hz, 1H), 4.18 (d, J=10.0 Hz, 1H), 3.75 (d, J=14.4 Hz, 1H), 3.44-3.38 (m, 4H), 3.18 (quintet, J=8.4 Hz, 1H), 2.90-2.80 (m, 1H), 2.70-2.60 (m, 1H), 2.38 (s, 3H), 1.27 (d, J=6.4 Hz, 3H), 1.11 (d, J=7.2 Hz, 3H).

Example 8

TES-Protected N-Methyl Thiazole CP Intermediate 26

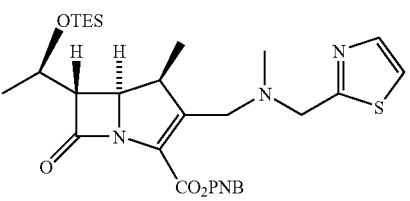

Method A; Percent yield: 77%; ¹H NMR (CDCl₃, 300 MHz): δ 8.22 (d, J=7.8 Hz, 2H), 7.71 (d, J=4.2 Hz, 1H), 7.67 (d, J=9.0 Hz, 2H), 7.30 (d, J=3.0 Hz, 1H), 5.46 (d, J=13.8 Hz, 1H), 5.23 (d, J=13.8 Hz, 1H), 4.27-4.22 (m, 1H), 4.19 (dd, J=10.2; 3.0 Hz, 1H), 4.02 (d, J=14.7 Hz, 1H), 3.93 (d, J=15.0 Hz, 1H), 3.80 (d, J=15.0 Hz, 1H), 3.46-3.38 (m, 1H), 3.29-3.23 (m, 2H), 2.33 (s, 3H), 1.26 (d, J=5.7 Hz, 3H), 1.17 (d, J=7.2 Hz, 3H), 0.94 (t, J=8.4 Hz, 9H), 0.60 (q, J=7.8 Hz, 6H).

PNB-Protected N-Methyl Thiazole CP Intermediate 27

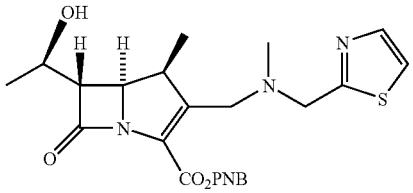

27

Method E; Percent yield: 98%; $^1$H NMR (CDCl$_3$, 300 MHz): δ 8.14 (d, J=6.3 Hz, 2H), 7.64 (d, J=3.6 Hz, 1H), 7.59 (d, J=8.7 Hz, 2H), 7.25 (d, J=3.0 Hz, 1H), 5.43 (d, J=13.5 Hz, 1H), 5.16 (d, J=13.5 Hz, 1H), 4.20 (dd, J=9.6; 3.0 Hz, 2H), 3.96 (d, J=14.7 Hz, 1H), 3.87 (d, J=15.3 Hz, 1H), 3.75 (d, J=15.3 Hz, 1H), 3.48-3.30 (m, 2H), 3.26-3.19 (m, 2H), 2.26 (s, 3H), 1.28 (d, J=6.0 Hz, 3H), 1.12 (d, J=7.5 Hz, 3H).

N-Methyl Thiazole CP Analog 28

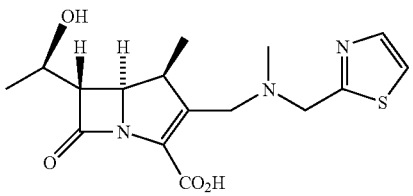

28

Percent yield: 54%; $^1$H NMR (D$_2$O, 400 MHz): δ 7.76 (d, J=3.6 Hz, 1H), 7.60 (d, J=3.6 Hz, 1H), 4.22 (d, J=14.0 Hz, 1H), 4.17 (quint, J=6.4 Hz, 1H), 4.11 (dd, J=10.0; 3.2 Hz, 1H), 4.04 (d, J=14.4 Hz, 1H), 3.80 (d, J=14.4 Hz, 1H), 3.45 (d, J=14.4 Hz, 1H), 3.36 (dd, J=6.4; 2.8 Hz, 1H), 3.20-3.15 (m, 1H), 2.44 (s, 3H), 1.22 (d, J=6.4 Hz, 3H), 1.01 (d, J=7.6 Hz, 3H).

Example 9

TES-Protected Pyrrolidine CP Intermediate 29

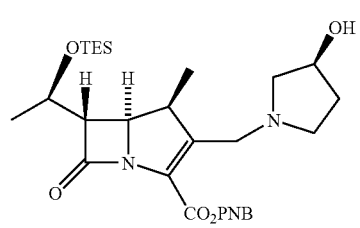

29

Method D; Percent yield: 69%; $^1$H NMR (CDCl$_3$, 300 MHz): δ 8.16 (d, J=8.1 Hz, 2H), 7.63 (d, J=9.3 Hz, 2H), 5.41 (d, J=14.1 Hz, 1H), 5.18 (d, J=14.1 Hz, 1H), 4.29-4.19 (m, 2H), 4.16 (dd, J=10.2; 2.4 Hz, 1H), 3.84 (d, J=14.1 Hz, 1H), 3.36-3.29 (m, 2H), 3.20 (dd, J=4.8 Hz; 2.7 Hz, 1H), 2.85-2.78 (m, 1H), 2.73 (br s, 1H), 2.60 (d, J=2.7 Hz, 2H), 2.28-2.08 (m, 2H), 1.72-1.66 (m, 1H), 1.22 (d, J=5.7 Hz, 3H), 1.13 (d, J=7.5 Hz, 3H), 0.90 (t, J=7.2 Hz, 9H), 056 (q, J=7.8 Hz, 6H).

Pyrrolidine CP Analog 30

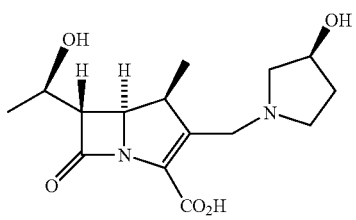

30

Method F; Percent yield: 60% (from 29); $^1$H NMR (D$_2$O, 300 MHz): δ 4.67-4.64 (m, 1H), 4.22-4.14 (m, 2H), 4.07 (d, J=14.4 Hz, 1H), 3.94 (d, J=14.4 Hz, 1H), 3.50 (br s, 1H), 3.42 (dd, J=6.3; 3.0 Hz, 1H), 3.35-3.10 (m, 4H), 2.31-2.21 (m, 1H), 2.02-1.93 (m, 1H), 1.22 (d, J=6.3 Hz, 3H), 1.12 (d, J=7.5 Hz, 3H).

Example 10

TES-Protected Prolineamide CP Intermediate 31

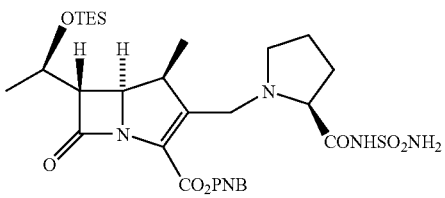

31

Method D; Percent yield: 85%; $^1$H NMR (CDCl$_3$, 300 MHz): δ 8.16 (d, J=8.4 Hz, 2H), 7.62 (d, J=8.7 Hz, 2H), 7.02 (d, J=4.5 Hz, 1H), 6.68 (d, J=4.5 Hz, 1H), 5.40 (d, J=14.1 Hz, 1H), 5.19 (d, J=14.1 Hz, 1H), 4.24-4.17 (m, 2H), 4.06 (d, J=14.4 Hz, 1H), 3.35-3.20 (m, 3H), 3.06 (dd, J=9.3; 4.8 Hz, 1H), 3.00-2.96 (m, 1H), 2.29-2.12 (m, 2H), 1.91-1.81 (m, 1H), 1.78-1.67 (m, 2H), 1.21 (d, J=6.6 Hz, 3H), 1.12 (d, J=7.5 Hz, 3H), 0.89 (t, J=8.4 Hz, 9H), 055 (q, J=8.4 Hz, 6H).

Prolineamide CP Analog 32

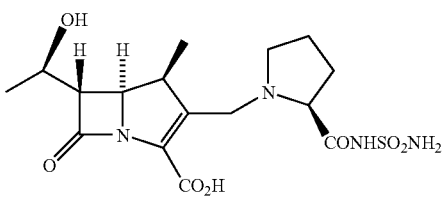

32

Method F; Percent yield: 26% (from 31); $^1$H NMR (D$_2$O, 300 MHz): δ 4.22-4.12 (m, 2H), 3.89 (d, J=13.8 Hz, 1H), 3.65-3.53 (m, 2H), 3.42-3.20 (m, 3H), 2.68-2.53 (m, 1H), 2.40-2.23 (m, 1H), 1.98-1.75 (m, 3), 1.22 (d, J=5.7 Hz, 3H), 1.06 (d, J=7.5 Hz, 3H).

Example 11

TES-Protected Piperazine CP Intermediate 33

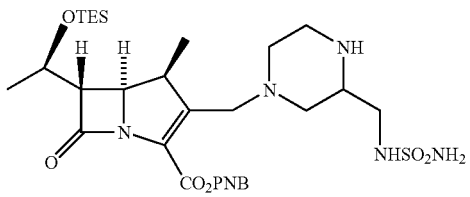

Method D; Percent yield: 37%; $^1$H NMR (CDCl$_3$, 300 MHz): δ 8.20 (d, J=8.1 Hz, 2H), 7.66 (d, J=9.3 Hz, 1H), 5.43 (d, J=14.1 Hz, 1H), 5.22 (d, J=14.1 Hz, 1H), 4.97 (br s, 1H), 4.28-4.20 (m, 2H), 3.79 (d, J=14.1 Hz, 1H), 3.34-2.94 (m, 7H), 2.89-2.82 (m, 1H), 2.65-2.60 (m, 1H), 2.26 (t, J=9.9 Hz, 1H), 1.85 (t, J=10.2 Hz, 1H), 1.24 (d, J=6.3 Hz, 3H), 1.15 (d, J=7.8 Hz, 3H), 0.93 (t, J=8.4 Hz, 9H), 0.59 (q, J=8.1 Hz, 6H).

Piperazine CP Analog 34

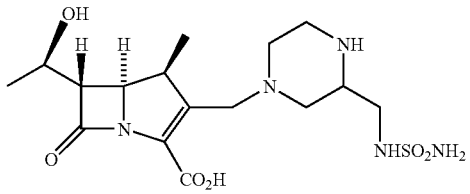

Method F; Percent yield: 58% (from 33); $^1$H NMR (D$_2$O, 300 MHz): δ 4.20-4.10 (m, 2H), 3.70 (d, J=13.8 Hz, 1H), 3.45-3.36 (m, 2H), 3.23-2.89 (m, 8H), 2.53 (t, J=10.8 Hz, 1H), 2.10 (t, J=10.5 Hz, 1H), 1.20 (d, J=6.0 Hz, 3H), 1.05 (d, J=7.5 Hz, 3H).

Example 12

TES-Protected Piperazine CP Intermediate 35

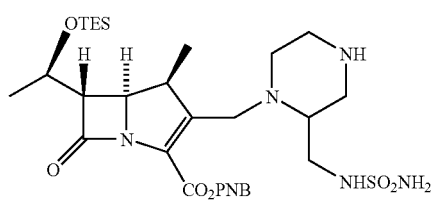

Method D; Percent yield: 13%; $^1$H NMR (CDCl$_3$, 300 MHz): δ 8.19 (d, J=8.4 Hz, 2H), 7.65 (d, J=8.1 Hz, 2H), 6.40 (br s, 4H), 5.40 (d, J=14.1 Hz, 1H), 5.21 (d, J=14.1 Hz, 1H), 4.26-4.18 (m, 2H), 3.37 (d, J=14.1 Hz, 1H), 3.49-3.39 (m, 3H), 3.26-3.00 (m, 5H), 2.94-2.90 (m, 1H), 2.78-2.74 (m, 1H), 2.52-2.42 (m, 1H), 1.22 (d, J=6.9 Hz, 3H), 1.15 (d, J=6.0 Hz, 3H), 0.92 (t, J=8.4 Hz, 9H), 0.57 (q, J=7.8 Hz, 6H).

Piperazine CP Analog 36

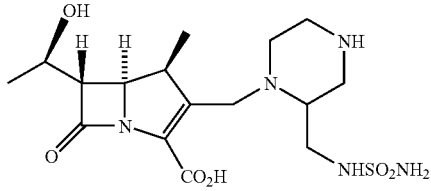

Method F; Percent yield: 63% (from 35); $^1$H NMR (D$_2$O, 300 MHz): δ 4.18-4.10 (m, 2H), 3.72 (d, J=14.4 Hz, 1H), 3.43-3.35 (m, 2H), 3.21-2.88 (m, 8H), 2.36-2.27 (m, 2H), 1.20 (d, J=6.0 Hz, 3H), 1.05 (d, J=7.2 Hz, 3H).

Example 13

TES-Protected Prolineamide CP Intermediate 37

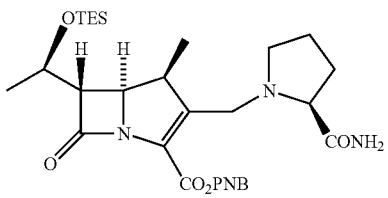

Method D; Percent yield: 91%; $^1$H NMR (CDCl$_3$, 300 MHz): δ 8.23 (d, J=9.0 Hz, 2H), 7.67 (d, J=9.0 Hz, 2H), 7.06 (br s, 1H), 5.46 (d, J=13.8 Hz, 1H), 5.24 (d, J=13.8 Hz, 1H), 5.43 (br s, 1H), 4.30-4.22 (m, 2H), 4.17-4.07 (m, 2H), 3.38-3.24 (m, 2H), 3.14 (dd, J=9.9; 6.0 Hz, 1H), 3.05-3.01 (m, 1H), 2.36-2.19 (m, 2H), 1.98-1.72 (m, 3H), 1.26 (d, J=6.3 Hz, 3H), 1.17 (d, J=7.5 Hz, 3H), 0.95 (t, J=8.1 Hz, 9H), 0.61 (q, J=8.1 Hz, 6H).

PNB-Protected Prolineamide CP Intermediate 38

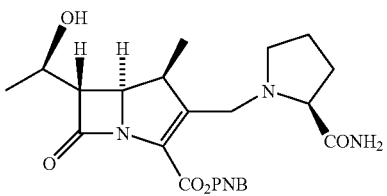

Method E; Percent yield: 96%; $^1$H NMR (acetone-d$_6$, 300 MHz): δ 8.23 (d, J=9.0 Hz, 2H), 7.80 (d, J=9.0 Hz, 2H), 7.19 (br s, 1H), 6.45 (br s, 1H0, 5.52 (d, J=14.1 Hz, 1H), 5.31 (d, J=14.1 Hz, 1H), 4.25 (dd, J=9.9; 3.6 Hz, 1H), 4.06-3.99 (m, 2H), 3.62-3.52 (m, 1H), 3.37-3.29 (m, 2H), 3.06-2.87 (m, 3H), 2.28-2.10 (m, 2H), 1.86-1.72 (m, 3H), 1.24 (d, J=7.2 Hz, 3H), 1.18 (d, J=7.2 Hz, 3H).

Prolineamide CP Analog 39

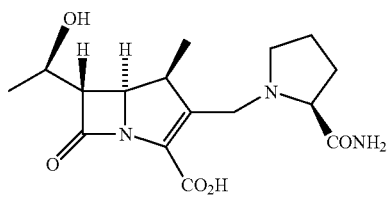

Percent yield: 62%; $^1$H NMR (D$_2$O, 300 MHz): δ 4.24-4.16 (m, 2H), 4.04 (d, J=14.1 Hz, 1H), 3.92-3.80 (m, 2H), 3.53-3.50 (m, 1H), 3.44-3.41 (m, 1H), 3.30-3.20 (m,1H), 2.91-2.82 (m,1H), 2.50-2.40 (m, 1H), 2.07-1.93 (m, 3H), 1.24 (d, J=6.0 Hz, 3H), 1.10 (d, J=6.9 Hz,3H).

Example 14

TES-Protected N-Methyl-2-Pyridylethyl CP Intermediate 40

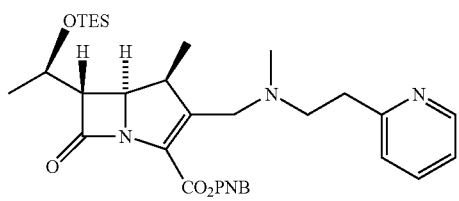

Method A; Percent yield: 84%; $^1$H NMR (CDCl$_3$, 300 MHz): δ 8.48 (d, J=3.9 Hz, 1H), 8.17 (d, J=8.7 Hz, 2H), 7.63 (d, J=9.3 Hz, 2H), 7.55 (dt, J=7.8; 1.5 Hz, 1H), 7.13-7.06 (m, 2H), 5.42 (d, J=13.8 Hz, 1H), 5.19 (d, J=13.8 Hz, 1H), 4.20 (quintet, J=6.0 Hz, 1H), 4.07 (dd, J=10.5; 3.0 Hz, 1H), 3.85 (d, J=14.7 Hz, 1H), 3.18-3.00 (m, 3H), 2.94-2.76 (3H), 2.68-2.60 (m, 1H), 2.24 (s, 3H), 1.22 (d, J=6.6 Hz, 3H), 0.99 (d, J=6.6 Hz, 3H), 0.92 (t, J=8.4 Hz, 9H), 0.57 (q, J=8.4 Hz, 6H).

PNB-Protected N-Methyl-2-Pyridylethyl CP Intermediate 41

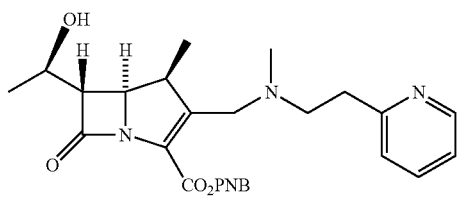

Method E; Percent yield: 82%; $^1$H NMR (CDCl$_3$, 300 MHz): δ 8.49 (d, J=5.1 Hz, 1H), 8.18 (d, J=9.0 Hz, 2H), 7.63 (d, J=8.4 Hz, 2H), 7.16-7.09 (m, 2H), 5.46 (d, J=13.8 Hz, 2H), 5.19 (d, J=13.8 Hz, 2H), 4.23 (m, 1H), 4.15 (dd, J=9.1; 3.0 Hz, 1H), 3.87 (d, J=15.3 Hz, 1H), 3.60 (br s, 1H), 3.22 (dd, J=6.0; 3.0 Hz, 1H), 3.18-3.10 (m, 2H), 2.96-2.77 (m, 3H), 2.69-2.60 (m, 1H), 2.26 (s, 3H), 1.31 (d, J=6.3 Hz, 3H), 1.02 (d, J=6.3 Hz, 3H).

N-Methyl-2-Pyridylethyl CP Analog 42

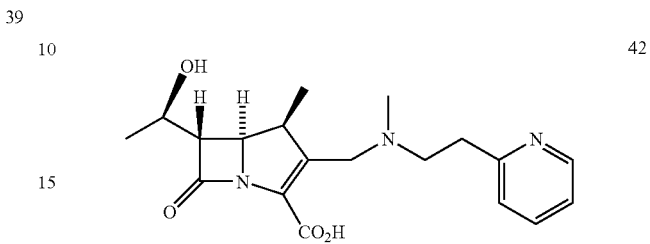

Percent yield: 89%; $^1$H NMR (D$_2$O, 400 MHz): δ 8.45 (dd, J=5.2; 0.8 Hz, 1H), 7.82 (dt, J=7.6; 2.0 Hz, 1H), 7.38 (d, J=8.0 Hz, 1H), 4.26-4.20 (m, 2H), 4.00 (d, J=14.8 Hz, 1H), 3.93 (d, J=14.8 Hz, 1H), 3.61-3.53 (m, 1H), 3.52-3.46 (m, 2H), 3.24 (t, J=6.8 Hz, 2H), 3.21-3.14 (m, 1H), 2.92 (s, 3H), 1.28 (d, J=6.4 Hz, 3H), 1.18 (d, J=7.2 Hz, 3H).

Example 15

TES-Protected N-Methyl-2-Pyridylmethyl CP Intermediate 43

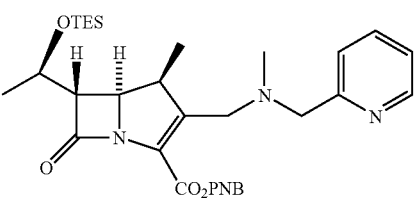

Method A; Percent yield: 63%; $^1$H NMR (CDCl$_3$, 300 MHz): δ 8.55 (d, J=3.9 Hz, 1H), 8.22 (d, J=8.7 Hz, 2H), 7.68-7.62 (m, 3H), 7.38 (d, J=8.4 Hz, 1H), 7.18 (dd, J=6.6; 5.1 Hz, 1H), 5.46 (d, J=13.8 Hz, 1H), 5.23 (d, J=13.8 Hz, 1H), 4.23 (quintet, J=6.0 Hz, 1H), 4.14 (dd, J=10.2; 2.7 Hz, 1H), 3.92 (d, J=14.7 Hz, 1H), 3.78 (d, J=13.2 Hz, 1H), 3.53 (d, J=13.2 Hz, 1H), 3.48-3.39 (m, 1H), 3.22-3.16 (m,1H), 2.28 (s, 3H), 1.25 (d, J=5.7 Hz, 3H), 1.07 (d, J=7.2 Hz, 3H), 0.94 (t, J=7.8 Hz, 9H), 0.59 (q, J=8.1 Hz, 6H).

PNB-Protected N-Methyl-2-Pyridylmethyl CP Intermediate 44

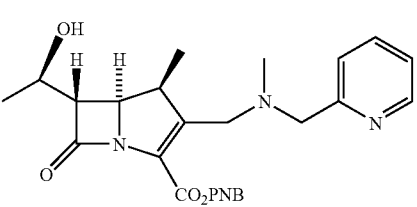

Method E; Percent yield: 70%; $^1$H NMR (CDCl$_3$, 300 MHz): δ 8.55 (d, J=4.5 Hz, 1H), 8.22 (d,J=8.7 Hz, 2H), 7.66 (d, J=8.4 Hz, 2H), 7.38 (d, J=7.2 Hz, 2H), 7.18 (dd, J=6.6; 6.0 Hz, 1H), 5.50 (d, J=14.1 Hz, 1H), 5.22 (d, J=14.1 Hz, 1H), 4.26 (quintet, J=7.2 Hz, 1H), 4.19 (dd, J=9.9; 3.0 Hz, 1H), 3.94 (d, J=14.4 Hz, 1H), 3.79 (d, J=13.2 Hz, 1H), 3.54 (d, J=13.2 Hz, 1H), 3.52-3.42 (m, 2H), 3.27-3.19 (m, 2H), 2.28 (s, 3H), 1.34 (d, J=6.3 Hz, 3H), 1.09 (d, J=7.2 Hz, 3H).

N-Methyl-2-Pyridylmethyl CP Analog 45

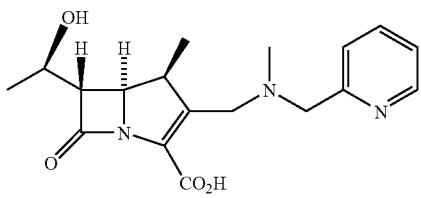

Percent yield: 76%; $^1$H NMR (D$_2$O, 400 MHz): δ 8.58 (d, J=4.8 Hz, 1H), 7.91 (dt, J=7.6; 1.6 Hz, 1H), 7.52 (d, J=8.0 Hz, 1H), 7.49-7.46 (m, 1H), 4.36 (d, J=13.6 Hz, 1H), 4.26 (d, J=13.2 Hz, 1H), 4.21-4.17 (m, 1H), 4.09-4.03 (m, 2H), 3.97 (d, J=14.4 Hz, 1H), 3.42-3.40 (m, 1H), 3.19-3.11(m,1H), 2.76 (s, 1H), 1.24 (d, J=6.4 Hz, 3H), 1.10 (d, J=7.6 Hz, 3H).

Example 16

TES-Protected N-Methyl Pyrazine CP Intermediate 46

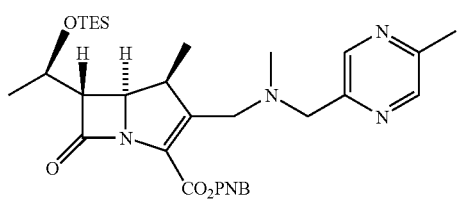

Method A; Percent yield: 87%; $^1$H NMR (CDCl$_3$, 300 MHz): δ 8.45 (s, 1H), 8.32 (s, 1H), 8.14 (d, J=8.1 Hz, 2H), 7.61 (d, J=9.0 Hz, 2H), 5.40 (d, J=13.8 Hz, 1H), 5.16 (d, J=13.8 Hz, 1H), 4.18 (quintet, J=6.0 Hz, 1H), 4.10 (dd, J=5.1; 3.0 Hz, 1H), 3.88 (d, J=14.7 Hz, 1H), 3.69 (d, J=13.8 Hz, 1H), 3.48 (d, J=13.2 Hz, 1H), 3.40-3.29 (m, 1H), 3.18-3.10 (m, 2H), 2.47 (s, 3H), 2.21 (s, 3H), 1.18 (d, J=5.1 Hz, 3H), 1.03 (d, J=7.2 Hz, 3H), 0.87 (t, J=8.1 Hz, 9H), 0.53 (q, J=8.4 Hz, 6H).

PNB-Protected N-Methyl Pyrazine CP Intermediate 47

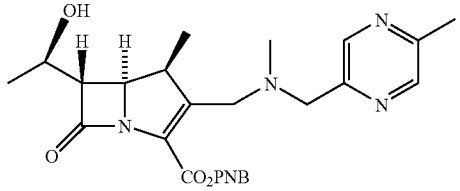

Method E; Percent yield: 92%; $^1$H NMR (CDCl$_3$, 300 MHz): δ 8.47 (s, 1H), 8.35 (s, 1H), 8.15 (d, J=9.0 Hz, 2H), 7.60 (d, J=9.0 Hz, 2H), 5.44 (d, J=13.8 Hz, 1H), 5.17 (d, J=13.8 Hz, 1H), 4.23-4.15 (m, 2H), 3.89 (d, J=15.0 Hz, 1H), 3.71 (d, J=13.8 Hz, 1H), 3.50 (d, J=15.0 Hz, 1H), 3.44-3.36 (m, 1H), 3.23 (dd, J=6.0; 2.7 Hz, 1H), 3.15 (d, J=15.0 Hz, 1H), 2.50 (s, 3H), 2.22 (s.3H), 1.27 (d, J=5.4 Hz, 3H), 1.05 (d, J=6.9 Hz, 3H).

N-Methyl Pyrazine CP Analog 48

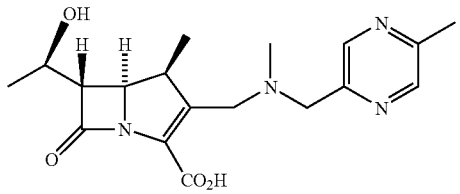

Percent yield: 63%; $^1$H NMR (D$_2$O, 400 MHz): δ 8.52 (s, 1H), 8.47 (s, 1H), 4.19-4.13 (m, 2H), 4.06-4.00 (m, 2H), 3.93 (d, J=14.4 Hz, 1H), 3.69 (d, J=14.4 Hz, 1H), 3.37-3.35 (m, 1H), 3.16-3.08 (m, 1H), 2.57 (s, 3H), 2.52 (s, 3H), 1.21 (d, J=6.4 Hz, 3H), 1.03 (d, J=7.2 Hz, 3H).

Example 17

TES-Protected N-Ethyl-4-Pyridylmethyl CP Intermediate 49

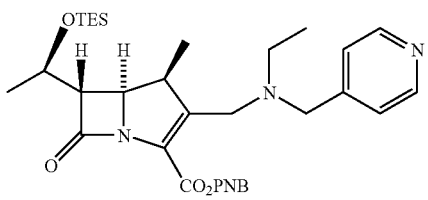

Method A; Percent yield: 92%; $^1$H NMR (CDCl$_3$, 300 MHz): δ 8.54 (d, J=5.7 Hz, 2H), 8.22 (d, J=8.1 Hz, 2H), 7.67 (d, 8.4 Hz, 2H), 7.26 (d, J=5.1 Hz, 2H), 5.46 (d, J=13.8 Hz, 1H), 5.23 (d, J=13.8 Hz, 1H), 4.24 (quintet, J=6.0 Hz, 1H), 4.16-4.06 (m, 2H), 3.96 (d, J=15.3 Hz, 1H), 3.72 (d, J=14.4

Hz, 1H), 3.37-3.14 (m, 4H), 2.62-2.55 (m, 1H), 2.42-2.33 (m, 1H), 2.04 (s, 3H), 1.24 (d, J=6.3 Hz, 3H), 1.08-1.05 (m, 6H), 0.93 (t, J=8.1 Hz, 9H),)59 (q, J=8.4 Hz, 6H).

PNB-Protected N-Ethyl-4-Pyridylmethyl CP Intermediate 50

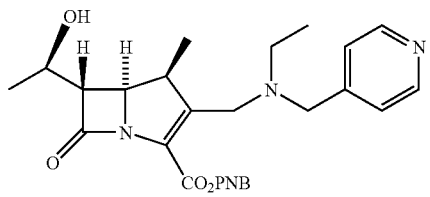

Method E; Percent yield: 91%; $^1$H NMR (CDCl$_3$, 300 MHz): δ 8.55 (d, J=6.3 Hz, 2H), 8.23 (d, J=9.0 Hz, 2H), 7.67 (d, J=9.0 Hz, 2H), 7.29 (d, J=5.7 Hz, 2H), 5.50 (d, J=13.2 Hz, 1H), 5.27 (d, J=13.2 Hz, 1H), 4.26 (quintet, J=6.9 Hz, 1H), 4.18-4.11 (m, 1H), 3.97 (d, J=14.4 Hz, 1H), 3.73 (d, J=14.4 Hz, 1H), 3.42-3.31 (m, 2H), 3.26 (dd, J=7.2; 3.3 Hz, 1H), 3.18 (d, J=14.4 Hz, 1H), 3.65-3.54 (m, 1H), 2.45-2.35 (m, 1H), 2.30 (br s, 1H), 1.35 (d, J=7.5 Hz, 3H), 1.10-1.05 (m, 6H).

N-Ethyl-4-Pyridylmethyl CP Analog 51

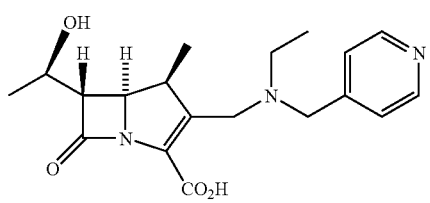

Percent yield: 81%; $^1$H NMR (D$_2$O, 400 MHz): δ 8.54 (d, J=4.8 Hz, 2H), 7.45 (d, J=4.8 Hz, 2H), 4.26 (d, J=13.6 Hz, 1H), 4.19-4.13 (m, 1H), 4.09 (d, J=13.6 Hz, 1H), 3.99 (d, J=9.2 Hz, 1H), 3.94-3.85 (m, 2H), 3.37-3.35 (m, 1H), 3.15-2.97 (m, 3H), 1.24 (t, J=7.2 Hz, 3H), 1.21 (d, J=6.4 Hz, 3H), 1.05 (d, J=7.2 Hz, 3H).

Example 18

TES-Protected Pyridylthiazole CP Intermediate 52

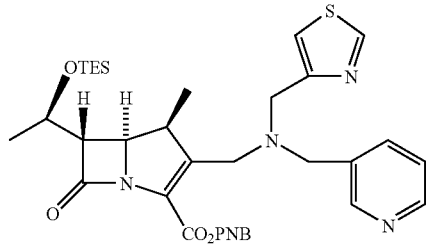

Method A; Percent yield: 83%; $^1$H NMR (CDCl$_3$, 300 MHz): δ 8.57 (s, 1H), 8.52 (dd, J=4.8; 1.2 Hz, 1H), 8.22 (d, J=8.7 Hz, 2H), 7.69-7.61 (m, 3H), 7.26 (m 1H), 5.47 (d, J=14.1 Hz, 1H), 5.23 (d, J=14.1 Hz, 1H), 4.25 (quintet, J=5.7 Hz, 1H), 4.17 (dd, J=10.2; 2.7 Hz, 1H), 3.86 (d, J=14.4 Hz, 1H), 3.63 (d, J=13.5 Hz, 1H), 3.43-3.31 (m, 2H), 3.23 (dd, J=5.1; 3.3 Hz, 1H), 3.16 (d, J=14.4 Hz, 1H), 2.19 (s, 3H), 1.25 (d, J=6.3 Hz, 3H), 1.07 (d, J=7.5 Hz, 3H), 0.94 (t, J=7.5 Hz, 9H), 0.60 (q, J=8.4 Hz, 6H).

PNB-Protected Pyridylthiazole CP Intermediate 53

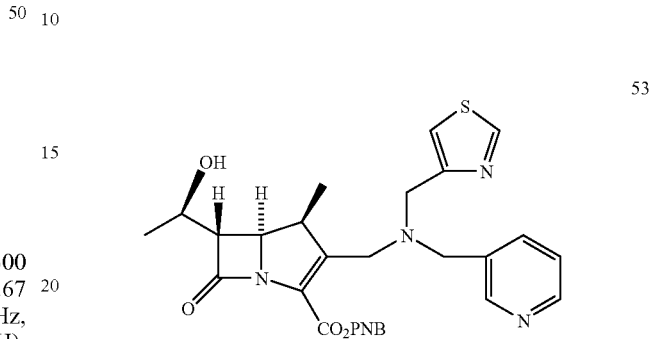

Method E; Percent yield: 69%; $^1$H NMR (CDCl$_3$, 300 MHz): δ 8.74 (d, J=2.1 Hz, 1H), 8.46 (d, J=5.1 Hz, 1H), 8.11 (d, J=8.4 Hz, 2H), 7.63-7.57 (m, 3H), 7.42 (d, J=8.7 Hz, 1H), 7.19 (d, J=1.8 Hz, 1H), 7.11 (dd, J=5.4; 4.8 Hz, 1H), 5.40 (d, J=13.8 Hz, 1H), 5.14 (d, J=13.8 Hz, 1H), 4.18-3.97 (m, 3H), 3.86 (d, J=14.4 Hz, 2H), 3.72 (br s, 1H), 3.66 (d, J=13.8 Hz, 1H), 3.56 (d, J=14.4 Hz, 1H), 3.48-3.37 (m, 1H), 3.20-3.13 (m, 2H), 1.23 (d, J=6.3 Hz, 3H), 0.82 (d, J=7.5 Hz, 3H).

Pyridylthiazole CP Analog 54

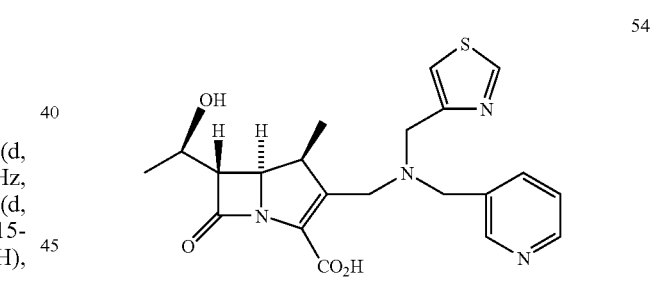

Percent yield: 32%; $^1$H NMR (D$_2$O, 400 MHz): δ 8.90 (s, 1H), 8.42 (d, J=4.4 Hz, 1H), 7.78 (t, J=8.0 Hz, 1H), 7.49 (s, 1H), 7.43 (d, J=7.6 Hz, 1H), 7.32 (t, J=6.0 Hz, 1H), 4.10-3.86 (m, 6H), 3.77 (d, J=9.6 Hz, 1H), 3.39 (d, J=14.8 Hz, 1H), 3.21-3.19 (m, 1H), 3.06 (quin, J=8.0 Hz, 1H), 1.16 (d, J=5.7 Hz, 3H), 0.73 (d, J=5.4 Hz, 3H).

Preparation of Thioguanidine Analogs 62 and 63.

Discussion:

The following two examples of thioguanidine-substituted CP analogs were prepared via the procedure described in Scheme 3. Alcohol intermediates 55 and 58 were isolated and converted to their corresponding mesylates, 56 and 59, under standard conditions. The mesylates were then allowed to react with thiourea in dry DMF to afford the O-TES, N-PNB-protected thioguanidine intermediates 57 and 60. Deprotection was accomplished by following the two step protocol previously described.

55

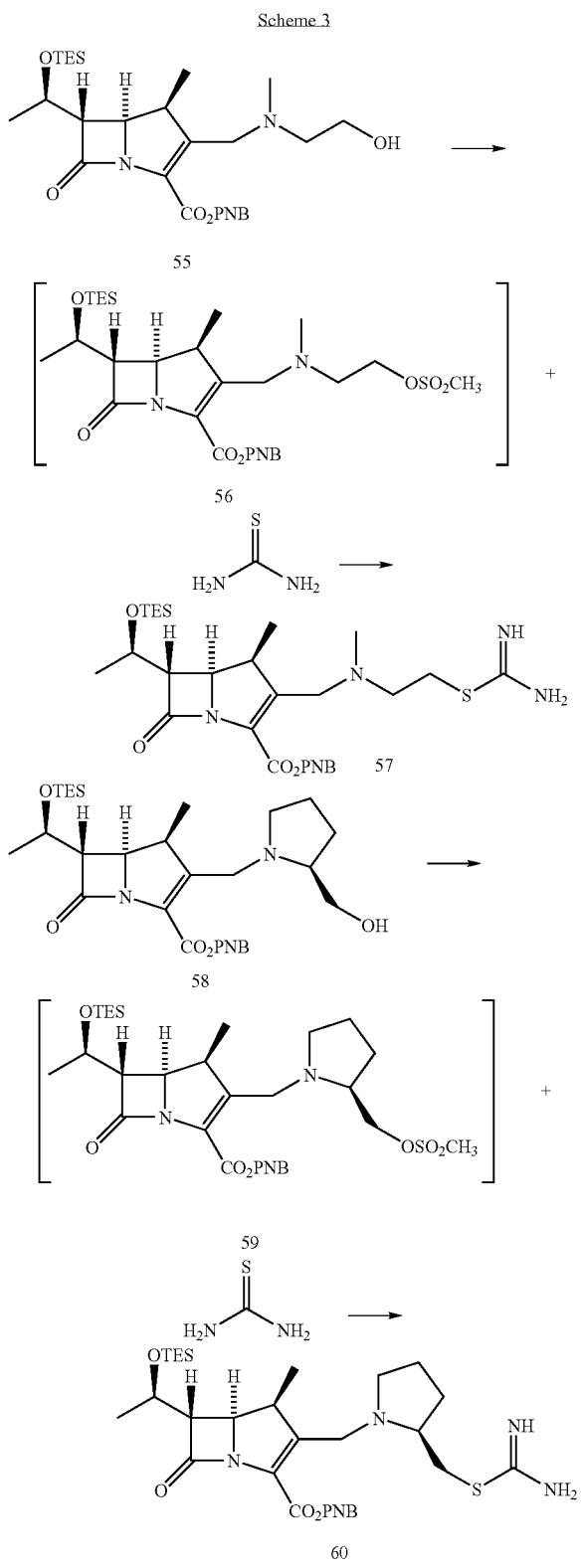

Step I: General Procedure for Mesylate Formation

Methanesulfonyl chloride (1.3 mmol) and triethylamine (1.5 mmol) were added at 0° C. under nitrogen atmosphere to a solution of alcohol intermediate 55 or 58 (1.0 mmol) in dry DCM (15 mL). The reaction mixture was stirred at 0° C. for 1 h and then at 5° C. for 15 minutes (monitoring by TLC). The reaction mixture was then washed with aq. NaHCO$_3$, water, brine, and dried over Na$_2$SO$_4$. Evaporation of the solvent gave crude mesylate, which was immediately used without purification.

Step II: General Procedure for Mesylate Displacement by Amine Sidechains

To a solution of freshly prepared mesylate (1.0 mmol) in dry DMF (15 mL) at 0° C. under N$_2$ atmosphere was added a solution of thiourea (1.5 mmol) in dry DMF (3 mL) and the resulting mixture was stirred at 0° C. for 1 h and then allowed to warm to rt and stirred overnight (monitored by TLC). The reaction mixture was then evaporated under reduced pressure and residue was purified by flash chromatography. The last two deprotection steps were performed as previously described.

Example 19

TES-Protected N-Methyl Hydroxyethyl CP Intermediate 55

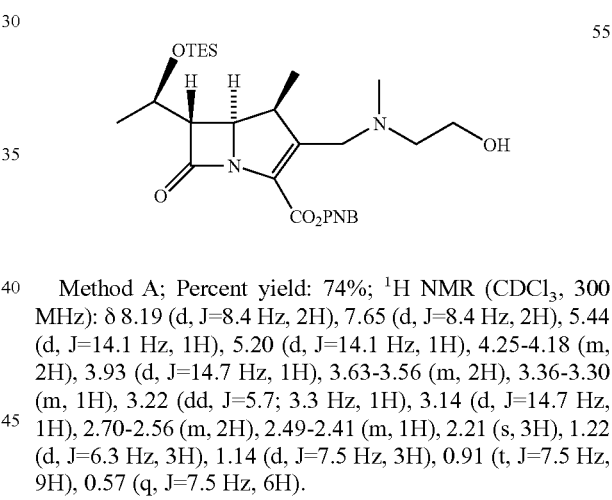

Method A; Percent yield: 74%; $^1$H NMR (CDCl$_3$, 300 MHz): δ 8.19 (d, J=8.4 Hz, 2H), 7.65 (d, J=8.4 Hz, 2H), 5.44 (d, J=14.1 Hz, 1H), 5.20 (d, J=14.1 Hz, 1H), 4.25-4.18 (m, 2H), 3.93 (d, J=14.7 Hz, 1H), 3.63-3.56 (m, 2H), 3.36-3.30 (m, 1H), 3.22 (dd, J=5.7; 3.3 Hz, 1H), 3.14 (d, J=14.7 Hz, 1H), 2.70-2.56 (m, 2H), 2.49-2.41 (m, 1H), 2.21 (s, 3H), 1.22 (d, J=6.3 Hz, 3H), 1.14 (d, J=7.5 Hz, 3H), 0.91 (t, J=7.5 Hz, 9H), 0.57 (q, J=7.5 Hz, 6H).

TES-Protected N-Methyl Thioguanidine CP Intermediate 57

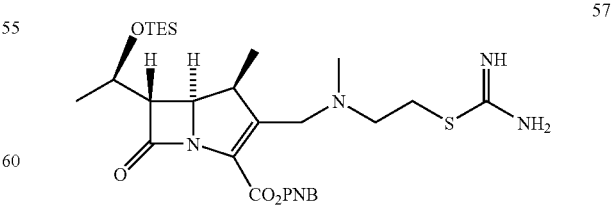

Percent yield: 54%; $^1$H NMR (CDCl$_3$, 300 MHz): δ 9.21 (br s, 3H), 8.18 (d, J=7.8 Hz, 2H), 7.65 (d, J=8.4 Hz, 2H), 5.42 (d, J=14.1 Hz, 1H), 5.21 (d, J=14.1 Hz, 1H), 4.28-4.23 (m, 2H), 4.06 (d, J=14.7 Hz, 1H), 3.26-3.11 (m, 5H), 2.82-2.73

(m, 2H), 2.26 (s, 3H), 1.22 (d, J=6.3 Hz, 3H), 1.13 (d, J=7.5 Hz, 3H), 0.91 (t, J=7.5 Hz, 9H), 057 (q, J=7.5 Hz, 6H).

PNB-Protected N-Methyl Thioguanidine CP Intermediate 61

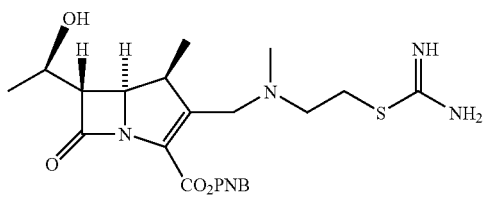

Method E; Percent yield: 90%; ¹H NMR (acetone-d₆, 300 MHz): δ 9.60 (br s, 1H), 8.61 (br s, 2H), 8.22 (d, J=8.4 Hz, 2H), 7.79 (d, J=8.4 Hz, 2H), 5.52 (d, J=14.1 Hz, 1H), 5.30 (d, J=14.1 Hz, 1H), 4.29 (dd, J=10.5; 3.0 Hz, 1H), 4.16-4.08 (m, 1H), 4.03 (d, J=14.7 Hz, 1H), 3.48-3.31 (m, 5H), 2.94-2.87 (m, 2H), 2.33 (s, 3H), 1.23 (d, J=7.2 Hz, 3H), 1.19 (d, J=7.2 Hz, 3H).

N-Methyl Thioguanidine CP Analog 62

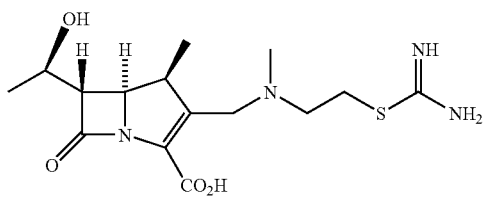

Percent yield: 20%; ¹H NMR (D₂O, 300 MHz): δ 4.20-4.13 (m, 2H), 3.80 (d, J=13.8 Hz, 1H), 3.51 (d, J=13.8 Hz, 1H), 3.40-3.39 (m, 1H), 3.32-3.30 (m, 2H), 3.18-3.12 (m, 1H), 3.09-2.92 (m, 2H), 2.47 (s, 3H), 1.22 (d, J=6.9 Hz, 3H), 1.07 (d, J=7.2 Hz, 3H).

Example 20

TES-Protected Prolinol CP Intermediate 58

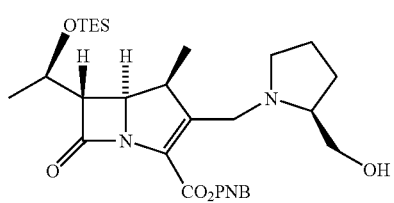

Method D; Percent yield: 66%; ¹H NMR (CDCl₃, 300 MHz): δ 8.20 (d, J=9.3 Hz, 2H), 7.66 (d, J=8.4 Hz, 2H), 5.45 (d, J=14.1 Hz, 1H), 5.22 (d, J=14.1 Hz, 1H), 4.27-4.19 (m, 1H), 4.21 (dd, J=11.4; 3.9 Hz, 1H), 3.96 (d, J=15.0 Hz, 1H), 3.65 (dd, J=11.1; 4.2 Hz, 1H), 3.47-3.41 (m, 1H), 3.39-3.32 (m, 2H), 3.24 (dd, J=4.8; 2.7 Hz, 1H), 3.00-2.94 (m, 1H), 2.70-2.65 (m, 1H), 2.54 (br s, 1H), 2.27-2.18 (m, 1H), 1.98-1.63 (m, 4H), 1.25 (d, J=6.0 Hz, 3H), 1.15 (d, J=7.2 Hz, 3H), 0.93 (t, J=7.2 Hz, 9H), 0.59 (q, J=7.5 Hz, 6H).

TES-Protected Thioguanidine CP Intermediate 60

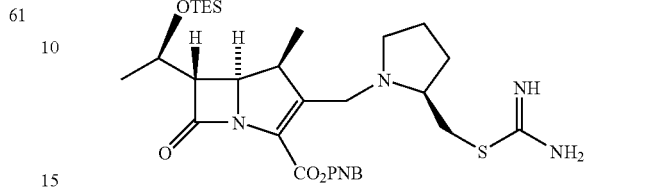

Percent yield: 43%; ¹H NMR (CDCl₃, 300 MHz): δ 9.33 (br s, 2H), 8.20 (d, J=9.3 Hz, 2H), 7.67 (d, J=8.7 Hz, 2H), 5.43 (d, J=14.1 Hz, 2H), 5.25 (d, J=14.1 Hz, 2H), 4.30-4.19 (m, 3H), 3.50-3.34 (m, 2H), 3.27-3.25 (m, 1H), 3.20-3.07 (m, 3H), 2.95-2.90 (m, 1H), 2.45-2.35 (m, 1H), 2.10-1.98 (m, 1H), 1.85-1.70 (m, 3H), 1.21 (d, J=6.9 Hz, 3H), 1.17 (d, J=7.8 Hz, 3H), 0.92 (t, J=8.4 Hz, 9H), 0.58 (q, J=8.4 Hz, 6H).

Thioguanidine CP Analog 63

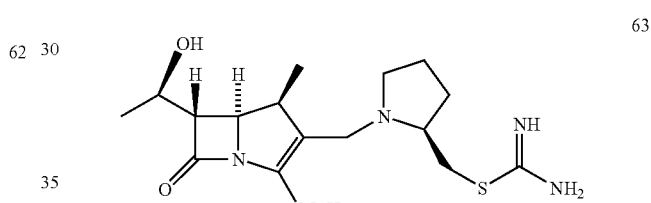

Method F; Percent yield: 15% (from 60); ¹H NMR (D₂O, 400 MHz): δ 4.24-4.20 (m, 1H), 4.18 (dd, J=9.6; 2.8 Hz, 1H), 3.83 (d, J=13.2 Hz, 1H), 3.46 (d, J=13.2 Hz, 1H), 3.41 (dd, J=6.4; 2.8 Hz, 1H), 3.33-3.26 (m, 2H), 3.23-3.16 (m, 1H), 3.10-3.05 (m, 1H), 3.04-2.98 (m, 1H), 2.37-2.32 (m, 1H), 2.13-2.08 (m, 1H), 1.86-1.68 (m, 3H), 1.28 (d, J=6.4 Hz, 3H), 1.11 (d, J=7.2 Hz, 3H).

Synthesis of the Amine Sidechains

Preparation of Sarcosinamide 64

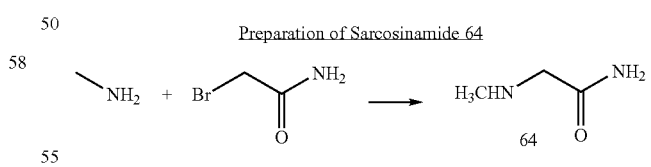

N-Methylglycinamide was prepared from methylamine and α-bromoacetamide as previously described in literature for sarcosinamide hydrochloride, (Marvel, C. S.; Elliott, J. R.; Boettner, F. E.; Yuska, H., *J. Am. Chem. Soc.* 1946, 68, 1681-1686).

To a stirred solution of bromoacetamide (3.73 g, 27 mmol) in anhydrous THF (40 mL) at 0° C. under N₂ atomosphere was added a solution of methylamine in THF (2.0M in THF, 115 mL, 230 mmol), so as to maintain an internal temperature below 5° C. The reaction mixture was aged at 0-5° C. for 3 h (monitored by TLC) and then allowed to warm to rt and evaporated under reduced pressure. The crude hydrobromide salt was dissolved in methanol and the pH adjusted to 8-9 with NaOH solution in methanol. The solvent was removed under reduced pressure and crude material was dried under high vacuum, and then treated with ACN and stirred for several minutes. The insoluble material was filtered off and washed with ACN (2×10 mL). The combined filtrate was concentrated under reduced pressure, and the residue was purified by flash chromatography on silica gel (eluent—acetonitrile followed by acetonitrile/water with gradient) to give the desired product 64 in 75% yield.

$^1$H NMR (DMSO-$d_6$, 300 MHz): δ 7.28 (br s, 1H), 7.05 (br s, 1H), 3.00 (s, 2H), 2.22 (s, 3H).

2-(N-Methylamino)-1-Carbonyl Ethylsulfamide 65

N-Boc-protected sarcosine was activated as its N-hydroxysuccinimido ester and then allowed to react with sulfamide to give, after deprotection, the desired product 65.

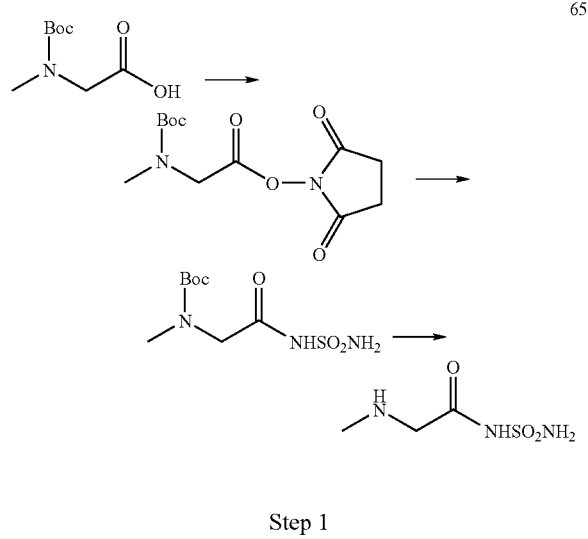

Step 1

To a stirred solution of N-BOC amino acid (10 mmol) in dry DCM (30 mL) at 0° C. were added N-hydroxysuccinimide (15 mmol) and 1-[3-(dimethylamino)propyl]-3-ethylcarbodiimide hydrochloride (EDC, 12 mmol). The resulting mixture was allowed to warm to room temperature, stirred for ~20 h (monitoring by TLC) and concentrated under reduced pressure. The residue was then dissolved in ethyl acetate (50 mL), washed with water (4×10 mL) and brine (1 omL), dried over $Na_2SO_4$, concentrated, and dried under high vacuum to give the hydroxysuccinimido ester in quantitative yield.

$^1$H NMR (CDCl$_3$, 300 MHz): δ 4.24 (s, 2H), 3.00 (s, 3H), 2.86 (s, 4H), 1.47 (s, 9H).

Step 2

To a solution of the N-Boc-N-hydroxysuccinimido ester of sarcosine (2.86 g, 10.0 mmol) in dry DMF (20 mL) was added sulfamide (1.92 g, 20.0 mmol) and the resulting mixture was stirred under nitrogen at 90°-95° C. for 8 h (monitoring by TLC). The mixture was then filtered, and the filtrate was evaporated under reduced pressure. The residue was dried under high vacuum and then dissolved in ethyl acetate (20 mL). The resulting solution was extensively washed with water (monitoring by TLC) and the combined organics were dried over $Na_2SO_4$ and concentrated under reduced pressure to give crude material. After drying under high vacuum, the material was triturated from ethyl acetate and hexanes and the insoluble material removed by filtration. The filtrate was evaporated under reduced pressure and the remaining solid was washed with ethyl ether, dissolved in DCM, and the product precipitated by adding hexanes.

Percent yield: 70%; $^1$H NMR (CDCl$_3$, 300 MHz): δ 6.60-6.30 (m, 2H), 3.88 (s, 2H), 2.94 (s, 9H).

Step 3

To a stirred solution of Boc-protected amine (1.0 mmol) in DCM (2-5 mL) at 0° C. was added trifluoroacetic acid (95% aqueous solution, 0.5 mL) and the mixture was stirred at 0° C. for 30 minutes, and then allowed to warm to rt and stirred overnight. The volatiles were evaporated under reduced pressure and the residue was treated two times with ethyl ether and evaporated yielding the corresponding amine TFA salt. The salt was dissolved in methanol and treated with NaOH solution in methanol (pH adjusted to 8-9) and concentrated. The remaining solid was partitioned between ethyl acetate and water, the layers separated, and the organic layer was dried and concentrated to produce the desired product in quantitative yield.

$^1$H NMR (DMSO-$d_6$, 300 MHz): δ 7.25 (s, 1H), 7.03 (s, 1H), 3.04 (s, 2H), 2.22 (s, 3H).

N-Methyl-N'-PNB Ethylenediamine 66

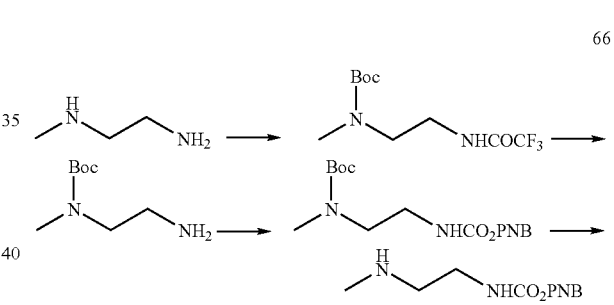

The synthesis involved the selective protection of the two amine groups in N-methylethylenediamine, first with ethyl-trifluoroacetate and, second, with di-tert-butyl dicarbonate, followed by removal of the trifluoroacetyl group and reaction of this amine with p-nitrobenzylchloroformate. The synthesis ends with the removal of the Boc-protecting group.

Steps 1 and 2

The procedure used to make N-Boc-N-methyl ethylenediamine was similar to that previously described in literature (Martins, E. T.; Baruah, H.; Kramarczyk, J.; Saluta, G.; Day, C. S.; Kucera, G. L.; Bierbach, U. *J. Med. Chem.* 2001, 44, 4492-4496).

Step 3

To a stirred solution of N-Boc-N-methyl ethylenediamine (1.39 g, 8.0 mmol) and DIEA (1.05 g, 8.1 mmol) in dry DCM (50 mL) at 0° C. was added a solution of p-nitrobenzylchloroformate (1.75 g, 8.1 mmol) in dry DCM (10 mL) dropwise over 5-10 minutes. The reaction mixture was stirred at this temperature for 30 minutes and then allowed to warm to room temperature, and stirred overnight (monitored by TLC). The reaction mixture was then washed with 1M aq. NaHCO₃ solution, water, and brine. The organic layer was dried over Na₂SO₄, concentrated, and the remaining residue was purified by flash chromatography to give the desired N-Boc-N'-PNB protected intermediate in 73% yield.

¹H NMR (CDCl₃, 300 MHz): δ 8.21 (d, J=8.4 Hz, 2H), 7.50 (d, J=9.0 Hz, 2H), 5.19 (s, 2H), 3.38 (br s, 4H), 2.89 (s, 3H), 1.45 (s, 9H).

Step 4

Sidechain 66 was prepared using standard TFA deprotection reaction conditions and purified by flash column chromatography on silica gel.

Percent yield; quantitative; ¹H NMR (acetone-d₆, 300 MHz): δ 8.20 (d, J=8.7 Hz, 2H), 7.62 (d, J=8.1 Hz, 2H), 7.41 (br s, 1H), 5.20 (s, 2H), 3.55 (br s, 2H), 3.18 (br s, 2H), 2.74 (s, 3H).

N-Methyl-N'-(Aminosulfonyl)Ethylenediamine 67

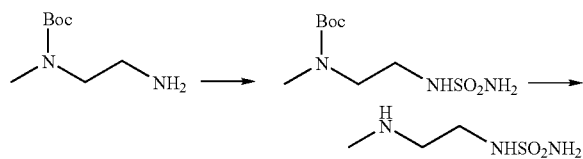

67

This sidechain was prepared by treating N-Boc-N-methyl-ethylenediamine with an excess of sulfamide in refluxing dioxane followed by N-Boc deprotection.

Step 1

A solution of N-Boc-N-methylethylenediamine (1 g, 5.74 mmol) and sulfamide (1.1 g, 11.48 mmol) in dioxane (20 mL) was stirred at reflux under N₂ atmosphere (monitored by TLC). The mixture was then filtered to remove the insoluble material and the filtrate was concentrated under reduced pressure and treated with ethyl acetate. The insoluble material was again removed by filtration and the filtrate concentrated under reduced pressure to give the desired product in 96% yield.

¹H NMR (acetone-d₆, 300 MHz): δ 5.91 (br s, 2H), 5.77 (br s, 1H), 3.38 (t, J=6.3 Hz, 2H), 3.20 (t, J=6.3 Hz, 2H), 2.85 (s, 3H), 1.40 (s, 9H).

Step 2

Percent yield: 91%; ¹H NMR (acetone-d₆, 300 MHz) δ: 6.62 (br s, 2H), 6.34 (br s, 1H), 3.48 (t, J=4.8 Hz, 2H), 3.32 (t, J=4.8 Hz, 2H) 2.80 (s, 3H).

1-[2-(N-Methylamino)Ethyl]Imidazole 68

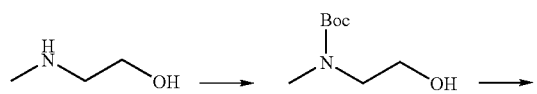

68

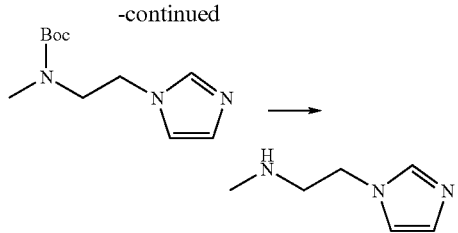

1-[2-(N-methylamino)ethyl]imidazole was synthesized from the mesylate of 2-(N-Boc-N-methylamono)ethanol, which was allowed to react with imidazole in the presence of LiHMDS. The starting material was prepared by selective protection of amino group with Boc-anhydride in the presence of Al₂O₃ according to the procedure described in literature (Yadar, V. K.; Ganesh Babu, K. *J. Org. Chem.* 2004, 69, 577-580).

Preparation of 1-[2-(N-Boc-N-Methylamino)Ethyl]Imidazole

To a stirred solution of imidazole (1.02 g, 15 mmol) at −30° C. under N₂ atmosphere in dry DMF (20 mL) was added LHMDS (1M solution in hexanes, 16.0 mL, 16.0 mmol), dropwise, by syringe. The reaction mixture was stirred at −30° C. for 40 minutes. To this mixture was added a solution of the mesylate from 2-(N-Boc-N-methylamino)ethanol (freshly prepared from 2-(N-Boc-N-methylamino)ethanol, mesyl chloride, and DIEA, (1.75 g, 10 mmol)) in DMF (6 mL) via syringe. The resulting mixture was stirred at −30° C. for 30 minutes and then at rt overnight (monitored by TLC). The mixture was then evaporated under reduced pressure and purified by flash chromatography on silica gel to produce the desired Boc-protected amine in 54% yield.

¹H NMR (CDCl₃, 300 MHz) δ: 7.09 (s, 1H), 6.69 (s, 1H), 6.60 and 6.57 (s+s, 1H), 3.76 (t, J=6.0 Hz, 2H), 3.16 (br s, 2H), 2.40 and 2.28 (s+s, 3H), 1.10 and 1.05 (s+s, 9H).

Step 2: Preparation of Imidazole 68

Percent yield: 83%; ¹H NMR (CDCl₃, 300 MHz) δ: 7.51 (s, 1H), 7.07 (s, 1H), 6.96 (s, 1H), 4.07 (t, J=6.0 Hz, 2H), 2.93 (t, J=6.0 Hz, 2H), 2.43 (s, 3H), 1.13 (br s, 1H).

N-Methylaminoethyl-N',N'''-bis-PNB-Oxycarbonyl-Guanidine 69

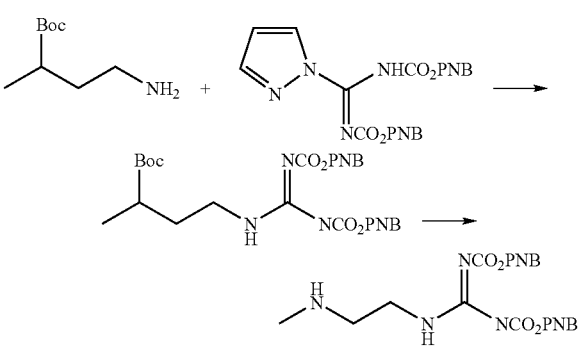

69

This sidechain was prepared by displacement of pyrazole from the bis-PNB-protected 1H-pyrazole-carboxamidine (shown above), followed by removal of the Boc protecting group.

Step 1: N-Boc-N-Methylaminoethyl-N',N''-Bis-PNB Guanidine

To a solution of N-Boc-N-methylethylenediamine (627 mg, 3.6 mmol) in dry DMF (10 mL) was added bis-PNB-protected pyrazole-1-carboxamidine (750 mg, 1.6 mmol) and the resulting mixture was stirred at rt for 3 days (monitoring by TLC). The solvent was then removed under reduced pressure and purified by flash chromatography to produce the desired Boc-protected amine in 50% yield.

$^1$H NMR (CDCl$_3$, 300 MHz) δ: 11.70 (s.1H), 8.47 and 8.35 (s+s, 1H), 8.14 (d, J=8.1 Hz, 2H), 8.11 (d, J=8.1 Hz, 2H), 7.48 (d, J=8.1 Hz, 2H), 7.46 (d, J=8.1 Hz, 2H), 5.21 (s, 2H), 5.15 (s, 2H), 3.56-3.51 (m, 2H), 3.41 (t, J=5.4 Hz, 2H), 2.81 (s, 3H), 1.34 (s, 9H).

Step 2: Amine 69

Percent yield: 89%; $^1$H NMR (CDCl$_3$, 300 MHz) δ: 11.63 (s, 1H), 9.80 (s, 1H), 8.65 (t, J=6.0 Hz, 1H), 8.19 (d, J=4.5 Hz, 2H), 8.16 (d, J=4.5 Hz, 2H), 7.51 (d, J=5.7 Hz, 2H), 7.48 (d, J=5.1 Hz, 2H), 5.23 (s, 2H), 5.20 (s, 2H), 3.76 (br s, 2H), 2.70 (s, 3H)

2-(N-Methylaminomethyl)Thiazole 70

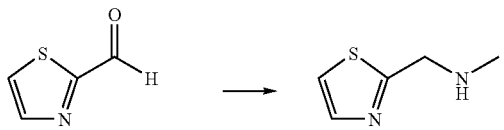

To a flask containing dry DCM (60 mL) and 4 A molecular sieves were added methylamine (2.0M solution in THF, 4.0 mL, 8.0 mmol), Na$_2$SO$_4$ (1.42 g, 10.0 mmol), and 2-thiazole-carboxaldehyde (0.452 g, 4.0 mmol). The reaction mixture was stirred at room temperature and monitored by $^1$H NMR. Upon completion, the reaction mixture filtered to remove the Na$_2$SO$_4$ and molecular sieves and the filtrate was concentrated under reduced pressure. The crude imine was dissolved in absolute EtOH (40 mL), treated with NaBH$_4$ (0.227 g, 6.0 mmol) and aged for several hours at rt (monitored by TLC). The reaction mixture was then quenched with water (8 mL) and concentrated under reduced pressure. The residue was treated with brine, extracted with DCM (3×50 mL), and the combined organic layers were dried, and evaporated under reduced pressure to give the desired product in 69% yield.

$^1$H NMR (CDCl$_3$, 300 MHz) δ: 7.69 (d, J=3.6 Hz, 1H), 7.24 (d, J=3.6 Hz, 1H0, 4.06 (s, 2H), 2.49 (s, 3H), 1.80 (br s, 1H).

2-[(Aminosulfonyl)Aminomethyl]piperazine 71

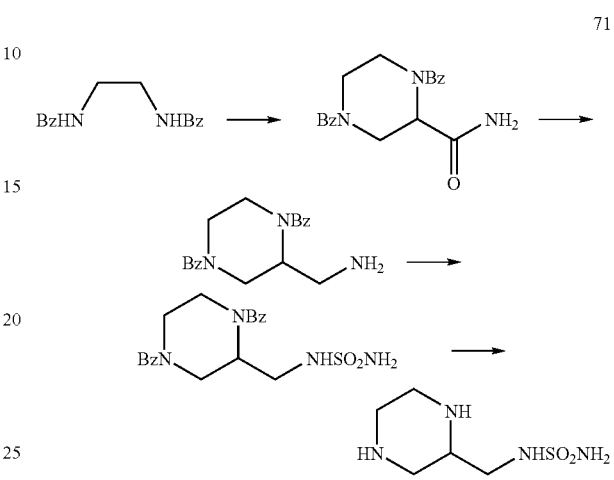

The synthesis involved preparation of 1,4-dibenzyl-piperazine-2-carboxylic acid amide, reduction of the amide to the amine with LAH, conversion of the amine to the sulfonamide, and deprotection of the bis-benzyl protecting groups.

Step 1: 1,4-Dibenzy piperazine-2-Carboxylic Acid Amide

This compound was prepared in 75% yield according to the procedure described in literature (Butts, C. P.; Jazdzyk, M. *Chem. Commu.* 2003, (13) 1530-1531)

Step 2: 1,4-Dibenzyl-2-aminomethyl-piperazine

To a stirred suspension of LAH (0.9 g, 25.9 mmol) in dry THF (150 mL) was added 1,4-dibenzyl-piperazine-2-carboxylic acid amide (4.0 g, 12.93 mmol) and the mixture was stirred under reflux for 20 h (monitored by TLC). The stirred mixture was cooled with an ice-bath and quenched with Rochelle's salt (6 mL), warmed to room temperature, and the suspension was poured over a pad of silica gel (20 mm). The celite was washed with 15% MeOH in CH$_2$Cl$_2$ with 1% NH$_4$OH (3×50 mL) and eluted through pad of silica gel. Th eluent was concentrated under reduced pressure to give the desired product in 99% yield.

$^1$H NMR (CDCl$_3$, 300 MHz): δ 7.32-7.31 (m, 10H), 4.05 (d, J=13.8 Hz, 1H), 3.52 and 3.47 (ABq, J=12.9 Hz, 2H), 3.27 (d, J=13.8 Hz, 1H), 3.06 (dd, J=13.2; 5.7 Hz, 1H), 2.82-2.69 (m, 3H), 2.63-2.58 (m, 1H), 2.50-2.43 (m, 1H), 2.36-2.16 (m, 3H).

Step 3: 1,4-Dibenzyl-2-[(Aminosulfonyl)Aminomethyl]piperazine

To a solution of 1,4-dibenzyl-2-aminomethyl-piperazine (2.5 g, 8.46 mmol) in dioxane (50 mL), was added sulfamide (1.63 g, 16.9 mmol) and the resulting mixture was stirred at 95° C. under N$_2$ atmosphere for several hours (monitored by TLC). The solvent was removed under reduced pressure and the crude material was purified by flash chromatography on silica gel using acetonitrile/water with gradient as eluent.

Percent yield: 58%; $^1$H NMR (CDCl$_3$, 300 MHz) δ: 7.37-7.29 (m, 10H), 5.64 (br s, 1H), 4.24 (br s, 2H), 3.94 (d, J=12.9 Hz, 1H), 3.59-3.46 (m, 4H), 3.13 (d, J=12.9 Hz, 1H), 2.96-2.91 (m, 1H), 2.81-2.76 (m, 1H).

Step 4: 2-[(Aminosulfonyl)Aminomethyl]Piperazine

A mixture of 1,4-dibenzyl-piperazine-2-methylsulfamide (1.82 g, 4.87 mmol) in MeOH (20 mL) and 10% Pd/C (180 mg) was treated with hydrogen gas (65 psi) for 27 h at rt. The mixture was then filtered through a pad of Celite and the celite washed well with methanol. The filtrate was concentrated under reduced pressure to give the desired product 71 in 96% yield.

$^1$H NMR (DMSO-d$_6$, 300 MHz) δ: 6.48 (br s, 1H), 6.42 (br s, 1H), 3.20-3.13 (m, 2H), 2.77-2.62 (m, 3H), 2.57-2.50 (m, 2H), 2.47-2.39 (m with DMSO-d$_6$ peak, 1H), 2.11 (dd, J=11.4; 9.6 Hz, 1H).

(2S)-2-[(Aminosulfonyl)aminocarbonyl]pyrrolidine 72

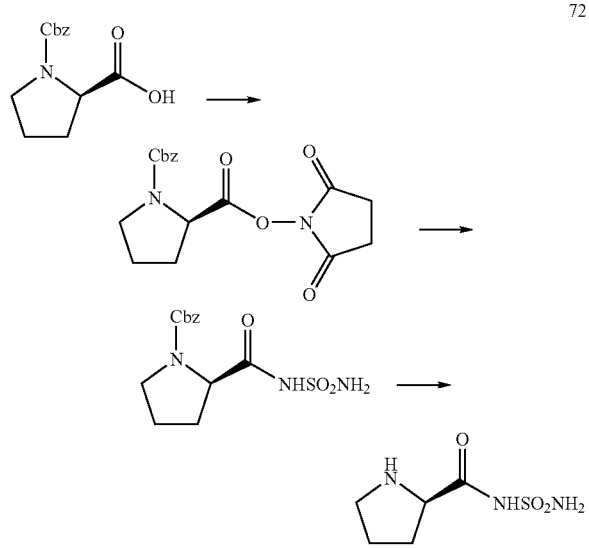

(2S)-1-Cbz-2-[(Aminosulfonyl)Aminocarbonyl]Pyrrolidine

Percent yield: 42%; $^1$H NMR (CDCl$_3$, 300 MHz): δ 7.34-7.26 (m, 5H), 6.76 (s, 1H), 6.42-6.26 (m, 2H), 5.11 (s, 2H), 4.31 (br s, 1H), 3.52-3.40 (m, 2H), 2.20-2.11 (m, 2H), 1.95-1.86 (m, 3H).

(2S)-2-[(Aminosulfonyl)Aminocarbonyl]Pyrrolidine 72

Percent yield: 95%; $^1$H NMR (CDCl$_3$, 300 MHz) δ: 7.40 (br s, 1H), 6.16 (br s, 1H), 3.69 (dd, J=9.0; 5.1 Hz), 3.06-2.85 (m, 2H), 2.35 (br s, 1H), 2.17-2.05 (m, 1H), 1.94-1.83(m,1H), 1.80-1.59 (m, 2H).

Synthesis of Secondary Amines by Alkylation

The synthesis of a series of 2-, 3- or 4-(alkylamino)alkylpyridines was achieved by protection of 2-, 3- or 4-aminoalkylpyridines with Boc anhydride in t-butyl alcohol followed by treatment with sodium hydride in DMF and alkylation with various alkyl halides. Lastly, removal of the Boc protecting group was accomplished with 95% TFA in DCM. This synthetic strategy was first reported in literature for preparation of 2-(alkylamino)pyridines (Krein, D. M.; Lowary, T. L. *J. Org. Chem.* 2002, 67, 4965-4967).

Examples of Prepared Amines:

2-(Methylaminomethyl)-5-methylpyrazine—66% overall yield; $^1$H NMR (CDCl$_3$, 300 MHz) δ: 8.42 (s, 1H), 8.35 (s, 1H), 3.83 (s, 2H), 2.50 (s, 3H), 2.43 (s, 3H).

2-(methylaminomethyl)pyridine—55% overall yield; $^1$H NMR (CDCl$_3$, 300 MHz) δ: 8.58 (s, 1H), 7.71 (t, J=8.4 Hz, 1H), 7.31-7.24 (m, 2H), 4.01 (s, 2H), 2.54 (s, 3H).

3-[(4-thiazolomethylamino)methyl]pyridine—42% overall yield; $^1$H NMR (CDCl$_3$, 300 MHz) δ: 8.79 (d, J=1.2 Hz, 1H), 8.57 (d, J=4.2 Hz, 1H), 8.08 (dt, J=8.1; 2.4 Hz, 7.35 (d, J=6.9 Hz,1H), 7.24 (br s, 1H), 7.19-7.15 (m, 1H), 4.06 (s, 2H), 3.99 (s, 2H), 2.80 (s, 1H).

Dilution Antimicrobial Susceptibility Tests

The agar dilution method for determining the antimicrobial susceptibility was carried out using an agar dilution method with Mueller-Hinton agar (see, M7-A5, Vol. 20 (2), 2000). A final inoculum of 104 CFU was applied with a replicating device. Broth dilution tests wre performed with 5×105 CFU in tubes containing 1 mL of broth. Incubation of test tubes containing agar and broth was done at 35 C for 18 h. The susceptibilities of streptococci were determined by Mueller-Hinton agar supplemented with 5% sheep blood, and the susceptibility of anaerobic species was determined with brucella agar supplemented with 5% sheep blood, hemin, and vitamin K. Incubation of anaerobic cultures was done for 48 h in jars. The susceptibilities of methicillin-resistant staphylococci were determined on Mueller-Hinton agar or in broth supplemented with 3% NaCl. All assays were run with the indicated control strains, available from the American Type Culture Collection, Rockville, Md.). Results of the antimicrobial susceptibility tests of compounds 9-63 against Gram-negative organisms are shown in Table I.

The compositions, methods and/or processes disclosed and claimed herein can be made and executed without undue experimentation in light of the present disclosure. While the compositions and methods of this invention have been described in terms of preferred embodiments, it will be apparent to those of skill in the art that variations may be applied to the compositions, methods and/or processes and in the steps or in the sequence of steps of the methods described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention.

The invention claimed is:
1. A carbapenem compound of the formula I:

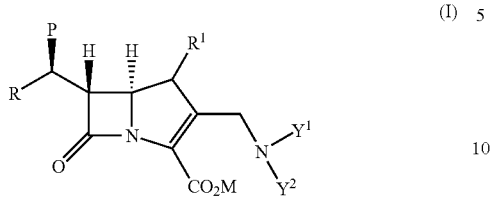

or pharmaceutically acceptable salts or prodrugs thereof, wherein:
R is H or alkyl;
$R^1$ is H or alkyl;
M is H or a group such that $CO_2M$ is a carboxylic acid, a carboxylate anion balanced by a counterion or a charged $R^i$ or Q group of the compound of formula I, a pharmaceutically acceptable ester group, or a carboxylic acid protected by a protecting group;
P is selected from the group consisting of hydrogen, hydroxyl, halogen or hydroxyl protected by a hydroxyl protecting group; and
$Y^1$ is selected from the group consisting of hydrogen; halogen; —CN; —$NO_2$; —$NR^aR^b$; —$OR^c$; —$SR^c$; —C(O)$NR^aR^b$; —C(O)$OR^h$; S(O)$R^c$; —$SO_2R^c$; —$SO_2NR^aR^b$; —$NR^aSO_2R^b$; —C(O)$R^a$; —OC(O)$R^a$; OC(O)$NR^aR^b$; —$NR^aC(O)NR^bR^c$; —$NR^aCO_2R^h$; —$OCO_2R^h$; $NR^aC(O)R^b$; $C_{1-6}$ straight- or branched-chain alkyl that are substituted or unsubstituted with one to four $R^d$ groups; alkylaryl, -A-$(CH_2)_n$-Q and $C_{3-7}$ cycloalkyl, substituted or unsubstituted with one to four $R^d$ groups;
$Y^2$ is selected from the group consisting halogen; —CN; —$NO_2$; —$NR^aR^b$; —$OR^c$; —$SR^c$; —C(O)$NR^aR^b$; —C(O)$OR^h$; S(O)$R^c$; —$SO_2R^c$; —$SO_2NR^aR^b$; —$NR^aSO_2R^b$; —C(O)$R^a$; —OC(O)$R^a$; OC(O)$NR^aR^b$; —$NR^aC(O)NR^bR^c$; —$NR^aCO_2R^h$; —$OCO_2R^h$; $NR^aC(O)R^b$; $C_{1-6}$ straight- or branched-chain alkyl that are substituted with one to four $R^d$ groups; alkylaryl, -A-$(CH_2)_n$-Q and $C_{3-7}$ cycloalkyl, substituted or unsubstituted with one to four $R^d$ groups, wherein:
A is O, S, NH, $NCH_3$, NR, or —$CH_2$—;
n is 0, 1, 2 or 3;
each $R^a$, $R^b$ and $R^c$ is independently selected from hydrogen, —$C_{1-6}$ straight- or branched-chain alkyl, unsubstituted or substituted with one to four $R^d$ groups, or —$C_{3-7}$ cycloalkyl, unsubstituted or substituted with one to four $R^d$ groups;
or $R^a$ and $R^b$ taken together with any intervening atoms is a 4-6 membered saturated ring optionally interrupted by one or more of O, S, $NR^c$, or —C(O)—, the ring being unsubstituted or substituted with one to four $R^i$ groups;
or $R^b$ and $R^c$ taken together with any intervening atoms is a 4-6 membered saturated ring optionally interrupted by one to three of O, S, $NR^a$, with $R^a$ as defined above, or —C(O)—, the ring being unsubstituted or substituted with one to four $R^i$ groups;
each $R^d$ is independently halogen; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; $NR^eCONR^fR^g$; —$NR^eCO_2R^f$; —$OCO_2R^g$; —C($NR^e$)$NR^fR^g$; $NR^eC(NH)NR^fR^g$ or —$NR^eC(NR^f)R^g$;

each $R^e$, $R^f$ and $R^g$ is selected from hydrogen; —$R^h$; —$C_{1-6}$ straight- or branched-chain alkyl unsubstituted or substituted with one to four $R^i$ groups or $R^e$ and $R^f$ taken together with any intervening atoms is a 4-6 membered saturated ring optionally interrupted by one to three of O, S, —C(O)— or $NR^g$ with $R^g$ as defined above, the ring being unsubstituted or substituted with one to four $R^i$ groups;
each $R^i$ is independently selected from halogen; —CN; —$NO_2$; phenyl; —$NHSO_2R^h$; —$OR^h$, —$SR^h$; —$N(R^h)_2$; —$N^+(R^h)_3$; —C(O)$N(R^h)_2$; $SO_2N(R^h)_2$; heteroaryl; heteroarylium; —$CO_2R^h$; —C(O)$R^h$; —$OCOR^h$; $NHCOR^h$; guanidinyl; carbamimidoyl or ureido;
each $R^h$ is independently selected from hydrogen, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4-6 membered saturated ring, optionally interrupted by one or two of O, S, $SO_2$, —C(O)—, NH and $NCH_3$;
each Q is selected from the group consisting of:

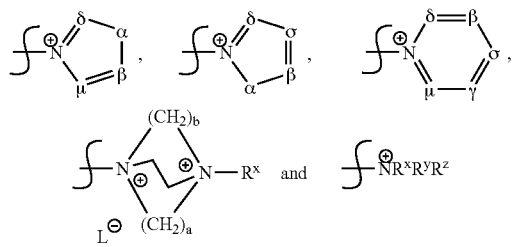

wherein:
a and b are 1, 2 or 3;
$L^-$ is a pharmaceutically acceptable counterion;
α is O, S or $NR^s$;
β, δ, λ, μ, and σ are independently $CR^t$, N;
each $R^s$ is independently selected from hydrogen; phenyl or $C_{1-6}$ straight- or branched-chain alkyl, unsubstituted or substituted with one to four $R^i$ groups;
each $R^t$ is independently selected from hydrogen; halo; phenyl; —CN; —$NO_2$; —$NR^uR^v$; —$OR^u$; —$SR^u$; $CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; —$C_{1-6}$ straight- or branched-chain alkyl, unsubstituted or substituted with one to four $R^i$ groups;
each $R^u$ and $R^v$ is independently selected from hydrogen or —$C_{1-6}$ straight- or branched-chain alkyl, unsubstituted or substituted with one to four $R^i$ groups or $R^u$ and $R^v$ together with any intervening atoms is a 4-6 membered saturated ring optionally interrupted by one or more of O, S, $NR^w$ or —C(O)—, the ring being unsubstituted or substituted with one to four $R^i$ groups;
each $R^w$ is independently selected from hydrogen; —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1-4 $R^i$ groups; or $R^h$ and $R^w$ taken together with any intervening atoms represent a 5-6 membered saturated ring, optionally interrupted by one or two of O, S, SO$_2$, NH or NCH$_3$;

each R$^x$ is independently hydrogen or a C$_{1-8}$ straight- or branched chain alkyl, optionally interrupted by one or two of O, S, SO, SO$_2$, NR$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)N-R$^h$R$^w$, or a phenyl or heteroaryl group which is in turn optionally substituted with from one to four R$^i$ groups or with one to two C$_{1-3}$ straight- or branched-chain alkyl groups, said alkyl groups being unsubstituted or substituted with one to four R$^i$ groups;

each R$^y$ and R$^z$ is independently selected from hydrogen; phenyl; —C$_{1-6}$ straight or branched chain alkyl, unsubstituted or substituted with one to four R$^i$ groups, and optionally interrupted by O, S, NR$^w$ or —C(O)— or R$^x$ and R$^y$ together with any intervening atoms is a 4-6 membered saturated ring optionally interrupted by O, S, SO$_2$, NR$^w$ or —C(O)—, unsubstituted or substituted with 1-4 R$^i$ groups, or, when R$^x$ and R$^y$ together are a 4-6 membered ring, R$^z$ is an additional saturated 4-6 membered ring fused to the R$^x$ and R$^y$ ring, optionally interrupted by O, S, NR$^w$ or —C(O)—, the rings being unsubstituted or substituted with one to four R$^i$ groups.

2. A carbapenem compound of the formula II,

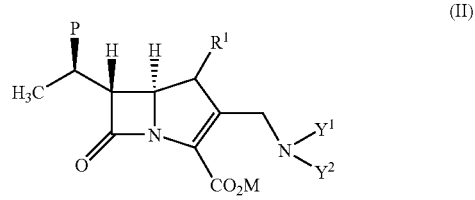

(II)

or pharmaceutically acceptable salts thereof, wherein:
R$^1$ is hydrogen or methyl;
P is hydrogen or hydroxyl;
M is H or a group such that CO$_2$M is a carboxylic acid, a carboxylate anion balanced by a counterion, a pharmaceutically acceptable ester group, or a carboxylic acid protected by a protecting group;
Y$^1$ is H or R$^2$, wherein R$^2$ is H or C$_1$-C$_4$ alkyl; and
Y$^2$ is —(CH$_2$)$_n$-A, wherein n is 0-4 and A is —CN, —OR$^2$, —SR$^2$, —N(R$^2$)$_2$, CO$_2$R$^2$, C(O)—N(R$^2$)$_2$, —C(O)—NR$^2$SO$_2$N(R$^2$)$_2$, NR$^2$SO$_2$N(R$^2$)$_2$, NH—C(=NR$^2$)—N(R$^2$)$_2$, —S—C(=NR$^2$)—N(R$^2$)$_2$, wherein each R$^2$ is independently H or C$_1$-C$_4$ alkyl.

3. The carbapenem compound of claim 2 wherein the carbapenem is of the formula III,

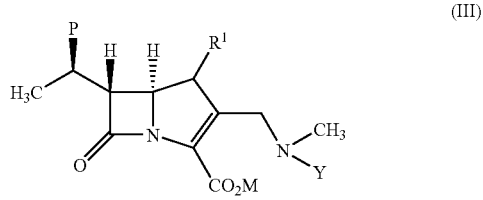

(III)

or pharmaceutically acceptable salts thereof, wherein:

R$^1$ hydrogen or methyl;
P is hydrogen or hydroxyl;
M is H or a group such that CO$_2$M is a carboxylic acid, a carboxylate anion balanced by a counterion, a pharmaceutically acceptable ester group, or a carboxylic acid protected by a protecting group; and
Y is —(CH$_2$)$_n$-A, wherein n is 0-4 and A is —CN, —OR$^2$, —SR$^2$, —N(R$^2$)$_2$, CO$_2$R$^2$, C(=O)—N(R$^2$)$_2$, —C(=O)—NR$^2$SO$_2$N(R$^2$)$_2$, NR$^2$SO$_2$N(R$^2$)$_2$, NH—C(=NR$^2$)—N(R$^2$)$_2$, —S—C(=NR$^2$)—N(R$^2$)$_2$, wherein each R$^2$ is independently H or C$_1$-C$_4$ alkyl.

4. A carbapenem compound of the formula IV,

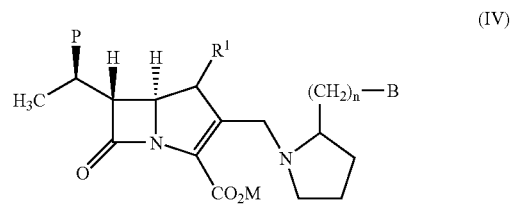

(IV)

or pharmaceutically acceptable salts thereof, wherein:
R$^1$ is H or methyl;
P is hydrogen or hydroxyl;
n=0-4;
M is H or a group such that CO$_2$M is a carboxylic acid, a carboxylate anion balanced by a counterion, a pharmaceutically acceptable ester group, or a carboxylic acid protected by a protecting group; and
B is —OR$^2$, —SR$^2$, —CO$_2$R$^2$, CO—N(R$^2$)H, —CO—NR$^2$SO$_2$N(R$^2$)$_2$, NR$^2$SO$_2$N(R$^2$)$_2$, NH—C(=NR$^2$)—N(R$^2$)$_2$, —S—C(=NR$^2$)—N(R$^2$)$_2$, wherein each R$^2$ is independently H or C$_1$-C$_4$ alkyl.

5. The compound of claim 4, wherein P is hydroxyl; R$^1$ is methyl; n is 0 or 1; and B is CONH$_2$, —CONHSO$_2$NH$_2$, NHSO$_2$NH$_2$, NH—C(=NH)—NH$_2$ or —S—C(=NH)—NH$_2$.

6. A carbapenem compound of the formula V,

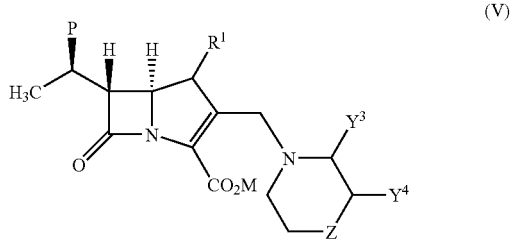

(V)

or pharmaceutically acceptable salts thereof, wherein:
R$^1$ is hydrogen or methyl;
P is hydrogen or hydroxyl;
M is H or a group such that CO$_2$M is a carboxylic acid, a carboxylate anion balanced by a counterion, a pharmaceutically acceptable ester group, or a carboxylic acid protected by a protecting group;
Z is —O, —S, —N(R$^2$); and
each Y$^3$ and Y$^4$ is independently hydrogen or —(CH$_2$)$_n$-A, wherein n=0-4 and A is selected from —N(R$^2$)$_2$, —CO$_2$R$^2$, —CO—N(R$^2$)$_2$, —CO—NR$^2$SO$_2$N(R$^2$)$_2$, NR$^2$SO$_2$N(R$^2$)$_2$, NH—C(=NR$^2$)—N(R$^2$)$_2$, —S—C(=NR$^2$)—N(R$^2$)$_2$, wherein each R$^2$ is H or C$_1$-C$_4$ alkyl.

7. The compound of claim 6, wherein: P is hydroxyl; $R^1$ is methyl; Z is NH; and each $Y^3$ and $Y^4$ is independently hydrogen or —$(CH_2)_n$-A, wherein n=0-2 and A is —$N(R^2)_2$, —$CON(R^2)_2$, —CO—$NHSO_2NH_2$, or $NHSO_2NH_2$ wherein each $R^2$ is hydrogen or methyl.

8. The compound of claim 1 wherein the compound is compound 9:

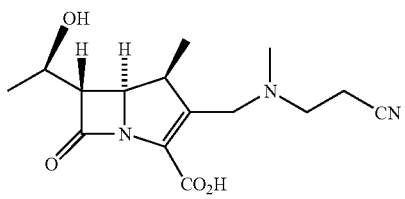

or a pharmaceutically acceptable salt or prodrug thereof.

9. The compound of claim 1 wherein the compound is compound 12:

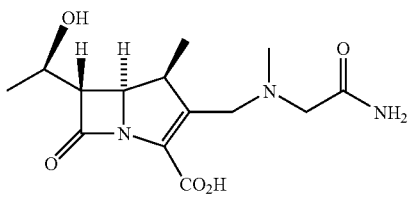

or a pharmaceutically acceptable salt or prodrug thereof.

10. The compound of claim 2 wherein the compound is compound 15:

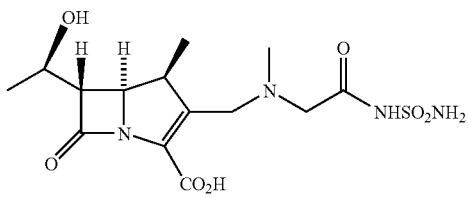

or a pharmaceutically acceptable salt or prodrug thereof.

11. The compound of claim 1 wherein the compound is compound 18:

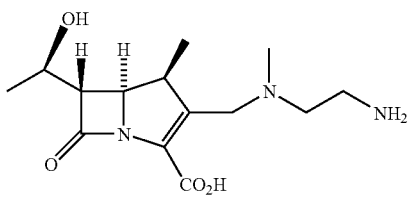

or a pharmaceutically acceptable salt or prodrug thereof.

12. The compound of claim 2 wherein the compound is compound 21:

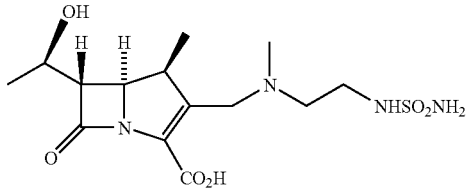

or a pharmaceutically acceptable salt or prodrug thereof.

13. The compound of claim 1 wherein the compound is compound 25:

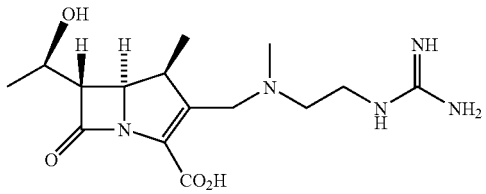

or a pharmaceutically acceptable salt or prodrug thereof.

14. The compound of claim 1 wherein the compound is compound 28:

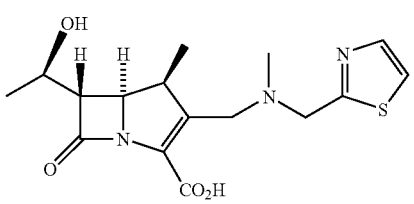

or a pharmaceutically acceptable salt or prodrug thereof.

15. The compound of claim 4 wherein the compound is compound 32:

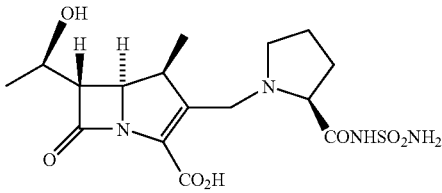

or a pharmaceutically acceptable salt or prodrug thereof.

16. The compound of claim 6 wherein the compound is compound 34:

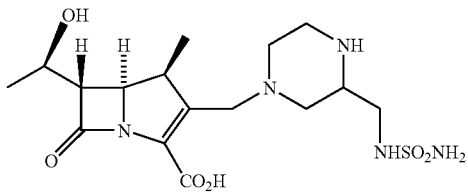

34 or a pharmaceutically acceptable salt or prodrug thereof.

17. The compound of claim 6 wherein the compound is compound 36:

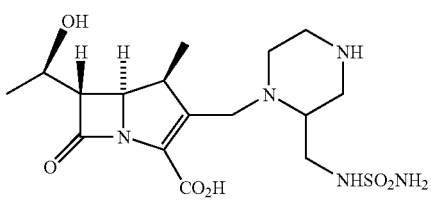

36 or a pharmaceutically acceptable salt or prodrug thereof.

18. The compound of claim 4 wherein the compound is compound 39:

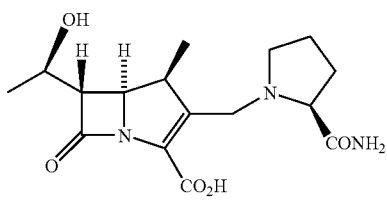

39 or a pharmaceutically acceptable salt or prodrug thereof.

19. A pharmaceutical composition comprising a compound of claim 1 and a pharmaceutically acceptable carrier.

20. A pharmaceutical composition comprising a compound of claim 2 and a pharmaceutically acceptable carrier.

21. A pharmaceutical composition comprising a compound of claim 3 and a pharmaceutically acceptable carrier.

22. A pharmaceutical composition comprising a compound of claim 4 and a pharmaceutically acceptable carrier.

23. The composition of claim 22, wherein P is hydroxyl; $R^1$ is methyl; n is 0 or 1; and B is $CONH_2$, —$CONHSO_2NH_2$, $NHSO_2NH_2$, NH—C(=NH)—$NH_2$ or —S—C(=NH)—$NH_2$.

24. A pharmaceutical composition comprising a compound of claim 6 and a pharmaceutically acceptable carrier.

25. The composition of claim 24, wherein P is hydroxyl; $R^1$ is methyl; Z is NH; and each $Y^3$ and $Y^4$ is independently hydrogen or —$(CH_2)_n$-A, wherein n=0-2 and A is —$N(R^2)_2$, —$CON(R_2)_2$, —CO—$NHSO_2NH_2$ or $NHSO_2NH_2$ wherein each $R^2$ is hydrogen or methyl.

26. The composition of claims 19, 20 or 21, wherein the compound is selected from the group consisting of compound 9, 12, 15, 18, 21 and 25,

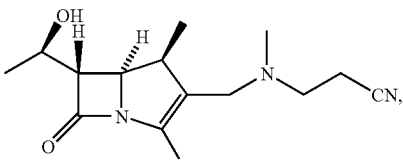

9

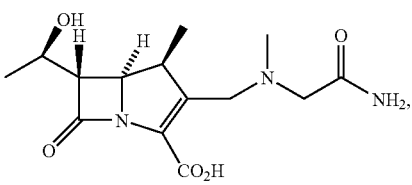

12

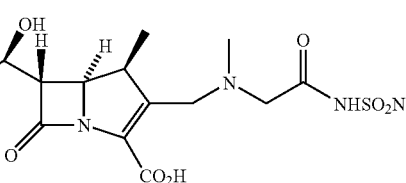

15

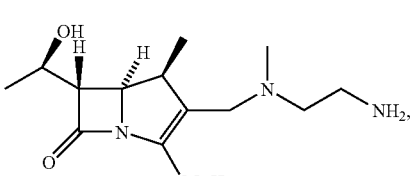

18

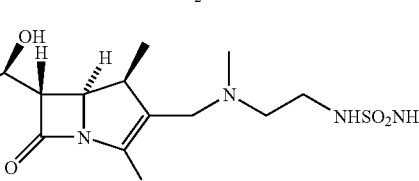

21

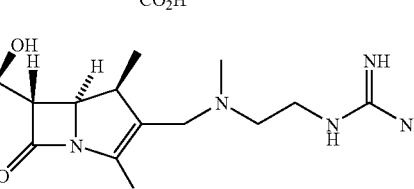

25 or a pharmaceutically acceptable salt thereof.

27. A method of preventing or treating an infection by a gram negative bacteria in a host comprising administering to the host a therapeutic amount of a compound of claim 1, optionally in a pharmaceutically acceptable carrier.

28. A method of preventing or treating an infection by a gram negative bacteria in a host comprising administering to the host a therapeutic amount of a compound of claim 2, optionally in a pharmaceutically acceptable carrier.

29. A method of preventing or treating an infection by a gram negative bacteria in a host comprising administering to the host a therapeutic amount of a compound of claim 4, optionally in a pharmaceutically acceptable carrier.

30. The method of claim 29, wherein P is hydroxyl; $R^1$ is methyl; n is 0 or 1; and B is $CONH_2$, —$CONHSO_2NH_2$, $NHSO_2NH_2$, NH—C(=NH)—$NH_2$ or —S—C(=NH)—$NH_2$.

31. A method of preventing or treating an infection by a gram negative bacteria in a host comprising administering to the host a therapeutic amount of a compound of claim 6, optionally in a pharmaceutically acceptable carrier.

32. The method of claim 31, wherein P is hydroxyl; $R^1$ is methyl; Z is NH; and each $Y^3$ and $Y^4$ is independently hydrogen or —$(CH_2)_n$-A, wherein n=0-2 and A is —$N(R^2)_2$, —$CON(R^2)_2$, —CO—$NHSO_2NH_2$, or $NHSO_2NH_2$, wherein each $R^2$ is hydrogen or methyl.

33. The method of any one of claims 27 or 28, wherein the compound is selected from the group consisting of compound 9, 12, 15, 18, 21 and 25,

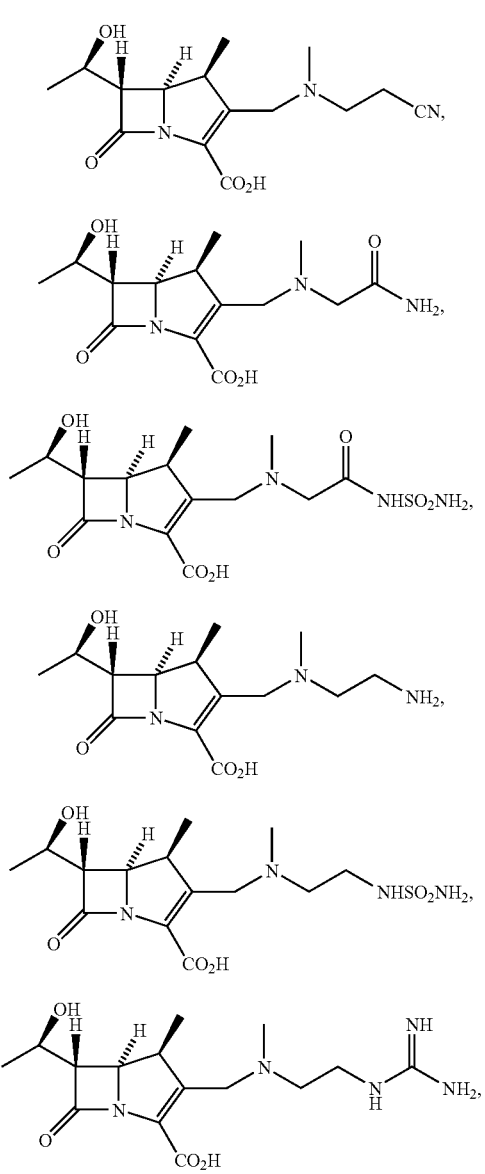

or a pharmaceutically acceptable salt thereof.

34. The method of any one of claims 27, 28, 29 or 31 wherein the host is a human.

35. The method of any one of claims 27, 28, 29 or 31 wherein the bacteria is a drug resistant bacterial strain.

36. The method of any one of claims 27, 28, 29 or 31 wherein the bacteria is a multiple-drug resistant bacterial strain.

37. The method of any one of claims 27, 28, 29 or 31 wherein the compound is administered in combination or alternation with at least one other antimicrobial agent.

38. The method of any one of claims 27, 28, 29 or 31 wherein the compound is administered in combination with a β-lactamase inhibiting agent.

39. The composition of any one of claims 19 or 22, wherein the compound is selected from the group consisting of compounds 28, 32 and 39

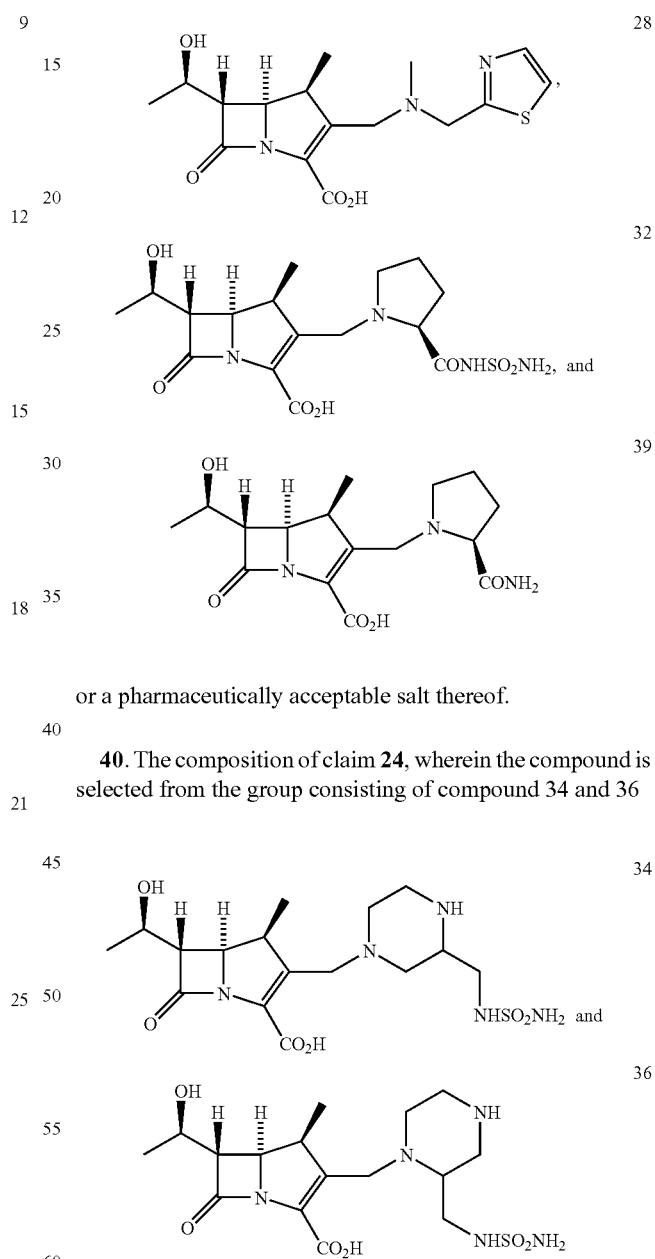

or a pharmaceutically acceptable salt thereof.

40. The composition of claim 24, wherein the compound is selected from the group consisting of compound 34 and 36

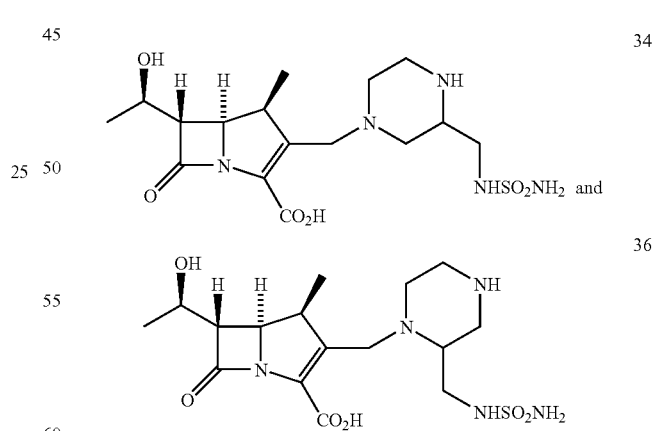

or a pharmaceutically acceptable salt thereof.

41. The method of any one of claims 27 or 29, wherein the compound is selected from the group consisting of compounds 28, 32 and 39

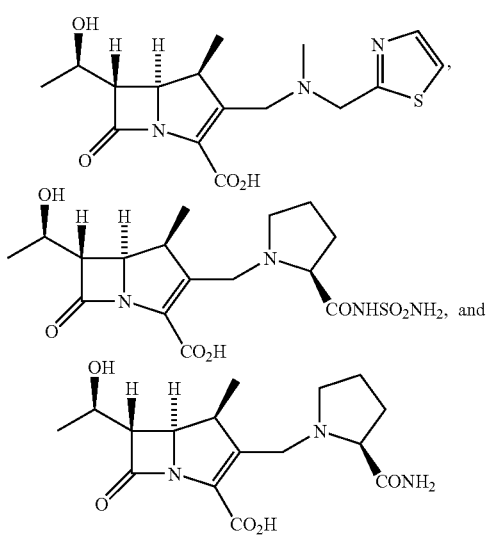
or a pharmaceutically acceptable salt thereof.
42. The method of claim 31, wherein the compound is selected from the group consisting of compound 34 and 36
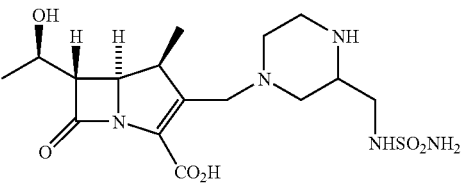
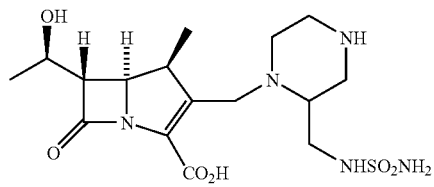
or a pharmaceutically acceptable salt thereof.
* * * * *